United States Patent
Voellmy

(10) Patent No.: US 7,906,312 B2
(45) Date of Patent: Mar. 15, 2011

(54) VIRAL VECTORS WHOSE REPLICATION AND, OPTIONALLY, PASSENGER GENE ARE CONTROLLED BY A GENE SWITCH ACTIVATED BY HEAT IN THE PRESENCE OR ABSENCE OF A SMALL-MOLECULE REGULATOR

(76) Inventor: Richard Voellmy, Pully (CH)

( * ) Notice: Subject to any disclaimer, the term of this patent is extended or adjusted under 35 U.S.C. 154(b) by 1679 days.

(21) Appl. No.: 11/148,368

(22) Filed: Jun. 9, 2005

(65) Prior Publication Data

US 2009/0017530 A1 Jan. 15, 2009

Related U.S. Application Data

(63) Continuation-in-part of application No. 10/731,961, filed on Dec. 10, 2003, now abandoned.

(51) Int. Cl.
*C12N 7/01* (2006.01)
*C12N 15/63* (2006.01)
*C12N 15/86* (2006.01)
*A61K 48/00* (2006.01)

(52) U.S. Cl. ............... 435/235.1; 435/320.1; 424/93.2; 424/93.6

(58) Field of Classification Search .................. None
See application file for complete search history.

(56) References Cited

U.S. PATENT DOCUMENTS 6,855,544 B1 * 2/2005 Hateboer et al. .............. 435/325

OTHER PUBLICATIONS

Avvakumov, N. et al., "New tools for the construction of replication-competent adenoviral vectors with altered E1A regulation", J. Vir. Meth., May 2002, vol. 103: pp. 41-49.*
Chong, H. et al., "A system for small-molecule control of conditionally replication competent adenoviral vectors", Mol. Ther., Feb. 2002, vol. 5: pp. 195-203.*

* cited by examiner

*Primary Examiner* — Michael Burkhart
(74) *Attorney, Agent, or Firm* — Richard Voellmy

(57) ABSTRACT

The present invention relates to conditionally replicating viruses or pairs of viruses containing a gene switch that is activatable by transient heat or other proteotoxic stress in the presence or absence of a small molecule regulator. The gene switch controls the expression of a gene for a protein required for efficient viral replication and may also control the activity of a passenger gene.

10 Claims, 17 Drawing Sheets

TA — transactivator protein
t-r — transactivator-responsive promoter
SMR — small molecule regulator glvp-r - GLVP-responsive promoter

A.

B.

C.

glvp-r - GLVP-responsive promoter
t-r - transactivator-responsive promoter
SMR - small molecule regulator
TA - transactivator protein
Ad - adenovirus DNA
( ) - gene region from which sequences can be optionally deleted

A

B glvp-r - GLVP-responsive promoter
t-r - transactivator-responsive promoter
SMR - small molecule regulator
TA - transactivator protein
hsp70B - glvp-r promoter
heat shock - t-r promoter  - tandem or hybrid promoters ts — transactivator - binding site
SMR — small molecule regulator
TA — transactivator protein
partial ts - heat shock promoter — hybrid promoter co-activated by TA and endogenous HSF Fig.7                    >pShuttle 6621bp
CATCATCAATAATATACCTTATTTTGGATTGAAGCCAATATGATAATGAGGGGGTGGAGTTTGTGACGTGG
CGCGGGGCGTGGGAACGGGGCGGGTGACGTAGTAGTGTGGCGGAAGTGTGATGTTGCAAGTGTGGCGGAAC
ACATGTAAGCGACGGATGTGGCAAAAGTGACGTTTTGGTGTGCGCCGGTGTACACAGGAAGTGACAATTT
TCGCGCGGTTTTAGGCGGATGTTGTAGTAAATTTGGGCGTAACCGAGTAAGATTTGGCCATTTTCGCGGGA
AAACTGAATAAGAGGAAGTGAAATCTGAATAATTTTGTGTTACTCATAGCGCGTAATACTGGTACCGCGGC
CGCCTCGAGTCTAGAGATATCGAATTCAAGCTTGTCGACTCGAAGATCTGGGCGTGGTTAAGGGTGGGAAA
GAATATATAAGGTGGGGGTCTTATGTAGTTTTGTATCTGTTTTGCAGCAGCCGCCGCCGCCATGAGCACCA
ACTCGTTTGATGGAAGCATTGTGAGCTCATATTTGACAACGCGCATGCCCCCATGGGCCGGGGTGCGTCAG
AATGTGATGGGCTCCAGCATTGATGGTCGCCCCGTCCTGCCCGCAAACTCTACTACCTTGACCTACGAGAC
CGTGTCTGGAACGCCGTTGGAGACTGCAGCCTCCGCCGCCGCTTCAGCCGCTGCAGCCACCGCCCGCGGGA
TTGTGACTGACTTTGCTTTCCTGAGCCCGCTTGCAAGCAGTGCAGCTTCCCGTTCATCCGCCCGCGATGAC
AAGTTGACGGCTCTTTTGGCACAATTGGATTCTTTGACCCGGGAACTTAATGTCGTTTCTCAGCAGCTGTT
GGATCTGCGCCAGCAGGTTTCTGCCCTGAAGGCTTCCTCCCCTCCCAATGCGGTTTAAAACATAAATAAAA
AACCAGACTCTGTTTGGATTTGGATCAAGCAAGTGTCTTGCTGTCTTTATTTAGGGGTTTTGCGCGCGCGG
TAGGCCCGGGACCAGCGGTCTCGGTCGTTGAGGGTCCTGTGTATTTTTCCAGGACGTGGTAAAGGTGACT
CTGGATGTTCAGATACATGGGCATAAGCCCGTCTCTGGGGTGGAGGTAGCACCACTGCAGAGCTTCATGCT
GCGGGGTGGTGTTGTAGATGATCCAGTCGTAGCAGGAGCGCTGGGCGTGGTGCCTAAAAATGTCTTTCAGT
AGCAAGCTGATTGCCAGGGGCAGGCCCTTGGTGTAAGTGTTTACAAAGCGGTTAAGCTGGGATGGGTGCAT
ACGTGGGGATATGAGATGCATCTTGGACTGTATTTTTAGGTTGGCTATGTTCCCAGCCATATCCCTCCGGG
GATTCATGTTGTGCAGAACCACCAGCACAGTGTATCCGGTGCACTTGGGAAATTTGTCATGTAGCTTAGAA
GGAAATGCGTGGAAGAACTTGGAGACGCCCTTGTGACCTCCAAGATTTTCCATGCATTCGTCCATAATGAT
GGCAATGGGCCCACGGGCGGCGGCCTGGGCGAAGATATTTCTGGGATCACTAACGTCATAGTTGTGTTCCA
GGATGAGATCGTCATAGGCCATTTTTACAAAGCGCGGGCGGAGGGTGCCAGACTGCGGTATAATGGTTCCA
TCCGGCCCAGGGGCGTAGTTACCCTCACAGATTTGCATTTCCCACGCTTTGAGTTCAGATGGGGGGATCAT
GTCTACCTGCGGGGCGATGAAGAAAACGGTTTCCGGGGTAGGGGAGATCAGCTGGGAAGAAAGCAGGTTCC
TGAGCAGCTGCGACTTACCGCAGCCGGTGGGCCCGTAAATCACACCTATTACCGGGTGCAACTGGTAGTTA
AGAGAGCTGCAGCTGCCGTCATCCCTGAGCAGGGGGCCCACTTCGTTAAGCATGTCCCTGACTCGCATGTT
TTCCCTGACCAAATCCGCCAGAAGGCGCTCGCCGCCCAGCGATAGCAGTTCTTGCAAGGAAGCAAAGTTTT
TCAACGGTTTGAGACCGTCCGCCGTAGGCATGCTTTTGAGCGTTTGACCAAGCAGTTCCAGGCGGTCCCAC
AGCTCGGTCACCTGCTCTACGGCATCTCGATCCAGCATATCTCCTCGTTTCGCGGGTTGGGGCGGCTTTCG
CTGTACGGCAGTAGTCGGTGCTCGTCCAGACGGGCCAGGGTCATGTCTTTCCACGGGCGCAGGGTCCTCGT
CAGCGTAGTCTGGGTCACGGTGAAGGGGTGCGCTCCGGGCTGCGCGCTGGCCAGGGTGCGCTTGAGGCTGG
TCCTGCTGGTGCTGAAGCGCTGCCGGTCTTCGCCCTGCGCGTCGGCCAGGTAGCATTTGACCATGGTGTCA
TAGTCCAGCCCCTCCGCGGCGTGGCCCTTGGCGCGCAGCTTGCCCTTGGAGGAGGCGCCGCACGAGGGGCA
GTGCAGACTTTTGAGGGCGTAGAGCTTGGGCGCGAGAAATACCGATTCCGGGGAGTAGGCATCCGCGCCGC
AGGCCCCGCAGACGGTCTCGCATTCCACGAGCCAGGTGAGCTCTGGCCGTTCGGGGTCAAAAACCAGGTTT
CCCCCATGCTTTTTGATGCGTTTCTTACCTCTGGTTTCCATGAGCCGGTGTCCACGCTCGGTGACGAAAAG
GCTGTCCGTGTCCCCGTATACAGACTTGAGAGGGAGTTTAAACGAATTCAATAGCTTGTTGCATGGGCGGC
GATATAAAATGCAAGGTGCTGCTCAAAAAATCAGGCAAAGCCTCGCGCAAAAAGAAAGCACATCGTAGTC
ATGCTCATGCAGATAAAGGCAGGTAAGCTCCGGAACCACCACAGAAAAGACACCATTTTCTCTCAAACA
TGTCTGCGGGTTTCTGCATAAACACAAAATAAATAACAAAAAAACATTTAAACATTAGAAGCCTGTCTTA
CAACAGGAAAACAACCCTTATAAGCATAAGACGGACTACGGCCATGCCGGCGTGACCGTAAAAAACTGG
TCACCGTGATTAAAAAGCACCACCGACAGCTCCTCGGTCATGTCCGGAGTCATAATGTAAGACTCGGTAAA
CACATCAGGTTGATTCATCGGTCAGTGCTAAAAAGCGACCGAAATAGCCCGGGGGAATACATACCCGCAGG
CGTAGAGACAACATTACAGCCCCATAGGAGGTATAACAAAATTAATAGGAGAGAAAAACACATAAACACC
TGAAAAACCCTCCTGCCTAGGCAAAATAGCACCCTCCCGCTCCAGAACAACATACAGCGCTTCACAGCGGC
AGCCTAACAGTCAGCCTTACCAGTAAAAAGAAAACCTATTAAAAAACACCACTCGACACGGCACCAGCT
CAATCAGTCACAGTGTAAAAAGGGCCAAGTGCAGAGCGAGTATATATAGGACTAAAAAATGACGTAACGG

Fig. 7 Continued

```
TTAAAGTCCACAAAAAACACCCAGAAAACCGCACGCGAACCTACGCCCAGAAACGAAAGCCAAAAAACCCA
CAACTTCCTCAAATCGTCACTTCCGTTTTCCCACGTTACGTAACTTCCCATTTTAAGAAAACTACAATTCC
CAACACATACAAGTTACTCCGCCCTAAAACCTACGTCACCCGCCCCGTTCCCACGCCCCGCGCCACGTCAC
AAACTCCACCCCCTCATTATCATATTGGCTTCAATCCAAAATAAGGTATATTATTGATGATGTTAATTAAC
ATGCATGGATCCATATGCGGTGTGAAATACCGCACAGATGCGTAAGGAGAAAATACCGCATCAGGCGCTCT
TCCGCTTCCTCGCTCACTGACTCGCTGCGCTCGGTCGTTCGGCTGCGGCAGCGGTATCAGCTCACTCAAA
GGCGGTAATACGGTTATCCACAGAATCAGGGGATAACGCAGGAAAGAACATGTGAGCAAAAGGCCAGCAAA
AGGCCAGGAACCGTAAAAAGGCCGCGTTGCTGGCGTTTTTCCATAGGCTCCGCCCCCCTGACGAGCATCAC
AAAAATCGACGCTCAAGTCAGAGGTGGCGAAACCCGACAGGACTATAAAGATACCAGGCGTTTCCCCCTGG
AAGCTCCCTCGTGCGCTCTCCTGTTCCGACCCTGCCGCTTACCGGATACCTGTCCGCCTTTCTCCCTTCGG
GAAGCGTGGCGCTTTCTCATAGCTCACGCTGTAGGTATCTCAGTTCGGTGTAGGTCGTTCGCTCCAAGCTG
GGCTGTGTGCACGAACCCCCCGTTCAGCCCGACCGCTGCGCCTTATCCGGTAACTATCGTCTTGAGTCCAA
CCCGGTAAGACACGACTTATCGCCACTGGCAGCAGCCACTGGTAACAGGATTAGCAGAGCGAGGTATGTAG
GCGGTGCTACAGAGTTCTTGAAGTGGTGGCCTAACTACGGCTACACTAGAAGGACAGTATTTGGTATCTGC
GCTCTGCTGAAGCCAGTTACCTTCGGAAAAAGAGTTGGTAGCTCTTGATCCGGCAAACAAACCACCGCTGG
TAGCGGTGGTTTTTTTGTTTGCAAGCAGCAGATTACGCGCAGAAAAAAAGGATCTCAAGAAGATCCTTTGA
TCTTTTCTACGGGGTCTGACGCTCAGTGGAACGAAAACTCACGTTAAGGGATTTTGGTCATGAGATTATCA
AAAAGGATCTTCACCTAGATCCTTTTAAATTAAAAATGAAGTTTTAAATCAATCTAAAGTATATATGAGTA
AACTTGGTCTGACAGTTACCAATGCTTAATCAGTGAGGCACCTATCTCAGCGATCTGTCTATTTCGTTCAT
CCATAGTTGCCTGACTCCCCGTCGTGTAGATAACTACGATACGGGAGGGCTTACCATCTGGCCCCAGTGCT
GCAATGATACCGCGAGACCCACGCTCACCGGCTCCAGATTTATCAGCAATAAACCAGCCAGCCGGAAGGGC
CGAGCGCAGAAGTGGTCCTGCAACTTTATCCGCCTCCATCCAGTCTATTAATTGTTGCCGGGAAGCTAGAG
TAAGTAGTTCGCCAGTTAATAGTTTGCGCAACGTTGTTGCCATTGCTGCAGCCATGAGATTATCAAAAAGG
ATCTTCACCTAGATCCTTTTCACGTAGAAAGCCAGTCCGCAGAAACGGTGCTGACCCCGGATGAATGTCAG
CTACTGGGCTATCTGGACAAGGGAAAACGCAAGCGCAAAGAGAAAGCAGGTAGCTTGCAGTGGGCTTACAT
GGCGATAGCTAGACTGGGCGGTTTTATGGACAGCAAGCGAACCGGAATTGCCAGCTGGGGCGCCCTCTGGT
AAGGTTGGGAAGCCCTGCAAAGTAAACTGGATGGCTTTCTTGCCGCCAAGGATCTGATGGCGCAGGGGATC
AAGCTCTGATCAAGAGACAGGATGAGGATCGTTTCGCATGATTGAACAAGATGGATTGCACGCAGGTTCTC
CGGCCGCTTGGGTGGAGAGGCTATTCGGCTATGACTGGGCACAACAGACAATCGGCTGCTCTGATGCCGCC
GTGTTCCGGCTGTCAGCGCAGGGGCGCCCGGTTCTTTTGTCAAGACCGACCTGTCCGGTGCCCTGAATGA
ACTGCAAGACGAGGCAGCGCGGCTATCGTGGCTGGCCACGACGGGCGTTCCTTGCGCAGCTGTGCTCGACG
TTGTCACTGAAGCGGGAAGGGACTGGCTGCTATTGGGCGAAGTGCCGGGGCAGGATCTCCTGTCATCTCAC
CTTGCTCCTGCCGAGAAAGTATCCATCATGGCTGATGCAATGCGGCGGCTGCATACGCTTGATCCGGCTAC
CTGCCCATTCGACCACCAAGCGAAACATCGCATCGAGCGAGCACGTACTCGGATGGAAGCCGGTCTTGTCG
ATCAGGATGATCTGGACGAAGAGCATCAGGGGCTCGCGCCAGCCGAACTGTTCGCCAGGCTCAAGGCGAGC
ATGCCCGACGGCGAGGATCTCGTCGTGACCCATGGCGATGCCTGCTTGCCGAATATCATGGTGGAAAATGG
CCGCTTTTCTGGATTCATCGACTGTGGCCGGCTGGGTGTGGCGGACCGCTATCAGGACATAGCGTTGGCTA
CCCGTGATATTGCTGAAGAGCTTGGCGGCGAATGGGCTGACCGCTTCCTCGTGCTTTACGGTATCGCCGCT
CCCGATTCGCAGCGCATCGCCTTCTATCGCCTTCTTGACGAGTTCTTCTGAATTTTGTTAAAATTTTGTT
AAATCAGCTCATTTTTTAACCAATAGGCCGAAATCGGCAACATCCCTTATAAATCAAAAGAATAGACCGCG
ATAGGGTTGAGTGTTGTTCCAGTTTGGAACAAGAGTCCACTATTAAAGAACGTGGACTCCAACGTCAAAGG
GCGAAAAACCGTCTATCAGGGCGATGGCCCACTACGTGAACCATCACCCAAATCAAGTTTTTTGCGGTCGA
GGTGCCGTAAAGCTCTAAATCGGAACCCTAAAGGGAGCCCCCGATTTAGAGCTTGACGGGGAAAGCCGGCG
AACGTGGCGAGAAAGGAAGGGAAGAAAGCGAAAGGAGCGGGCGCTAGGGCGCTGGCAAGTGTAGCGGTCAC
GCTGCGCGTAACCACCACACCCGCGCGCTTAATGCGCCGCTACAGGGCGCGTCCATTCGCCATTCAGGATC
GAATTAATTCTTAATTAA
```

Fig. 8                >pGene/V5-His 7698bp
CCGAGCTCTTACGCGGGTCGAAGCGGAGTACTGTCCTCCGAGTGGAGTACTGTCCTCCGAGCGGAGTACTG
TCCTCCGAGTCGAGGGTCGAAGCGGAGTACTGTCCTCCGAGTGGAGTACTGTCCTCCGAGCGGAGTACTGT
CCTCCGAGTCGACTCTAGAGGGTATATAATGGATCTCGAGATATCGGAGCTCGTTTAGTGAACCGTCAGAT
CGCCTGGAGACGCCATCCACGCTGTTTTGACCTCCATAGAAGACACCGGGACCGATCCAGCCTCCGCGGCC
GGGAACGGTGCATTGGAACGCGCATTCCCCGTGTTAATTAACAGGTAAGTGTCTTCCTCCTGTTTCCTTCC
CCTGCTATTCTGCTCAACCTTCCTATCAGAAACTGCAGTATCTGTATTTTGCTAGCAGTAATACTAACGG
TTCTTTTTTTCTCTTCACAGGCCACCAAGCTTGGTACCGAGCTCGGATCCACTAGTCCAGTGTGGTGGAAT
TCTGCAGATCGAAACGATGATAGATCCCGTCGTTTTACAACGTCGTGACTGGGAAAACCCTGGCGTTACCC
AACTTAATCGCCTTGCAGCACATCCCCCTTTCGCCAGCTGGCGTAATAGCGAAGAGGCCCGCACCGATCGC
CCTTCCCAACAGTTGCGCAGCCTGAATGGCGAATGGCGCTTTGCCTGGTTTCCGGCACCAGAAGCGGTGCC
GGAAAGCTGGCTGGAGTGCGATCTTCCTGAGGCCGATACTGTCGTCGTCCCCTCAAACTGGCAGATGCACG
GTTACGATGCGCCCATCTACACCAACGTAACCTATCCCATTACGGTCAATCCGCCGTTTGTTCCCACGGAG
AATCCGACGGGTTGTTACTCGCTCACATTTAATGTTGATGAAAGCTGGCTACAGGAAGGCCAGACGCGAAT
TATTTTTGATGGCGTTAACTCGGCGTTTCATCTGTGGTGCAACGGGCGCTGGGTCGGTTACGGCCAGGACA
GTCGTTTGCCGTCTGAATTTGACCTGAGCGCATTTTTACGCGCCGGAGAAAACCGCCTCGCGGTGATGGTG
CTGCGTTGGAGTGACGGCAGTTATCTGGAAGATCAGGATATGTGGCGGATGAGCGGCATTTTCCGTGACGT
CTCGTTGCTGCATAAACCGACTACACAAATCAGCGATTTCCATGTTGCCACTCGCTTTAATGATGATTTCA
GCCGCGCTGTACTGGAGGCTGAAGTTCAGATGTGCGGCGAGTTGCGTGACTACCTACGGGTAACAGTTTCT
TTATGGCAGGGTGAAACGCAGGTCGCCAGCGGCACCGCGCCTTTCGGCGGTGAAATTATCGATGAGCGTGG
TGGTTATGCCGATCGCGTCACACTACGTCTGAACGTCGAAAACCCGAAACTGTGGAGCGCCGAAATCCCGA
ATCTCTATCGTGCGGTGGTTGAACTGCACACCGCCGACGGCACGCTGATTGAAGCAGAAGCCTGCGATGTC
GGTTTCCGCGAGGTGCGGATTGAAAATGGTCTGCTGCTGCTGAACGGCAAGCCGTTGCTGATTCGAGGCGT
TAACCGTCACGAGCATCATCCTCTGCATGGTCAGGTCATGGATGAGCAGACGATGGTGCAGGATATCCTGC
TGATGAAGCAGAACAACTTTAACGCCGTGCGCTGTTCGCATTATCCGAACCATCCGCTGTGGTACACGCTG
TGCGACCGCTACGGCCTGTATGTGGTGGATGAAGCCAATATTGAAACCCACGGCATGGTGCCAATGAATCG
TCTGACCGATGATCCGCGCTGGCTACCGGCGATGAGCGAACGCGTAACGCGAATGGTGCAGCGCGATCGTA
ATCACCCGAGTGTGATCATCTGGTCGCTGGGGAATGAATCAGGCCACGGCGCTAATCACGACGCGCTGTAT
CGCTGGATCAAATCTGTCGATCCTTCCCGCCCGGTGCAGTATGAAGGCGGCGGAGCCGACACCACGGCCAC
CGATATTATTTGCCCGATGTACGCGCGCGTGGATGAAGACCAGCCCTTCCCGGCTGTGCCGAAATGGTCCA
TCAAAAAATGGCTTTCGCTACCTGGAGAGACGCGCCCGCTGATCCTTTGCGAATACGCCCACGCGATGGGT
AACAGTCTTGGCGGTTTCGCTAAATACTGGCAGGCGTTTCGTCAGTATCCCCGTTTACAGGGCGGCTTCGT
CTGGGACTGGGTGGATCAGTCGCTGATTAAATATGATGAAAACGGCAACCCGTGGTCGGCTTACGGCGGTG
ATTTTGGCGATACGCCGAACGATCGCCAGTTCTGTATGAACGGTCTGGTCTTTGCCGACCGCACGCCGCAT
CCAGCGCTGACGGAAGCAAAACACCAGCAGCAGTTTTTCCAGTTCCGTTTATCCGGGCAAACCATCGAAGT
GACCAGCGAATACCTGTTCCGTCATAGCGATAACGAGCTCCTGCACTGGATGGTGGCGCTGGATGGTAAGC
CGCTGGCAAGCGGTGAAGTGCCTCTGGATGTCGCTCCACAAGGTAAACAGTTGATTGAACTGCCTGAACTA
CCGCAGCCGGAGAGCGCCGGGCAACTCTGGCTCACAGTACGCGTAGTGCAACCGAACGCGACCGCATGGTC
AGAAGCCGGGCACATCAGCGCCTGGCAGCAGTGGCGTCTGGCGGAAAACCTCAGTGTGACGCTCCCCGCCG
CGTCCCACGCCATCCCGCATCTGACCACCAGCGAAATGGATTTTTGCATCGAGCTGGGTAATAAGCGTTGG
CAATTTAACCGCCAGTCAGGCTTTCTTTCACAGATGTGGATTGGCGATAAAAAACAACTGCTGACGCCGCT
GCGCGATCAGTTCACCCGTGCACCGCTGGATAACGACATTGGCGTAAGTGAAGCGACCCGCATTGACCCTA
ACGCCTGGGTCGAACGCTGGAAGGCGGCGGGCCATTACCAGGCCGAAGCAGCGTTGTTGCAGTGCACGGCA
GATACACTTGCTGATGCGGTGCTGATTACGACCGCTCACGCGTGGCAGCATCAGGGGAAAACCTTATTTAT
CAGCCGGAAAACCTACCGGATTGATGGTAGTGGTCAAATGGCGATTACCGTTGATGTTGAAGTGGCGAGCG
ATACACCGCATCCGGCGCGGATTGGCCTGAACTGCCAGCTGGCGCAGGTAGCAGAGCGGGTAAACTGGCTC
GGATTAGGGCCGCAAGAAAACTATCCCGACCGCCTTACTGCCGCCTGTTTTGACCGCTGGGATCTGCCATT

Fig. 8 Continued

```
GTCAGACATGTATACCCCGTACGTCTTCCCGAGCGAAAACGGTCTGCGCTGCGGGACGCGCGAATTGAATT
ATGGCCCACACCAGTGGCGCGGCGACTTCCAGTTCAACATCAGCCGCTACAGTCAACAGCAACTGATGGAA
ACCAGCCATCGCCATCTGCTGCACGCGGAAGAAGGCACATGGCTGAATATCGACGGTTTCCATATGGGGAT
TGGTGGCGACGACTCCTGGAGCCCGTCAGTATCGGCGGAATTCCAGCTGAGCGCCGGTCGCTACCATTACC
AGTTGGTCTGGTGTCAAAAAGCGGCCGCTCGAGGTCACCCATTCGAAGGTAAGCCTATCCCTAACCCTCTC
CTCGGTCTCGATTCTACGCGTACCGGTCATCATCACCATCACCATTGAGTTTAAACCCGCTGATCAGCCTC
GACTGTGCCTTCTAGTTGCCAGCCATCTGTTGTTTGCCCCTCCCCCGTGCCTTCCTTGACCCTGGAAGGTG
CCACTCCCACTGTCCTTTCCTAATAAAATGAGGAAATTGCATCGCATTGTCTGAGTAGGTGTCATTCTATT
CTGGGGGGTGGGGTGGGGCAGGACAGCAAGGGGGAGGATTGGGAAGACAATAGCAGGCATGCTGGGGATGC
GGTGGGCTCTATGGCTTCTGAGGCGGAAAGAACCAGCTGGGGCTCTAGGGGGTATCCCCACGCGCCCTGTA
GCGGCGCATTAAGCGCGGCGGGTGTGGTGGTTACGCGCAGCGTGACCGCTACACTTGCCAGCGCCCTAGCG
CCCGCTCCTTTCGCTTTCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAAACTTGATTAGGGTGATG
GTTCACGTAGTGGGCCATCGCCCTGATAGACGGTTTTCGCCCTTTGACGTTGGAGTCCACGTTCTTTAAT
AGTGGACTCTTGTTCCAAACTGGAACAACACTCAACCCTATCTCGGTCTATTCTTTTGATTTATAAGGGAT
TTTGCCGATTTCGGCCTATTGGTTAAAAAATGAGCTGATTTAACAAAAATTTAACGCGAATTAATTCTGTG
GAATGTGTGTCAGTTAGGGTGTGGAAAGTCCCCAGGCTCCCCAGCAGGCAGAAGTATGCAAAGCATGCATC
TCAATTAGTCAGCAACCAGGTGTGGAAAGTCCCCAGGCTCCCCAGCAGGCAGAAGTATGCAAAGCATGCAT
CTCAATTAGTCAGCAACCATAGTCCCGCCCCTAACTCCGCCCATCCCGCCCCTAACTCCGCCCAGTTCCGC
CCATTCTCCGCCCCATGGCTGACTAATTTTTTTTATTTATGCAGAGGCCGAGGCCGCCTCTGCCTCTGAGC
TATTCCAGAAGTAGTGAGGAGGCTTTTTTGGAGGCCTAGGCTTTTGCAAAAAGCTCCCGGGAGCTTGTATA
TCCATTTTCGGATCTGATCAGCACGTGTTGACAATTAATCATCGGCATAGTATATCGGCATAGTATAATAC
GACAAGGTGAGGAACTAAACCATGGCCAAGTTGACCAGTGCCGTTCCGGTGCTCACCGCGCGCGACGTCGC
CGGAGCGGTCGAGTTCTGGACCGACCGGCTCGGGTTCTCCCGGGACTTCGTGGAGGACGACTTCGCCGGTG
TGGTCCGGGACGACGTGACCCTGTTCATCAGCGCGGTCCAGGACCAGGTGGTGCCGGACAACACCCTGGCC
TGGGTGTGGGTGCGCGGCCTGGACGAGCTGTACGCCGAGTGGTCGGAGGTCGTGTCCACGAACTTCCGGGA
CGCCTCCGGGCCGGCCATGACCGAGATCGGCGAGCAGCCGTGGGGCGGGAGTTCGCCCTGCGCGACCCGG
CCGGCAACTGCGTGCACTTCGTGGCCGAGGAGCAGGACTGACACGTGCTACGAGATTTCGATTCCACCGCC
GCCTTCTATGAAAGGTTGGGCTTCGGAATCGTTTTCCGGGACGCCGGCTGGATGATCCTCCAGCGCGGGGA
TCTCATGCTGGAGTTCTTCGCCCACCCCAACTTGTTTATTGCAGCTTATAATGGTTACAAATAAAGCAATA
GCATCACAAATTTCACAAATAAAGCATTTTTTCACTGCATTCTAGTTGTGGTTTGTCCAAACTCATCAAT
GTATCTTATCATGTCTGTATACCGTCGACATCTAGCTAGAGCTTGGCGTAATCATGGTCATAGCTGTTTCC
TGTGTGAAATTGTTATCCGCTCACAATTCCACACAACATACGAGCCGGAAGCATAAAGTGTAAAGCCTGGG
GTGCCTAATGAGTGAGCTAACTCACATTAATTGCGTTGCGCTCACTGCCCGCTTTCCAGTCGGGAAACCTG
TCGTGCCAGCTGCATTAATGAATCGGCCAACGCGCGGGGAGAGGCGGTTTGCGTATTGGGCGCTCTTCCGC
TTCCTCGCTCACTGACTCGCTGCGCTCGGTCGTTCGGCTGCGGCGAGCGGTATCAGCTCACTCAAAGGCGG
TAATACGGTTATCCACAGAATCAGGGGATAACGCAGGAAAGAACATGTGAGCAAAAGGCCAGCAAAAGGCC
AGGAACCGTAAAAAGGCCGCGTTGCTGGCGTTTTTCCATAGGCTCCGCCCCCCTGACGAGCATCACAAAAA
TCGACGCTCAAGTCAGAGGTGGCGAAACCCGACAGGACTATAAAGATACCAGGCGTTTCCCCCTGGAAGCT
CCCTCGTGCGCTCTCCTGTTCCGACCCTGCCGCTTACCGGATACCTGTCCGCCTTTCTCCCTTCGGGAAGC
GTGGCGCTTTCTCATAGCTCACGCTGTAGGTATCTCAGTTCGGTGTAGGTCGTTCGCTCCAAGCTGGGCTG
TGTGCACGAACCCCCCGTTCAGCCCGACCGCTGCGCCTTATCCGGTAACTATCGTCTTGAGTCCAACCCGG
TAAGACACGACTTATCGCCACTGGCAGCAGCCACTGGTAACAGGATTAGCAGAGCGAGGTATGTAGGCGGT
GCTACAGAGTTCTTGAAGTGGTGGCCTAACTACGGCTACACTAGAAGAACAGTATTTGGTATCTGCGCTCT
GCTGAAGCCAGTTACCTTCGGAAAAAGAGTTGGTAGCTCTTGATCCGGCAAACAAACCACCGCTGGTAGCG
GTTTTTTTGTTTGCAAGCAGCAGATTACGCGCAGAAAAAAAGGATCTCAAGAAGATCCTTTGATCTTTTCT
ACGGGGTCTGACGCTCAGTGGAACGAAAACTCACGTTAAGGGATTTTGGTCATGAGATTATCAAAAGGAT
```

Fig. 8 Continued

```
CTTCACCTAGATCCTTTTAAATTAAAAATGAAGTTTTAAATCAATCTAAAGTATATATGAGTAAACTTGGT
CTGACAGTTACCAATGCTTAATCAGTGAGGCACCTATCTCAGCGATCTGTCTATTTCGTTCATCCATAGTT
GCCTGACTCCCCGTCGCGTAGATAACTACGATACGGGAGGGCTTACCATCTGGCCCCAGTGCTGCAATGAT
ACCGCGAGACCCACGCTCACCGGCTCCAGATTTATCAGCAATAAACCAGCCAGCCGGAAGGGCCGAGCGCA
GAAGTGGTCCTGCAACTTTATCCGCCTCCATCCAGTCTATTAATTGTTGCCGGGAAGCTAGAGTAAGTAGT
TCGCCAGTTAATAGTTTGCGCAACGTTGTTGCCATTGCTACAGGCATCGTGGTGTCACGCTCGTCGTTTGG
TATGGCTTCATTCAGCTCCGGTTCCCAACGATCAAGGCGAGTTACATGATCCCCATGTTGTGCAAAAAAG
CGGTTAGCTCCTTCGGTCCTCCGATCGTTGTCAGAAGTAAGTTGGCCGCAGTGTTATCACTCATGGTTATG
GCAGCACTGCATAATTCTCTTACTGTCATGCCATCCGTAAGATGCTTTTCTGTGACTGGTGAGTACTCAAC
CAAGTCATTCTGAGAATAGTGTATGCGGCGACCGAGTTGCTCTTGCCCGGCGTCAATACGGGATAATACCG
CGCCACATAGCAGAACTTTAAAAGTGCTCATCATTGGAAAACGTTCTTCGGGGCGAAAACTCTCAAGGATC
TTACCGCTGTTGAGATCCAGTTCGATGTAACCCACTCGTGCACCCAACTGATCTTCAGCATCTTTTACTTT
CACCAGCGTTTCTGGGTGAGCAAAAACAGGAAGGCAAAATGCCGCAAAAAAGGGAATAAGGGCGACACGGA
AATGTTGAATACTCATACTCTTCCTTTTTCAATATTATTGAAGCATTTATCAGGGTTATTGTCTCATGAGC
GGATACATATTTGAATGTATTTAGAAAAATAAACAAATAGGGGTTCCGCGCACATTTCCCCGAAAAGTGCC
ACCTGACGTCGACGGATCGGGAGATCGTA
```

Fig. 9  >pXC1 9905bp

```
CCCTTCCAGCTCTCTGCCCCTTTTGGATTGAAGCCAATATGATAATGAGGGGGTGGAGTTTGTGACGTGGC
GCGGGGCGTGGGAACGGGGCGGGTGACGTAGTAGTGTGGCGGAAGTGTGATGTTGCAAGTGTGGCGGAACA
CATGTAAGCGACGGATGTGGCAAAAGTGACGTTTTTGGTGTGCGCCGGTGTACACAGGAAGTGACAATTTT
CGCGCGGTTTTAGGCGGATGTTGTAGTAAATTTGGGCGTAACCGAGTAAGATTTGGCCATTTTCGCGGGAA
AACTGAATAAGAGGAAGTGAAATCTGAATAATTTTGTGTTACTCATAGCGCGTAATATTTGTCTAGGGCCG
CGGGGACTTTGACCGTTTACGTGGAGACTCGCCCAGGTGTTTTTCTCAGGTGTTTTCCGCGTTCCGGGTCA
AAGTTGGCGTTTTATTATTATAGTCAGCTGACGTGTAGTGTATTTATACCCGGTGAGTTCCTCAAGAGGCC
ACTCTTGAGTGCCAGCGAGTAGAGTTTTCTCCTCCGAGCCGCTCCGACACCGGGACTGAAAATGAGACATA
TTATCTGCCACGGAGGTGTTATTACCGAAGAAATGGCCGCCAGTCTTTTGGACCAGCTGATCGAAGAGGTA
CTGGCTGATAATCTTCCACCTCCTAGCCATTTTGAACCACCTACCCTTCACGAACTGTATGATTTAGACGT
GACGGCCCCCGAAGATCCCAACGAGGAGGCGGTTTCGCAGATTTTTCCCGACTCTGTAATGTTGGCGGTGC
AGGAAGGGATTGACTTACTCACTTTTCCGCCGGCGCCCGGTTCTCCGGAGCCGCCTCACCTTTCCGGCAG
CCCGAGCAGCCGGAGCAGAGAGCCTTGGGTCCGGTTTCTATGCCAAACCTTGTACCGGAGGTGATCGATCT
TACCTGCCACGAGGCTGGCTTTCCACCCAGTGACGACGAGGATGAAGAGGGTGAGGAGTTTGTGTTAGATT
ATGTGGAGCACCCCGGGCACGGTTGCAGGTCTTGTCATTATCACCGGAGGAATACGGGGGACCCAGATATT
ATGTGTTCGCTTTGCTATATGAGGACCTGTGGCATGTTTGTCTACAGTAAGTGAAAATTATGGGCAGTGGG
TGATAGAGTGGTGGGTTTGGTGTGGTAATTTTTTTTTTAATTTTTACAGTTTTGTGGTTTAAAGAATTTTG
TATTGTGATTTTTTTAAAAGGTCCTGTGTCTGAACCTGAGCCTGAGCCCGAGCCAGAACCGGAGCCTGCAA
GACCTACCCGCCGTCCTAAAATGGCGCCTGCTATCCTGAGACGCCCGACATCACCTGTGTCTAGAGAATGC
AATAGTAGTACGGATAGCTGTGACTCCGGTCCTTCTAACACACCTCCTGAGATACACCCGGTGGTCCCGCT
GTGCCCCATTAAACCAGTTGCCGTGAGAGTTGGTGGGCGTCGCCAGGCTGTGGAATGTATCGAGGACTTGC
TTAACGAGCCTGGGCAACCTTTGGACTTGAGCTGTAAACGCCCCAGGCCATAAGGTGTAAACCTGTGATTG
CGTGTGTGGTTAACGCCTTTGTTTGCTGAATGAGTTGATGTAAGTTTAATAAAGGGTGAGATAATGTTTAA
CTTGCATGGCGTGTTAAATGGGGCGGGGCTTAAAGGGTATATAATGCGCCGTGGGCTAATCTTGGTTACAT
CTGACCTCATGGAGGCTTGGGAGTGTTTGGAAGATTTTCTGCTGTGCGTAACTTGCTGGAACAGAGCTCT
AACAGTACCTCTTGGTTTTGGAGGTTTCTGTGGGGCTCATCCCAGGCAAAGTTAGTCTGCAGAATTAAGGA
GGATTACAAGTGGGAATTTGAAGAGCTTTTGAAATCCTGTGGTGAGCTGTTTGATTCTTTGAATCTGGGTC
ACCAGGCGCTTTTCCAAGAGAAGGTCATCAAGACTTTGGATTTTTCCACACCGGGGCGCGCTGCGGCTGCT
GTTGCTTTTTTGAGTTTTATAAAGGATAAATGGAGCGAAGAAACCCATCTGAGCGGGGGGTACCTGCTGGA
TTTTCTGGCCATGCATCTGTGGAGAGCGGTTGTGAGACACAAGAATCGCCTGCTACTGTTGTCTTCCGTCC
GCCCGGCGATAATACCGACGGAGGAGCAGCAGCAGCAGCAGGAGGAAGCCAGGCGGCGGCGGCAGGAGCAG
AGCCCATGGAACCCGAGAGCCGGCCTGGACCCTCGGGAATGAATGTTGTACAGGTGGCTGAACTGTATCCA
GAACTGAGACGCATTTTGACAATTACAGAGGATGGGCAGGGGCTAAAGGGGGTAAAGAGGGAGCGGGGGGC
TTGTGAGGCTACAGAGGAGGCTAGGAATCTAGCTTTTAGCTTAATGACCAGACACCGTCCTGAGTGTATTA
CTTTTCAACAGATCAAGGATAATTGCGCTAATGAGCTTGATCTGCTGGCGCAGAAGTATTCCATAGAGCAG
CTGACCACTTACTGGCTGCAGCCAGGGGATGATTTTGAGGAGGCTATTAGGGTATATGCAAAGGTGGCACT
TAGGCCAGATTGCAAGTACAAGATCAGCAAACTTGTAAATATCAGGAATTGTTGCTACATTTCTGGGAACG
GGGCCCGAGGTGGAGATAGATACGGAGGATAGGGTGGCCTTTAGATGTAGCATGATAAATATGTGGCCGGGG
GTGCTTGGCATGGACGGGGTGGTTATTATGAATGTAAGGTTTACTGGCCCCAATTTTAGCGGTACGGTTTT
CCTGGCCAATACCAACCTTATCCTACACGGTGTAAGCTTCATGGGTTTAACAATACCTGTGTGGAAGCCT
GGACCGATGTAAGGGTTCGGGGCTGTGCCTTTTACTGCTGCTGGAAGGGGGTGGTGTGTCGCCCCAAAAGC
AGGGCTTCAATTAAGAAATGCCTCTTTGAAAGGTGTACCTTGGGTATCCTGTCTGAGGGTAACTCCAGGGT
GCGCCACAATGTGGCCTCCGACTGTGGTTGCTTCATGCTAGTGAAAAGCGTGGCTGTGATTAAGCATAACA
TGGTATGTGGCAACTGCGAGGACAGGGCCTCTCAGATGCTGACCTGCTCGGACGGCAACTGTCACCTGCTG
AAGACCATTCACGTAGCCAGCCACTCTCGCAAGGCCTGGCCAGTGTTTGAGCATAACATACTGACCCGCTG
TTCCTTGCATTTGGGTAACAGGAGGGGGTGTTCCTACCTTACCAATGCAATTTGAGTCACACTAAGATAT
TGCTTGAGCCCGAGAGCATGTCCAAGGTGAACCTGAACGGGGTGTTTGACATGACCATGAAGATCTGGAAG
GTGCTGAGGTACGATGAGACCCGCACCAGGTGCAGACCCTGCGAGTGTGGCGGTAAACATATTAGGAACCA
```

Fig. 9 Continued

```
GCCTGTGATGCTGGATGTGACCGAGGAGCTGAGGCCCGATCACTTGGTGCTGGCCTGCACCCGCGCTGAGT
TTGGCTCTAGCGATGAAGATACAGATTGAGGTACTGAAATGTGTGGGCGTGGCTTAAGGGTGGGAAAGAAT
ATATAAGGTGGGGGTCTTATGTAGTTTTGTATCTGTTTTGCAGCAGCCGCCGCCGCCATGAGCACCAACTC
GTTTGATGGAAGCATTGTGAGCTCATATTTGACAACGCGCATGCCCCCATGGGCCGGGGTGCGTCAGAATG
TGATGGGCTCCAGCATTGATGGTCGCCCCGTCCTGCCCGCAAACTCTACTACCTTGACCTACGAGACCGTG
TCTGGAACGCCGTTGGAGACTGCAGCCTCCGCCGCCGCTTCAGCCGCTGCAGCCACCGCCCGCGGGATTGT
GACTGACTTTGCTTTCCTGAGCCCGCTTGCAAGCAGTGCAGCTTCCCGTTCATCCGCCCGCGATGACAAGT
TGACGGCTCTTTTGGCACAATTGGATTCTTTGACCCGGGAACTTAATGTCGTTTCTCAGCAGCTGTTGGAT
CTGCGCCAGCAGGTTTCTGCCCTGAAGGCTTCCTCCCCTCCCAATGCGGTTTAAAACATAAATAAAAAACC
AGACTCTGTTTGGATTTGGATCAAGCAAGTGTCTTGCTGTCTTTATTTAGGGGTTTTGCGCGCGCGGTAGG
CCCGGGACCAGCGGTCTCGGTCGTTGAGGGTCCTGTGTATTTTTTCCAGGACGTGGTAAAGGTGACTCTGG
ATGTTCAGATACATGGGCATAAGCCCGTCTCTGGGGTGGAGGTAGCACCACTGCAGAGCTTCATGCTGCGG
GGTGGTGTTGTAGATGATCCAGTCGTAGCAGGAGCGCTGGGCGTGGTGCCTAAAAATGTCTTTCAGTAGCA
AGCTGATTGCCAGGGGCAGGCCCTTGGTGTAAGTGTTTACAAAGCGGTTAAGCTGGGATGGGTGCATACGT
GGGGATATGAGATGCATCTTGGACTGTATTTTAGGTTGGCTATGTTCCAGCCATATCCCTCCGGGGATT
CATGTTGTGCAGAACCACCAGCACAGTGTATCCGGTGCACTTGGGAAATTTGTCATGTAGCTTAGAAGGAA
ATGCGTGGAAGAACTTGGAGACGCCCTTGTGACCTCCAAGATTTTCCATGCATTCGTCCATAATGATGGCA
ATGGGCCCACGGGCGGCGGCCTGGGCGAAGATATTTCTGGGATCACTAACGTCATAGTTGTGTTCCAGGAT
GAGATCGTCATAGGCCATTTTTACAAAGCGCGGGCGGAGGGTGCCAGACTGCGGTATAATGGTTCCATCCG
GCCCAGGGGCGTAGTTACCCTCACAGATTTGCATTTCCCACGCTTTGAGTTCAGATGGGGGATCATGTCT
ACCTGCGGGGCGATGAAGAAAACGGTTTCCGGGGTAGGGGAGATCAGCTGGGAAGAAAGCAGGTTCCTGAG
CAGCTGCGACTTACCGCAGCCGGTGGGCCCGTAAATCACACCTATTACCGGGTGCAACTGGTAGTTAAGAG
AGCTGCAGCTGCCGTCATCCCTGAGCAGGGGGGCCACTTCGTTAAGCATGTCCCTGACTCGCATGTTTTCC
CTGACCAAATCCGCCAGAAGGCGCTCGCCGCCCAGCGATAGCAGTTCTTGCAAGGAAGCAAAGTTTTTCAA
CGGTTTGAGACCGTCCGCCGTAGGCATGCTTTTGAGCGTTTGACCAAGCAGTTCCAGGCGGTCCCACAGCT
CGGTCACCTGCTCTACGGCATCTCGATCCAGCATATCTCCTCGTTTCGCGGGTTGGGGCGGCTTTCGCTGT
ACGGCAGTAGTCGGTGCTCGTCCAGACGGGCCAGGGTCATGTCTTTCCACGGGCGCAGGGTCCTCGTCAGC
GTAGTCTGGGTCACGGTGAAGGGGTGCGCTCCGGGCTGCGCGCTGGCCAGGGTGCGCTTGAGGCTGGTCCT
GCTGGTGCTGAAGCGCTGCCGGTCTTCGCCCTGCGCGTCGGCCAGGTAGCATTTGACCATGGTGTCATAGT
CCAGCCCCTCCGCGGCGTGGCCCTTGGCGCGCAGCTTGCCCTTGGAGGAGGCGCCGCACGAGGGCAGTGC
AGACTTTTGAGGGCGTAGAGCTTGGGCGCGAGAAATACCGATTCCGGGGAGTAGGCATCCGCGCCGCAGGC
CCCGCAGACGGTCTCGCATTCCACGAGCCAGGTGAGCTCTGGCCGTTCGGGGTCAAAAACCAGGTTTCCCC
CATGCTTTTTGATGCGTTTCTTACCTCTGGTTTCCATGAGCCGGTGTCCACGCTCGGTGACGAAAGGCTG
TCCGTGTCCCCGTATACAGACTTGAGAGGCCTGTCCTCGGCCTGTCCTCGACCGATGCCCTTGAGAGCCTT
CAACCCAGTCAGCTCCTTCCGGTGGGCGCGGGGCATGACTATCGTCGCCGCACTTATGACTGTCTTCTTTA
TCATGCAACTCGTAGGACAGGTGCCGGCAGCGCTCTGGGTCATTTTCGGCGAGGACCGCTTTCGCTGGAGC
GCGACGATGATCGGCCTGTCGCTTGCGGTATTCGGAATCTTGCACGCCCTCGCTCAAGCCTTCGTCACTGG
TCCCGCCACCAAACGTTTCGGCGAGAAGCAGGCCATTATCGCCGGCATGGCGGCCGACGCGCTGGGCTACG
TCTTGCTGGCGTTCGCGACGCGAGGCTGGATGGCCTTCCCCATTATGATTCTTCTCGCTTCCGGCGGCATC
GGGATGCCCGCGTTGCAGGCCATGCTGTCCAGGCAGGTAGATGACGACCATCAGGGACAGCTTCAAGGATC
GCTCGCGGCTCTTACCAGCCTAACTTCGATCACTGGACCGCTGATCGTCACGGCGATTTATGCCGCCTCGG
CGAGCACATGGAACGGGTTGGCATGGATTGTAGGCGCCGCCCTATACCTTGTCTGCCTCCCCGCGTTGCGT
CGCGGTGCATGGAGCCGGGCCACCTCGACCTGAATGGAAGCGGCGGCACCTCGCTAACGGATTCACCACT
CCAAGAATTGGAGCCAATCAATTCTTGCGGAGAACTGTGAATGCGCAAACCAACCCTTGGCAGAACATATC
CATCGCGTCCGCCATCTCCAGCAGCCGCACGCGGCGCATCTCGGGCAGCGTTGGGTCCTGGCCACGGGTGC
GCATGATCGTGCTCCTGTCGTTGAGGACCCGGCTAGCTGGCGGGGTTGCCTTACTGGTTAGCAGAATGAA
TCACCGATACGCGAGCGAACGTGAAGCGACTGCTGCTGCAAAACGTCTGCGACCTGAGCAACAACATGAAT
```

Fig. 9 Continued

```
GGTCTTCGGTTTCCGTGTTTCGTAAAGTCTGGAAACGCGGAAGTCAGCGCCCTGCACCATTATGTTCCGGA
TCTGCATCGCAGGATGCTGCTGGCTACCCTGTGGAACACCTACATCTGTATTAACGAAGCGCTGGCATTGA
CCCTGAGTGATTTTTCTCTGGTCCCGCCGCATCCATACCGCCAGTTGTTTACCCTCACAACGTTCCAGTAA
CCGGGCATGTTCATCATCAGTAACCCGTATCGTGAGCATCCTCTCTCGTTTCATCGGTATCATTACCCCCA
TGAACAGAAATCCCCCTTACACGGAGGCATCAGTGACCAAACAGGAAAAAACCGCCCTTAACATGGCCCGC
TTTATCAGAAGCCAGACATTAACGCTTCTGGAGAAACTCAACGAGCTGGACGCGGATGAACAGGCAGACAT
CTGTGAATCGCTTCACGACCACGCTGATGAGCTTTACCGCAGCTGCCTCGCGCGTTTCGGTGATGACGGTG
AAAACCTCTGACACATGCAGCTCCCGGAGACGGTCACAGCTTGTCTGTAAGCGGATGCCGGGAGCAGACAA
GCCCGTCAGGGCGCGTCAGCGGGTGTTGGCGGGTGTCGGGGCGCAGCCATGACCCAGTCACGTAGCGATAG
CGGAGTGTATACTGGCTTAACTATGCGGCATCAGAGCAGATTGTACTGAGAGTGCACCATATGCGGTGTGA
AATACCGCACAGATGCGTAAGGAGAAAATACCGCATCAGGCGCTCTTCCGCTTCCTCGCTCACTGACTCGC
TGCGCTCGGTCGTTCGGCTGCGGCGAGCGGTATCAGCTCACTCAAAGGCGGTAATACGGTTATCCACAGAA
TCAGGGGATAACGCAGGAAAGAACATGTGAGCAAAAGGCCAGCAAAAGGCCAGGAACCGTAAAAAGGCCGC
GTTGCTGGCGTTTTTCCATAGGCTCCGCCCCCCTGACGAGCATCACAAAAATCGACGCTCAAGTCAGAGGT
GGCGAAACCCGACAGGACTATAAAGATACCAGGCGTTTCCCCCTGGAAGCTCCCTCGTGCGCTCTCCTGTT
CCGACCCTGCCGCTTACCGGATACCTGTCCGCCTTTCTCCCTTCGGGAAGCGTGGCGCTTTCTCATAGCTC
ACGCTGTAGGTATCTCAGTTCGGTGTAGGTCGTTCGCTCCAAGCTGGGCTGTGTGCACGAACCCCCCGTTC
AGCCCGACCGCTGCGCCTTATCCGGTAACTATCGTCTTGAGTCCAACCCGGTAAGACACGACTTATCGCCA
CTGGCAGCAGCCACTGGTAACAGGATTAGCAGAGCGAGGTATGTAGGCGGTGCTACAGAGTTCTTGAAGTG
GTGGCCTAACTACGGCTACACTAGAAGGACAGTATTTGGTATCTGCGCTCTGCTGAAGCCAGTTACCTTCG
GAAAAAGAGTTGGTAGCTCTTGATCCGGCAAACAAACCACCGCTGGTAGCGGTGGTTTTTTGTTTGCAAG
CAGCAGATTACGCGCAGAAAAAAAGGATCTCAAGAAGATCCTTTGATCTTTTCTACGGGGTCTGACGCTCA
GTGGAACGAAAACTCACGTTAAGGGATTTTGGTCATGAGATTATCAAAAAGGATCTTCACCTAGATCCTTT
TAAATTAAAAATGAAGTTTTAAATCAATCTAAAGTATATATGAGTAAACTTGGTCTGACAGTTACCAATGC
TTAATCAGTGAGGCACCTATCTCAGCGATCTGTCTATTTCGTTCATCCATAGTTGCCTGACTCCCCGTCGT
GTAGATAACTACGATACGGGAGGGCTTACCATCTGGCCCCAGTGCTGCAATGATACCGCGAGACCCACGCT
CACCGGCTCCAGATTTATCAGCAATAAACCAGCCAGCCGGAAGGGCCGAGCGCAGAAGTGGTCCTGCAACT
TTATCCGCCTCCATCCAGTCTATTAATTGTTGCCGGGAAGCTAGAGTAAGTAGTTCGCCAGTTAATAGTTT
GCGCAACGTTGTTGCCATTGCTGCAGGCATCGTGGTGTCACGCTCGTCGTTTGGTATGGCTTCATTCAGCT
CCGGTTCCCAACGATCAAGGCGAGTTACATGATCCCCCATGTTGTGCAAAAAAGCGGTTAGCTCCTTCGGT
CCTCCGATCGTTGTCAGAAGTAAGTTGGCCGCAGTGTTATCACTCATGGTTATGGCAGCACTGCATAATTC
TCTTACTGTCATGCCATCCGTAAGATGCTTTTCTGTGACTGGTGAGTACTCAACCAAGTCATTCTGAGAAT
AGTGTATGCGGCGACCGAGTTGCTCTTGCCCGGCGTCAACACGGGATAATACCGCGCCACATAGCAGAACT
TTAAAAGTGCTCATCATTGGAAAACGTTCTTCGGGGCGAAAACTCTCAAGGATCTTACCGCTGTTGAGATC
CAGTTCGATGTAACCCACTCGTGCACCCAACTGATCTTCAGCATCTTTTACTTTCACCAGCGTTTCTGGGT
GAGCAAAAACAGGAAGGCAAAATGCCGCAAAAAAGGGAATAAGGGCGACACGGAAATGTTGAATACTCATA
CTCTTCCTTTTTCAATATTATTGAAGCATTTATCAGGGTTATTGTCTCATGAGCGGATACATATTTGAATG
TATTTAGAAAAATAAACAAATAGGGGTTCCGCGCACATTTCCCCGAAAAGTGCCACCTGACGTCTAAGAAA
CCATTATTATCATGACATTAACCTATAAAAATAGGCGTATCACGAGGCCCTTTCGTCTTCAAGAATTCTCA
TGTTTGACAGCTTATCATCGATAAGCTTTAATGCGGTAGTTTATCACAGTTAAATTGCTAACGCAGTCAGG
CACCGTGTATGAAATCTAACAATGCGCTCATCGTCATCCTCGGCACCGTCACCCTGGATGCTGTAGGCATA
GGCTTGGTTATGCCGGTACTGCCGGGCCTCTTGCGGGATATCGTCCATTCCGACAGCATCGCCAGTCACTA
TGGCGTGCTGCTAGCGCTATATGCGTTGATGCAATTTCTATGCGCACCCGTTCTCGGAGCACTGTCCGACC
GCTTTGGCCGCCGCCCAGTCCTGCTCGCTTCGCTACTTGGAGCCACTATCGACTACGCGATCATGGCGACC
ACACCCGTCCTGTGGATCCGGGCCCCATTTCCCCT
```

Fig. 10          >pSwitch 7323bp

```
GACGGATCGGGAGATCATTCGAGCTTGCATGCCTGCAGGTCGAAGCGGAGTACTGTCCTCCGAGTTTAAAA
GCGGAGTACTGTCCTCCGAGGATATCAGCGGAGTACTGTCCTCCGAGTCGCGAAGCGGAGTACTGTCCTCC
GAGATCGATGTCGACCCCGCCCAGCGTCTTGTCATTGGCGAATTCGAACACGCAGATGCAGTCGGGGCGGC
GCGGTCCGAGGTCCACTTCGCATATTAAGGTGACGCGTGTGGCCTCGAATCGCCTGGAGACGCCATCCACG
CTGTTTTGACCTCCATAGAAGACACCGGGACCGATCCAGCCTCCGCGGCCGGGAACGGTGCATTGGAACGC
GGATTCCCCGTGTTAATTAACAGGTAAGTGTCTTCCTCCTGTTTCCTTCCCCTGCTATTCTGCTCAACCTT
CCTATCAGAAACTGCAGTATCTGTATTTTTGCTAGCAGTAATACTAACGGTTCTTTTTTTCTCTTCACAGG
CCACCAAGCTACCGGTCCACCATGGACTCCCAGCAGCCAGATCTGAAGCTACTGTCTTCTATCGAACAAGC
ATGCGATATTTGCCGACTTAAAAAGCTCAAGTGCTCCAAAGAAAAACCGAAGTGCGCCAAGTGTCTGAAGA
ACAACTGGGAGTGTCGCTACTCTCCCAAAACCAAAAGGTCTCCGCTGACTAGGGCACATCTGACAGAAGTG
GAATCAAGGCTAGAAAGACTGGAACAGCTATTTCTACTGATTTTTCCTCGAGAAGACCTTGACATGATTTT
GAAAATGGATTCTTTACAGGATATAAAAGCATTGTTAGAATTCCCGGGTGTCGACCAGAAAAAGTTCAATA
AAGTCAGAGTTGTGAGAGCACTGGATGCTGTTGCTCTCCCACAGCCAGTGGGCGTTCCAAATGAAAGCCAA
GCCCTAAGCCAGAGATTCACTTTTTCACCAGGTCAAGACATACAGTTGATTCCACCACTGATCAACCTGTT
AATGAGCATTGAACCAGATGTGATCTATGCAGGACATGACAACACAAAACCTGACACCTCCAGTTCTTTGC
TGACAAGTCTTAATCAACTAGGCGAGAGGCAACTTCTTTCAGTAGTCAAGTGGTCTAAATCATTGCCAGGT
TTTCGAAACTTACATATTGATGACCAGATAACTCTCATTCAGTATTCTTGGATGAGCTTAATGGTGTTTGG
TCTAGGATGGAGATCCTACAAACACGTCAGTGGGCAGATGCTGTATTTTGCACCTGATCTAATACTAAATG
AACAGCGGATGAAAGAATCATCATTCTATTCATTATGCCTTACCATGTGGCAGATCCCACAGGAGTTTGTC
AAGCTTCAAGTTAGCCAAGAAGAGTTCCTCTGTATGAAAGTATTGTTACTTCTTAATACAATTCCTTTGGA
AGGGCTACGAAGTCAAACCCAGTTTGAGGAGATGAGGTCAAGCTACATTAGAGAGCTCATCAAGGCAATTG
GTTTGAGGCAAAAAGGAGTTGTGTCGAGCTCACAGCGTTTCTATCAACTTACAAAACTTCTTGATAACTTG
CATGATCTTGTCAAACAACTTCATCTGTACTGCTTGAATACATTTATCCAGTCCCGGGCACTGAGTGTTGA
ATTTCCAGAAATGATGTCTGAAGTTATTGCTGGGTCGACGCCCATGGAATTCCAGTACCTGCCAGATACAG
ACGATCGTCACCGGATTGAGGAGAAACGTAAAAGGACATATGAGACCTTCAAGAGCATCATGAAGAAGAGT
CCTTTCAGCGGACCCACCGACCCCGGCCTCCACCTCGACGCATTGCTGTGCCTTCCCGCAGCTCAGCTTC
TGTCCCCAAGCCAGCACCCCAGCCCTATCCCTTTACGTCATCCCTGAGCACCATCAACTATGATGAGTTTC
CCACCATGGTGTTTCCTTCTGGGCAGATCAGCCAGGCCTCGGCCTTGGCCCCGGCCCCTCCCCAAGTCCTG
CCCCAGGCTCCAGCCCCTGCCCCTGCTCCAGCCATGGTATCAGCTCTGGCCCAGGCCCCAGCCCCTGTCCC
AGTCCTAGCCCCAGGCCCTCCTCAGGCTGTGGCCCCACCTGCCCCCAAGCCCACCCAGGCTGGGGAAGGAA
CGCTGTCAGAGGCCCTGCTGCAGCTGCAGTTTGATGATGAAGACCTGGGGGCCTTGCTTGGCAACAGCACA
GACCCAGCTGTGTTCACAGACCTGGCATCCGTCGACAACTCCGAGTTTCAGCAGCTGCTGAACCAGGGCAT
ACCTGTGGCCCCCCACACAACTGAGCCCATGCTGATGGAGTACCCTGAGGCTATAACTCGCCTAGTGACAG
GGGCCCAGAGGCCCCCCGACCCAGCTCCTGCTCCACTGGGGGCCCCGGGGCTCCCAATGGCCTCCTTTCA
GGAGATGAAGACTTCTCCTCCATTGCGGACATGGACTTCTCAGCCCTGCTGAGTCAGATCAGCTCCTAAGG
ATCCTCCGGACTAGAAAAGCCGAATTCTGCAGGAATTGGGTGGCATCCCTGTGACCCCTCCCCAGTGCCTC
TCCTGGCCCTGGAAGTTGCCACTCCAGTGCCCACCAGCCTTGTCCTAATAAAATTAAGTTGCATCATTTTG
TCTGACTAGGTGTCCTTCTATAATATTATGGGGTGGAGGGGGGTGGTATGGAGCAAGGGGCAAGTTGGGAA
GACAACCTGTAGGGCTCGAGGGGGGGCCCGAAACCCGCTGATCAGCCTCGACTGTGCCTTCTAGTTGCCAG
CCATCTGTTGTTTGCCCCTCCCCCGTGCCTTCCTTGACCCTGGAAGGTGCCACTCCCACTGTCCTTTCCTA
ATAAAATGAGGAAATTGCATCGCATTGTCTGAGTAGGTGTCATTCTATTCTGGGGGGTGGGGTGGGGCAGG
ACAGCAAGGGGGAGGATTGGGAAGACAATAGCAAGGCATGCTGGGGATGCGGTGGGCTCTATGGCTTCTGA
GGCGGAAAGAACCAGCTGGGGCTCTAGGGGGTATCCCCACGCGCCCTGTAGCGGCGCATTAAGCGCGGCGG
GTGTGGTGGTTACGCGCAGCGTGACCGCTACACTTGCCAGCGCCCTAGCGCCCGCTCCTTTCGCTTTCTTC
CCTTCCTTTCTCGCCACGTTCGCCGGCTTTCCCCGTCAAGCTCTAAATCGGGGGCTCCCTTTAGGGTTCCG
ATTTAGTGCTTTACGGCACCTCGACCCCAAAAAACTTGATTAGGGTGATGGTTCACGTAGTGGGCCATCGC
CCTGATAGACGGTTTTTCGCCCTTTGACGTTGGAGTCCACGTTCTTTAATAGTGGACTCTTGTTCCAAACT
```

Fig. 10 Continued

```
GGAACAACACTCAACCCTATCTCGGTCTATTCTTTTGATTTATAAGGGATTTTGCCGATTTCGGCCTATTG
GTTAAAAAATGAGCTGATTTAACAAAAATTTAACGCGAATTAATTCTGTGGAATGTGTGTCAGTTAGGGTG
TGGAAAGTCCCCAGGCTCCCCAGCAGGCAGAAGTATGCAAAGCATGCATCTCAATTAGTCAGCAACCAGGT
GTGGAAAGTCCCCAGGCTCCCCAGCAGGCAGAAGTATGCAAAGCATGCATCTCAATTAGTCAGCAACCATA
GTCCCGCCCCTAACTCCGCCCATCCCGCCCCTAACTCCGCCCAGTTCCGCCCATTCTCCGCCCCATGGCTG
ACTAATTTTTTTTATTTATGCAGAGGCCGAGGCCGCCTCTGCCTCTGAGCTATTCCAGAAGTAGTGAGGAG
GCTTTTTTGGAGGCCTAGGCTTTTGCAAAAAGCTCCCGGGAGCTTGTATATCCATTTTCGGATCTGATCAG
CACGTGATGAAAAAGCCTGAACTCACCGCGACGTCTGTCGAGAAGTTTCTGATCGAAAGTTCGACAGCGT
CTCCGACCTGATGCAGCTCTCGGAGGGCGAAGAATCTCGTGCTTTCAGCTTCGATGTAGGAGGGCGTGGAT
ATGTCCTGCGGGTAAATAGCTGCGCCGATGGTTTCTACAAAGATCGTTATGTTTATCGGCACTTTGCATCG
GCCGCGCTCCCGATTCCGGAAGTGCTTGACATTGGGGAATTCAGCGAGAGCCTGACCTATTGCATCTCCCG
CCGTGCACAGGGTGTCACGTTGCAAGACCTGCCTGAAACCGAACTGCCCGCTGTTCTGCAGCCGGTCGCGG
AGGCCATGGATGCGATCGCTGCGGCCGATCTTAGCCAGACGAGCGGGTTCGGCCCATTCGGACCGCAAGGA
ATCGGTCAATACACTACATGGCGTGATTTCATATGCGCGATTGCTGATCCCCATGTGTATCACTGGCAAAC
TGTGATGGACGACACCGTCAGTGCGTCCGTCGCGCAGGCTCTCGATGAGCTGATGCTTTGGGCCGAGGACT
GCCCCGAAGTCCGGCACCTCGTGCACGCGGATTTCGGCTCCAACAATGTCCTGACGGACAATGGCCGCATA
ACAGCGGTCATTGACTGGAGCGAGGCGATGTTCGGGGATTCCCAATACGAGGTCGCCAACATCTTCTTCTG
GAGGCCGTGGTTGGCTTGTATGGAGCAGCAGACGCGCTACTTCGAGCGGAGGCATCCGGAGCTTGCAGGAT
CGCCGCGGCTCCGGGCGTATATGCTCCGCATTGGTCTTGACCAACTCTATCAGAGCTTGGTTGACGGCAAT
TTCGATGATGCAGCTTGGGCGCAGGGTCGATGCGACGCAATCGTCCGATCCGGAGCCGGGACTGTCGGCG
TACACAAATCGCCCGCAGAAGCGCGGCCGTCTGGACCGATGGCTGTGTAGAAGTACTCGCCGATAGTGGAA
ACCGACGCCCCAGCACTCGTCCGAGGGCAAAGGAATAGCACGTGCTACGAGATTTCGATTCCACCGCCGCC
TTCTATGAAAGGTTGGGCTTCGGAATCGTTTTCCGGGACGCCGGCTGGATGATCCTCCAGCGCGGGGATCT
CATGCTGGAGTTCTTCGCCCACCCCAACTTGTTTATTGCAGCTTATAATGGTTACAAATAAAGCAATAGCA
TCACAAATTTCACAAATAAAGCATTTTTTTCACTGCATTCTAGTTGTGGTTTGTCCAAACTCATCAATGTA
TCTTATCATGTCTGTATACCGTCGACCTCTAGCTAGAGCTTGGCGTAATCATGGTCATAGCTGTTTCCTGT
GTGAAATTGTTATCCGCTCACAATTCCACACAACATACGAGCCGGAAGCATAAAGTGTAAAGCCTGGGGTG
CCTAATGAGTGAGCTAACTCACATTAATTGCGTTGCGCTCACTGCCCGCTTTCCAGTCGGGAAACCTGTCG
TGCCAGCTGCATTAATGAATCGGCCAACGCGCGGGGAGAGGCGGTTTGCGTATTGGGCGCTCTTCCGCTTC
CTCGCTCACTGACTCGCTGCGCTCGGTCGTTCGGCTGCGGCGAGCGGTATCAGCTCACTCAAAGGCGGTAA
TACGGTTATCCACAGAATCAGGGGATAACGCAGGAAAGAACATGTGAGCAAAAGGCCAGCAAAAGGCCAGG
AACCGTAAAAAGGCCGCGTTGCTGGCGTTTTTCCATAGGCTCCGCCCCCCTGACGAGCATCACAAAAATCG
ACGCTCAAGTCAGAGGTGGCGAAACCCGACAGGACTATAAAGATACCAGGCGTTTCCCCCTGGAAGCTCCC
TCGTGCGCTCTCCTGTTCCGACCCTGCCGCTTACCGGATACCTGTCCGCCTTTCTCCCTTCGGGAAGCGTG
GCGCTTTCTCATAGCTCACGCTGTAGGTATCTCAGTTCGGTGTAGGTCGTTCGCTCCAAGCTGGGCTGTGT
GCACGAACCCCCCGTTCAGCCCGACCGCTGCGCCTTATCCGGTAACTATCGTCTTGAGTCCAACCCGGTAA
GACACGACTTATCGCCACTGGCAGCAGCCACTGGTAACAGGATTAGCAGAGCGAGGTATGTAGGCGGTGCT
ACAGAGTTCTTGAAGTGGTGGCCTAACTACGGCTACACTAGAAGAACAGTATTTGGTATCTGCGCTCTGCT
GAAGCCAGTTACCTTCGGAAAAGAGTTGGTAGCTCTTGATCCGGCAAACAAACCACCGCTGGTAGCGGTG
GTTTTTTTGTTTGCAAGCAGCAGATTACGCGCAGAAAAAAAGGATCTCAAGAAGATCCTTTGATCTTTTCT
ACGGGGTCTGACGCTCAGTGGAACGAAAACTCACGTTAAGGGATTTTGGTCATGAGATTATCAAAAAGAAT
CTTCACCTAGATCCTTTTAAATTAAAAATGAAGTTTTAATCCAATCTAAAGTATATATGAGTAAACTTGGT
CTGACAGTTACCAATGCTTAATCAGTGAGGCACCTATCTCAGCGATCTGTCTATTTCGTTCATCCATAGTT
GCCTGACTCCCCGTCGTGTAGATAACTACGATACGGGAGGGCTTACCATCTGGCCCCAGTGCTGCAATGAT
ACCGCGAGACCCACGCTCACCGGCTCCAGATTTATCAGCAATAAACCAGCCAGCCGGAAGGGCCGAGCGCA
GAAGTGGTCCTGCAACTTTATCCGCCTCCATCCAGTCTATTAATTGTTGCCGGGAAGCTAGAGTAAGTAGT
TCGCCAGTTAATAGTTTGCGCAACGTTGTTGCCATTGCTACAGGCATCGTGGTGTCACGCTCGTCGTTTGG
```

Fig. 10 Continued

```
TATGGCTTCATTCAGCTCCGGTTCCGAACGATCAAGGCGAGTTACATGATCCCCCATGTTGTGCAAAAAAG
CGGTTAGCTCCTTCGGTCCTCCGATCGTTGTCAGAAGTAAGTTGGCCGCAGTGTTATCACTCATGGTTATG
GCAGCACTGCATAATTCTCTTACTGTCATGCCATCCGTAAGATGCTTTTCTGTGACTGGTGAGTACTCAAC
CAAGTCATTCTGAGAATAGTGTATGCGGCGACCGAGTTGCTCTTGCCCGGCGTCAATACGGGATAATACCG
CGCCACATAGCAGAACTTTAAAAGTGCTCATCATTGGAAAACGTTCTTCGGGGCGAAAACTCTCAAGGATC
TTACCGCTGTTGAGATCCAGTTCGATGTAACCCACTCGTGCACCCAACTGATCTTCAGCATCTTTTACTTT
CACCAGCGTTTCTGGGTGAGCAAAAACAGGAAGGCAAAATGCCGCAAAAAAGGGAATAAGGGCGACACGGA
AATGTTGAATACTCATACTCTTCCTTTTTCAATATTATTGAAGCATTTATCAGGGTTATTGTCTCATGAGC
GGATACATATTTGAATGTATTTAGAAAAATAAACAAATAGGGGTTCCGCGCACATTTCCCCGAAAAGTGCC
ACCTGACGTC
```

VIRAL VECTORS WHOSE REPLICATION AND, OPTIONALLY, PASSENGER GENE ARE CONTROLLED BY A GENE SWITCH ACTIVATED BY HEAT IN THE PRESENCE OR ABSENCE OF A SMALL-MOLECULE REGULATOR

RELATED APPLICATIONS

This application is a continuation-in-part of application Ser. No. 10/731,961, filed Dec. 10, 2003 now abandoned.

TECHNICAL FIELD

The present invention relates to viral vectors whose replication and, optionally, passenger gene expression are regulated by a gene switch that is dually controlled by heat and a small-molecule regulator.

BACKGROUND OF THE INVENTION

There are numerous situations in biological research, ex vivo cell therapies and gene therapies of experimental animals and, eventually, humans, where careful control of the distribution and expression of an introduced gene or a replicating virus is critically important. Viral and non-viral vectors provide means for delivering genes to cells, tissues and organs. However, this delivery is, typically, not specific for any particular cell type, tissue or organ location. Previously, so-called tissue-specific promoters were used to restrict virus replication or expression of a gene delivered by a vector to cells of a specific type. A shortcoming of this approach is that is uncertain whether a "tissue-specific" promoter really exists. Although a promoter may have a much stronger activity in a particular cell type than in others, it is likely to display at least some activity in some other cells. Furthermore, the rate of transcription supported by a chosen tissue-specific promoter, which rate is an intrinsic property of the promoter, may limit its usefulness. Other approaches for controlling expression of therapeutic genes included the use of two-component gene switches that are activated or inactivated by a small-molecule regulator. Well-known switches are controlled by tetracycline, ecdysterone, mifepristone or rapamycin. While these switches may allow for stringent on-off regulation of gene activity, basal gene activity cannot be controlled, and intermediate levels of gene activity are typically difficult to achieve. More important, gene expression cannot be locally restricted by a small molecule regulator that readily diffuses through tissues. Because an activating heat treatment can be directed to a target tissue, heat shock gene promoters should provide an effective means for restricting expression of a gene delivered by a viral or other vector to a target tissue. These promoters have also been suggested to be useful for controlling viral replication (U.S. Ser. No. 09/850,270). Some of these promoters, in particular a human hsp70B gene promoter isolated and characterized by the inventor, have minimal basal activity and a heat-induced activity that can be a thousand fold greater than basal activity. Such promoters should be particularly useful for achieving strict regulation of localized gene expression or virus replication. However, there is a downside to using promoters that are activated by transient heat and other proteotoxic stresses. After introduction into an experimental animal or a human, inadvertent activation of these promoters can occur during a fever or ischemia/reperfusion, exercise, exposure to oxidant or other proteotoxic agent, or, possibly, even hormonal stress. The confounding effects of such inadvertent, non-directed activation of virus replication or gene expression will be unacceptable in many applications. Gene switches that are only activated by a combination of heat (or other proteotoxic stress) and a small molecule regulator were previously described and were suggested to be useful for achieving safe spatial as well as temporal control of therapeutic gene expression (U.S. Pat. No. 6,342,596; U.S. patent application Ser. No. 10/046,420).

SUMMARY OF THE INVENTION

The present invention relates to a modified, conditionally replicating virus whose genome includes a gene switch that controls the expression of a viral gene required for efficient replication of the modified virus wherein the gene switch is activated in a cell infected by the modified virus upon exposure of the cell to heat and a small-molecule regulator. A modified, conditionally replicating virus of the invention is an engineered or recombinant virus whose replication is controlled by a mechanism not inherently present in the corresponding wildtype virus, which mechanism allows for deliberate induction of replication of the modified, conditionally replicating virus. A gene required for efficient replication of a virus is a viral gene that when defective reduces the rate of replication to less than about 25%, preferably less than about 10%, of the rate observed in the presence of the functional gene.

The invention similarly relates to a modified, conditionally replicating virus whose genome includes a gene switch that controls the expression of a viral gene required for efficient replication of the modified virus, wherein in a cell infected by the modified virus the gene switch can be activated by exposure of the cell to heat in the absence of a small-molecule regulator of the gene switch. More than one viral gene required for efficient replication may be placed under the control of the gene switch present in the modified, conditionally replicating viruses of the invention. A modified, conditionally replicating virus of the invention may further include a passenger gene. Expression of such a passenger gene can also be regulated by the gene switch that controls viral replication. Preferably, a modified, conditionally replicating virus is derived from a member of the Adenoviridae, Herpesviridae, and Retroviridae families. More preferably, a modified, conditionally replicating virus is derived from a member of the Adenoviridae family. Most preferably it is derived from a virus of the genus Adenovirus. If the modified, conditionally replicating virus is an adenovirus, the genes that can be controlled by the gene switch include the genes encoding E1A, E1B and E4.

The gene switch that controls the expression of one or more viral genes, whose products are required for efficient viral replication, minimally consists of two components. The first component is a gene for a transactivator that is activated or inhibited by a small-molecule regulator. In preferred embodiments, expression of the transactivator gene is controlled by a functionally linked nucleic acid sequence that acts as a heat shock promoter and is activated by transient heat or a transient proteotoxic stress through the intermediary of endogenous heat shock factor 1 (HSF1), or by a nucleic acid sequence containing a tandem or hybrid promoter that acts as a heat shock promoter as well as a transactivator-responsive promoter and is activated by transient heat or proteotoxic stress through the intermediary of endogenous HSF1 and active transactivator. The term "transactivator-responsive promoter" as used herein means a promoter that activates transcription of a functionally linked gene subsequent to binding of activated transactivator. Depending on the choice of transactivator, the DNA-binding activity or transcriptional activity of a transactivator may be induced or inhibited upon interaction of the transactivator with its small-molecule regulator or ligand. It is noted that the above single first component may be replaced by a set of two or more components that together perform the function of the single first component. For example, a transactivator gene that is functionally linked to a nucleic acid sequence which acts as a heat- and transactivator-responsive promoter may be replaced by a set of two genes encoding the same transactivator, the first gene being functionally linked to a nucleic acid that acts as a heat shock promoter and the second gene to a nucleic acid that acts as a transactivator-responsive promoter. Further, a transactivator may be a hetero-oligomeric protein. In such a case, the first component of a gene switch would the an assembly of all required subunit genes, at least one of which genes would be functionally linked to a nucleic acid sequence which acts as a heat shock promoter or as a heat-activated and transactivator-responsive promoter. The second component of the gene switch is a nucleic acid sequence that acts as a promoter responsive to the transactivator, which promoter is functionally linked to the viral or passenger gene to be regulated. The second component may also be a set of similar nucleic acid sequences that act as transactivator-responsive promoters and are functionally linked to viral and/or passenger genes to be regulated. In alternative embodiments, the first gene switch component is a transactivator gene, or set of subunit genes for a hetero-oligomeric transactivator as the case may be, that is expressed continuously (constitutively) in a host cell. The second component can be a modified heat shock promoter (including an appropriate RNA leader region) or a set of such promoters that are activated by transient heat or other proteotoxic stress and repressed by the transactivator. Binding of a small-molecule regulator to the transactivator can, respectively, inhibit or enable its repressing function. Hence, the resulting gene switch is active in cells exposed to heat or proteotoxic stress in the presence or absence, respectively, of the small-molecule regulator. In yet other alternative embodiments, the first component is a transactivator gene, or set of subunit genes for a hetero-oligomeric transactivator as the case may be, that is expressed continuously (constitutively) in a host cell. The second component can be a modified heat shock promoter or a set of such promoters that require co-activation by transactivator and endogenous HSF1. Transactivator may be activated by a bound small-molecule regulator or, alternatively, upon removal of a bound small-molecule regulator.

The invention also relates to a conditionally replicating pair of modified viruses consisting of (a) a first virus that is defective in one or more genes required for efficient replication and whose genome includes a gene for a small-molecule-regulated transactivator, the gene for the small-molecule-regulated transactivator being functionally linked to a nucleic acid sequence that acts as a heat shock promoter, and (b) a second virus comprising all genes required for efficient replication of which genes at least one gene is under the control of a promoter that is responsive to the small molecule-regulated transactivator of the first virus and is not complemented by a functional gene of the first virus, wherein expression of all genes of the second virus required for its replication will complement the defects of the first virus and result in replication of the first virus. This embodiment of the invention relates to a pair of modified viruses whose combined genomes contain all genetic information required for conditional replication of the virus pair. The first virus is a replication-defective virus lacking one or several genes required for efficient replication of the virus, whereas the second virus contains all genes necessary for its efficient replication, but one or more of the latter genes have been placed under the control of a gene switch that is activated by a transient stress such as heat and a small-molecule regulator. The stress- and small-molecule regulator-controlled gene or genes of the second virus are genes with functions in replication that cannot be provided by functional genes present in the first virus.

The gene switch that confers stress (e.g., heat) and small-molecule regulation upon one or more genes of the second virus comprises minimally two components that are distributed between the two viruses. The first virus contains the transactivator component that consists of a gene for a nonviral small-molecule-regulated transactivator, or of two or more genes if the transactivator is a heterooligmeric factor. The gene or, in the case of heteromeric transactivators, at least one of the genes for the transactivator is functionally linked to a nucleic acid sequence that acts as a heat shock promoter. In a variant embodiment, the transactivator gene, or at least one of the genes encoding a subunit of a multimeric transactivator, is functionally linked to a nucleic acid sequence that acts both as a heat shock promoter and a transactivator-responsive promoter. The transactivator component may also comprise two identical transactivator genes, of which one is functionally linked to a nucleic acid sequence that acts as a heat shock promoter and the other is linked to a nucleic acid sequence that acts as a transactivator-responsive promoter. The second virus contains the second gene switch component that is a nucleic acid sequence acting as a transactivator-responsive promoter. This promoter sequence is joined functionally to a gene required for efficient replication of the second virus. Multiple genes of the second virus may be joined to such a promoter sequence, subjecting them to control by the transactivator. Transactivator may be activated by a bound small molecule regulator or, alternatively, upon removal of a bound small molecule regulator.

The invention also concerns a conditionally replicating pair of modified viruses consisting of (a) a first virus that is defective in one or more genes required for efficient replication and whose genome includes a gene for a small molecule-regulated transactivator, the gene for the small molecule-regulated transactivator being functionally linked to a nucleic acid sequence that acts as a continuously active promoter, and (b) a second virus comprising all genes required for efficient replication of which genes at least one gene is under the control of a promoter that is activated upon simultaneous binding of a heat shock factor and activated transactivator and is not complemented by a functional gene of the first virus, wherein expression of all genes of the second virus required for its replication will complement the defects of the first virus and result in replication of the first virus. The first component of the gene switch in this particular embodiment consists of a continuously expressed gene for a small-molecule-regulated transactivator that is present in the genome of the first virus and is active either in the absence or in the presence of the small-molecule regulator. The second component consists of a promoter that is used to regulate one or more genes in the second virus required for efficient replication of the virus. This promoter is only active in a cell infected with the conditionally replicating pair of modified viruses subsequent to heat exposure of the cell in the presence (in the case of a small-molecule-activated transactivator) or absence (in the case of a transactivator that is inhibited by its small-molecule ligand) of small-molecule regulator. A promoter of this type may be assembled by supplementation of a basal promoter with binding sequences for heat shock transcription factor and transactivator. Alternately, one or more binding sequences for the transactivator may be introduced in an existing heat shock promoter such as the human hsp70B promoter.

The modified viruses of the conditionally replicating virus pair are typically derived from viruses of the same family, preferably from viruses of the same genus, and most preferably from viruses of the same species. These preferences are derivative of the requirement that products of one or more genes of the second virus of a pair need to be capable of complementing genetic defects of the first virus of the pair. Occasionally, this requirement is fulfilled even though the two viruses of a pair are derived from viruses of different families. An example pair of this kind could consist of a first virus derivatized from an adeno-associated virus and a second virus from an adenovirus. A further condition that needs to be fulfilled by a conditionally replicating virus pair of the invention is that the functions of the gene or genes in the second virus that are under transactivator control cannot be provided by functional genes in the first virus.

A conditionally replicating virus pair of the invention may further include a passenger gene that is inserted into the genome of the first virus of a pair. The passenger gene may be placed under the control of the same small-molecule-regulated transactivator that controls viral replication. Preferably, the modified viruses of a pair are modified members of the Adenoviridae, Herpesviridae, and Retroviridae families, with both viruses of a pair belonging to the same family. More preferably, each virus of a pair is derived from a member of the Adenoviridae family. Most preferably, each virus of a pair is an adenovirus. If the second virus of a conditionally replicating virus pair of the invention is a modified adenovirus, the genes that can be controlled by the gene switch include the E1A, E1B and E4 genes of the second virus.

BRIEF DESCRIPTION OF FIGURES

FIG. 7 provides the nucleotide sequence of pShuttle (SEQ ID NO: 1).

FIG. 8 provides the nucleotide sequence of pGene/V5-His (SEQ ID NO: 2).

FIG. 9 provides the nucleotide sequence of pXC1 (SEQ ID NO: 3).

FIG. 10 provides the nucleotide sequence of pSwitch (SEQ ID NO: 4).

DETAILED DESCRIPTION

Figure 1:
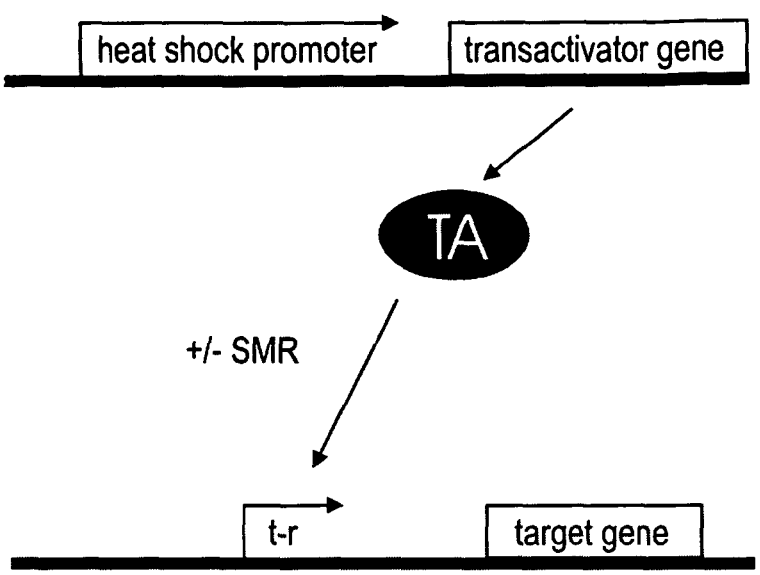
FIG. 1 presents a generic gene switch that can be activated by transient heat or proteotoxic stress in the absence or presence, respectively, of a small molecule regulator.

Unless otherwise defined, all terms shall have their ordinary meaning in the relevant art. The following terms are defined:

"Replication of virus" or "virus/viral replication" is understood to mean multiplication of viral particles.

A "modified, conditionally replicating virus" of the invention is an engineered or recombinant virus whose replication is controlled by a mechanism not inherently present in the corresponding wildtype virus, which mechanism allows for deliberate induction of replication of the modified, conditionally replicating virus. A gene required for efficient replication of a virus of the invention is a viral gene that when defective reduces the rate of replication to less than about 25%, preferably to less than about 10%, of the rate observed in the presence of the functional gene.

"Proteotoxic stress" is a physical or chemical insult that results in increased protein unfolding, reduces maturation of newly synthesized polypeptides or causes synthesis of proteins that are unable to fold properly.

A "small-molecule regulator" is understood to be a low molecular weight ligand of a transactivator used in connection with this invention. Depending on the transactivator concerned, the small-molecule regulator can inhibit or activate the transactivator. Small-molecule regulator is typically, but not necessarily, smaller than 1000 Dalton (1 kDa).

"Transactivator". To be able to use a single term for all regulatory proteins used in gene switches described herein, "transactivator" shall be understood hereinafter as being a DNA-binding protein, whose binding to a specific DNA sequence can affect, positively or negatively, transcription of a nearby gene. This definition includes traditional transactivators as well as proteins that interfere with transcription.

"Activated" when used in connection with a transactivated gene means that the rate of expression of the gene is substantially greater, typically by at least one order of magnitude, after activation than before activation. When used in connection with a transactivator, "active" or "activated" refers to a DNA-binding- and transactivation-competent form of a transactivator in the case of a positively acting transactivator, and to a DNA-binding-competent form of a transactivator in the case of a negatively acting transactivator. When used in connection with a gene switch, "activated" means that the activity of the target gene of the gene switch is substantially greater, typically by at least one order of magnitude, after activation than before activation.

"Promoter of a heat shock gene", "heat shock gene promoter" and "heat shock promoter" are used synonymously.

"Gene switch" is a molecular device that can be used to achieve regulation of a gene of interest. Minimally, a gene switch should allow an inactive gene to be activated or an active gene to be inactivated. A nucleic acid sequence functional as a regulated promoter of transcription, e.g., a heat shock promoter, represents a simple form of a gene switch. The gene switches used in connection with the invention typically consist of two types of elements, a small-molecule-regulated transactivator gene component and a target gene promoter component that is activated, co-activated or repressed by the activated or active form of the transactivator.

Herein, a virus, whose genome includes a non-viral gene, is either referred to as a "virus" or a "viral vector".

"Recombinant" or "modified" refers to the presence of an alteration caused by an experimenter.

"Passenger gene" refers to any protein- or RNA-coding gene other than a transactivator gene that is introduced into a virus of the invention.

"Conditionally replicating pair of modified viruses" refers to two nonidentical viruses (i.e., viruses differing in their genomes) that are both capable of being replicated upon co-introduction in the same cell under certain specific conditions. When introduced in separate cells, each of the viruses of the pair replicates at a substantially reduced rate that is typically at least about an order of magnitude lower than the rate achieved in the presence of the other virus.

Preferred viruses of the present invention possess the engineered property that they only replicate when cells containing them are exposed to heat or another proteotoxic stress in the presence of a small-molecule regulator. Replication of other preferred viruses can be triggered by heat or other proteotoxic stress in the absence of a specific small molecule regulator that represses replication. The viruses can further contain a passenger gene that may or may not be activated under the same conditions. Because heat can be directed, systemically present viruses of the invention can be activated locally, i.e., in a spatially restricted manner. The viruses of the invention may be used for research purposes. They may be introduced into the germline of an animal or may be introduced systemically or locally at any stage of development, including adult stage. After administration or withdrawal, respectively, of small-molecule regulator, the experimental animal may be subjected to one or more courses of localized heat to activate virus in a particular tissue or group of cells, resulting in the ablation of the targeted cells and cells in surrounding tissue and/or in activation and local spreading of an activated passenger gene and, consequently, of the product of the passenger gene. Such experiments can assist in defining the function of particular tissues or groups of cells in an adult or developing animal or in elucidating the biological or therapeutic consequences of local expression of a passenger gene. The viruses of the invention will also be useful in cell-based therapies. Cells of heterologous origin may provoke a graft-vs-host response, in spite of immunosuppressive therapy. Conditionally replicating viruses present in these cells may be specifically activated in a tissue in which rejection is observed to achieve localized killing of offending cells while maintaining the benefit of the therapy in tissues in which no rejection is observed. In other applications, immune cells containing conditionally replicating virus of the invention may be administered as a tumor therapy. Immune cells reaching the tumor may be locally activated by heat in the systemic presence (or absence) of a small-molecule regulator to trigger virus replication and cell lysis in the tumor tissue. Local cell lysis will provoke a local inflammatory response that should enhance development of specific immunity. Alternatively, cells may be infected with virus of the invention also including a passenger gene that is a therapeutic gene. After localized or systemic administration of the cells, virus replication may be activated in a desired tissue location to trigger virus replication and local dissemination of a therapeutic gene, avoiding, e.g., toxicity associated with systemic expression of the therapeutic protein. The viruses of the invention may also be used in experimental gene therapy using model animals and, eventually, humans. For example, a virus of the invention may be introduced into a tumor. Heat treatment in the systemic presence or absence, respectively, of a small-molecule regulator will initiate virus replication and tumor cell killing. The therapeutic efficacy of virus of the invention may be enhanced by the presence of a therapeutic gene, e.g., a passenger gene encoding a cytotoxic protein. Such virus will not only be induced to replicate in tumor tissue but also to express the toxic protein, resulting in increased anti-tumor activity. Alternatively, a virus of the invention may not by itself kill cells but may include a therapeutic gene, e.g., a passenger gene encoding a cytotoxic protein. Localized replication of the virus in a tumor will result in the dissemination of virus and therapeutic gene throughout the tumor. Tumor cells will be killed by the action of the therapeutic protein.

Replication of a virus of the invention is controlled by a gene switch that is activated by heat or other proteotoxic stress and the specific presence or absence, respectively, of a small-molecule regulator. Gene switches employed in the invention contain two types of components. Preferred gene switches used in connection with the conditionally replicating viruses of the invention comprise (1) a gene for a small-molecule-activated or small molecule-inhibited transactivator that is functionally linked to a nucleic acid sequence that acts as a heat shock promoter, typically a promoter from a heat shock gene, and (2) a promoter that is responsive to the transactivator. A promoter said to be responsive to a transactivator is a promoter that is activated by the active form of the transactivator. A gene to be regulated by the switch is functionally linked to the latter promoter that is responsive to the transactivator. A gene to be regulated (i.e., a target gene) may be an E1A, E1B or E4 gene in the case of a conditionally replicating adenovirus of the invention. The operation of such a gene switch is outlined in FIG. 1. A heat shock gene is defined herein as any gene, from any eukaryotic organism, whose activity is substantially enhanced when the cell containing the gene is exposed to a temperature above its normal growth temperature. Typically, the genes are activated when ambient temperature is raised by 3-10° C. Heat shock genes comprise genes for the "classical" heat shock proteins, i.e., Hsp110, Hsp90, Hsp70, Hsp60, Hsp40, and Hsp20-30. They also include other heat-inducible genes such as genes for MDR1, ubiquitin, FKBP52, hemoxidase and other proteins. The promoters of these genes, the "heat shock promoters", contain characteristic sequence elements referred to as heat shock elements (HSE) that consist of perfect or imperfect sequence modules of the type NGAAN or AGAAN, which modules are arranged in alternating orientations (Xiao and Lis. 1988. Science 239, 1139-1142; Amin et al. 1988. Mol. Cell. Biol 8, 3761-3769; Fernandes et al. 1994. Nucleic Acids Res. 22, 167-173). These elements are highly conserved in all eukaryotic cells such that, e.g., a heat shock promoter from a fruit fly is functional and heat-regulated in a frog cell (Voellmy and Rungger. 1982. Proc. Natl. Acad. Sci. USA 79, 1776-1780). HSE sequences are binding sites for heat shock transcription factors (HSFs; reviewed in Wu. 1995. Annu. Rev. Cell Dev. Biol. 11, 441-469). The factor primarily responsible for activation of heat shock genes in vertebrate cells exposed to heat or a proteotoxic stress is HSF1 (Baler et al. 1993. Mol. Cell. Biol. 13, 2486-2496; McMillan et al. 1998. J. Biol. Chem. 273, 7523-7528). Preferred promoters are those from inducible hsp70 genes. A particularly preferred heat shock promoter used in the viruses of the present invention is the promoter of the human hsp70B gene (Voellmy et al. 1985. Proc. Natl. Acad. Sci. USA 82, 4949-4953). It is noted that heat shock promoters may also be prepared synthetically or semisynthetically. For example, a basal promoter sequence (containing only elements specifying RNA polymerase II complex binding and transcription initiation) from any RNA polymerase II gene such as a viral thymidine kinase gene, an actin gene, or even a heat shock gene can be converted to a heat shock promoter by the addition of short nucleic acid elements containing a copy of the above-defined HSE sequence. Amin et al. 1988.

Examples for small-molecule-regulated transactivators than can be incorporated in the gene switches used in viruses of the invention include tetracycline/doxocycline-regulated tet-on and tet-off repressors (Gossen and Bujard. 1992. Proc. Natl. Acad. Sci. USA 89, 5547-5551; Gossen et al. 1996. Science 268, 1766-1769), ecdysterone/ponasterone-regulated insect steroid receptor-based transcription factor EcR/RXR (No et al. 1996. Proc. Natl. Acad. Sci. USA 93, 3346-3351), mifepristone-regulated GAL4-steroid receptor-activation domain chimeras such as GLVP (Wang et al. 1997. Nat. Biotechnol. 15, 239-243; Wang et al. 1997. Gene Ther. 4, 432-441), versions of which transactivator are now also commercialized under the name "GeneSwitch" (Invitrogen Corporation, Carlsbad, Calif.), and rapamycin-regulated chimeric factor NFκB-FRB/FKBP-ZFHD1 (Rivera et al. 1996. Nat. Med. 2, 1028-1032; Magari et al. 1997. J. Clin. Invest. 100, 2865-2872). Other small-molecule-regulated transactivators may be used, provided that they can be employed to control the activity of a target gene without also causing widespread deregulation of genes of the host cell and provided further that the associated small-molecule regulators have a sufficiently low toxicity for the host cell at their effective concentrations.

Figure 2:
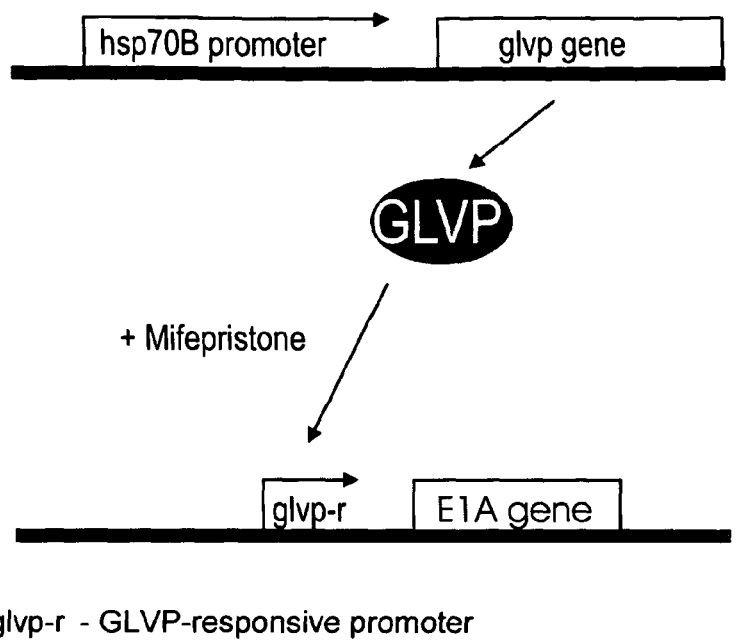
FIG. 2 provides an example of the switch of FIG. 1, in which switch generic transactivator is replaced with mifepristone-activated activator GLVP and small-molecule regulator with mifepristone.
Figure 3:
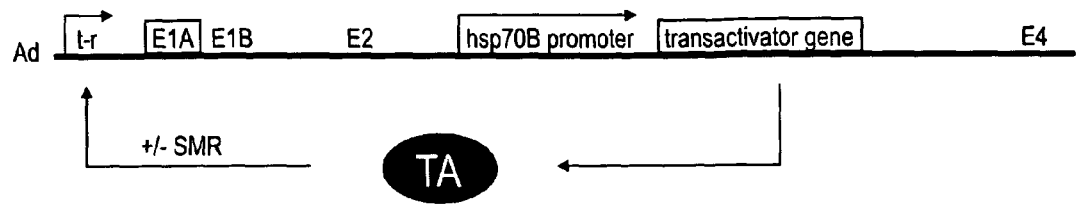
FIG. 3 outlines in part A how the generic switch of FIG. 1 can be introduced in the genome of a single adenovirus and in parts B and C how switches of FIGS. 1 and 2 can be incorporated in the genomes of a pair of adenoviruses, respectively.
Figure 3:
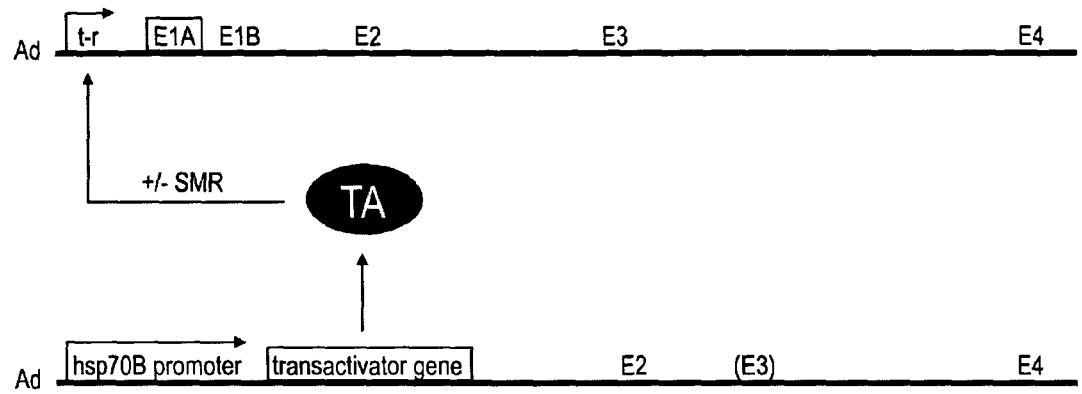
Figure 3:
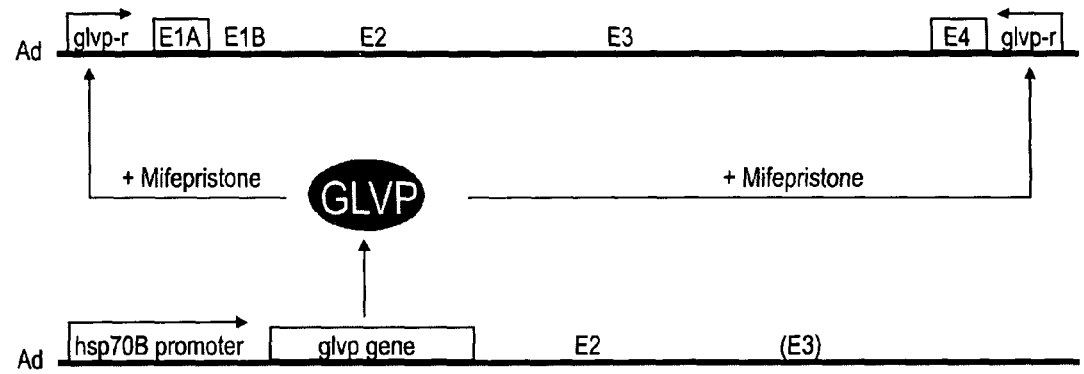

In the example in FIG. 2, a gene for mifepristone-activated, chimeric transactivator GLVP is functionally linked to strictly heat-regulated human hsp70B heat shock promoter. The target gene is a gene required for viral replication such as, in this example, the E1A gene of adenovirus. The target gene is functionally linked to a promoter that is responsive to the transactivator. In the present example, a suitable promoter will be a minimal promoter supplemented with binding sites for GAL4. A gene switch of the kind outlined in FIG. 1 may be incorporated in a viral vector to generate a conditionally replicating virus of the invention as is shown in FIG. 3 A. In this example, a transactivator-responsive promoter replaces the E1A promoter of adenovirus, and a transactivator gene cassette replaces a non-essential gene segment of the virus, e.g., an E3 region in adenovirus. Alternatively, or if there is insufficient space in the deleted virus genome for inclusion of a chosen transactivator gene, the gene switch may be distributed between two viral vectors to generate a conditionally replicating pair of modified viruses of the invention. In the example in FIG. 3 B, an hsp70B-directed transactivator gene is inserted into the genome of a typical replication-deficient adenovirus lacking E1 and, possibly, E3 sequences, and a transactivator-responsive promoter replaces the E1A promoter of an otherwise wildtype adenovirus genome. A specific example pair of conditionally replicating viruses of the invention is shown in FIG. 3 C. The first virus is a replication-deficient adenovirus that minimally lacks E1A and E4 functions. An hsp70B promoter—glvp gene cassette has been inserted in the genome of this virus. The second adenovirus is wildtype (or derived from wildtype by deletion of nonessential sequences, e.g., sequences from the E3 region), except for the E1A and E4 promoter regions that have been replaced by transactivator-responsive promoters.

In order for replication of any of the two viruses of a conditionally replicating virus pair of the invention to occur, a cell will need to be co-infected with the recombinant virus pair. Gene switch-directed virus replication would be effected as follows: subsequent to infection of a cell with the recombinant virus combination of FIG. 3 C, the cell would be exposed to an appropriate concentration of small-molecule regulator mifepristone ($10^{-10}$ to $10^{-6}$ M in the case of a mammalian cell) and subjected to a transient heat treatment (at 41-45° C. for 15-120 min in the case of a mammalian cell) to activate the hsp70B promoter. GLVP will be expressed from the hsp70B-glvp cassette present in the genome of the first virus and be activated by mifepristone. Active GLVP will then transactivate E1A and E4 gene expression from the second virus genome, resulting in replication of the virus pair. Cells in which the adenoviral replication occurred will lyse, virus particles will be liberated, and adjacent cells will be co-infected. Upon administration of a further transient heat treatment, replication in the secondarily infected cells will be triggered, and so forth.

A conditionally replicating virus or virus pair of the invention may also include a passenger gene. Whether the passenger gene or even a transactivator gene can be incorporated into a viral genome containing all genes and other sequences required for replication will depend on the type of virus, the maximal genome size for packaging, knowledge about non-essential viral genes that can be deleted, and the sizes of transactivator and passenger genes to be inserted. In the case of adenovirus, it may be necessary to insert the passenger gene and, possibly, also the transactivator gene into a partially deleted or completely gutted viral genome. As illustrated by the example of a conditionally replicating virus pair of the invention shown in FIG. 5 C, the first virus is a replication-deficient adenovirus. Space provided by sizeable deletions of viral genes, typically E1 and E3 gene regions (and in this particular case also E4 sequences), will be taken by a passenger gene and a transactivator gene. The transactivator gene, here glvp, will be under the control of a functionally linked hsp70B promoter, or the hybrid or tandem hsp70B-glvp-r promoter actually shown in the Figure (and discussed below). The passenger gene may be linked to GLVP transactivator-responsive promoter glvp-r or another promoter, as the application may require. The second virus will contain a complete adenoviral genome except for substitution of E1A and E4 promoters with glvp-r promoters.

The modified viruses of a conditionally replicating virus pair are typically derived from viruses of the same family, preferably from viruses of the same genus, and most preferably from viruses of the same species. These preferences are derivative of the requirement that products of one or more genes of the second virus of a pair need to be capable of complementing genetic defects of the first virus of the pair. Occasionally, this requirement is fulfilled even though the two viruses of a pair are derived from viruses of different families. An example pair of this kind could consist of a first virus derivatized from an adeno-associated virus and a second virus from an adenovirus. A further condition that needs to be fulfilled by a conditionally replicating virus pair of the invention is that the functions of the gene or genes of the second virus that are under transactivator control are not also provided by functional genes of the first virus.

It is noted that it is not necessary that any one of the two viruses of a conditionally replicating virus pair of the invention contain all genes required for replication. The genes may be distributed between both viruses. What is critical is that, together, the two viral genomes encode all required viral functions and that the expression of at least one viral gene product required for efficient replication of both viruses is placed under the control of a heat-activated and small-molecule-regulator-dependent gene switch.

Figure 4:
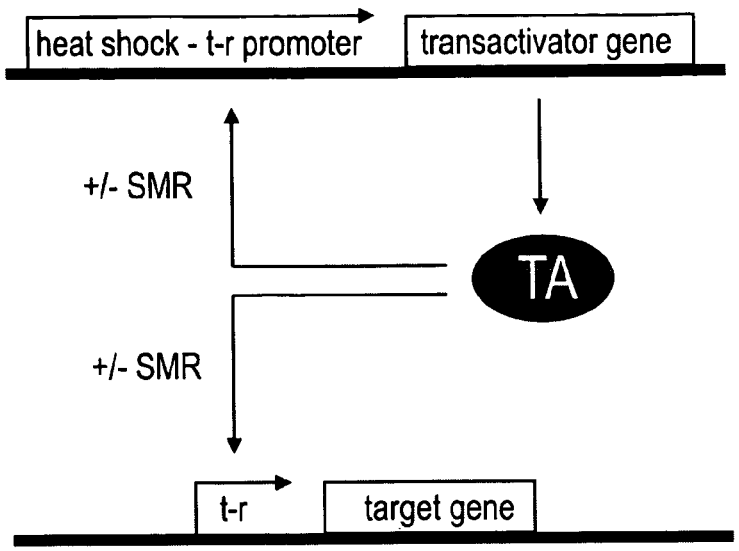
FIG. 4 presents in part A a generic gene switch that can be activated by transient heat or proteotoxic stress in the presence or absence, respectively, of a small molecule regulator. The switch contains an auto-activation loop that causes transactivator expression to be maintained subsequent to transient heat or stress activation. Part B of the Figure shows an example switch, in which generic transactivator is replaced with mifepristone-activated transactivator GLVP.
Figure 4:
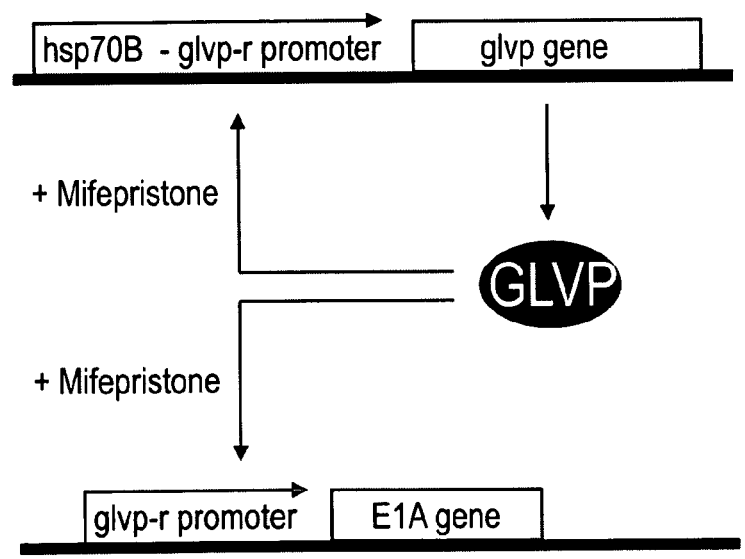
Figure 5:
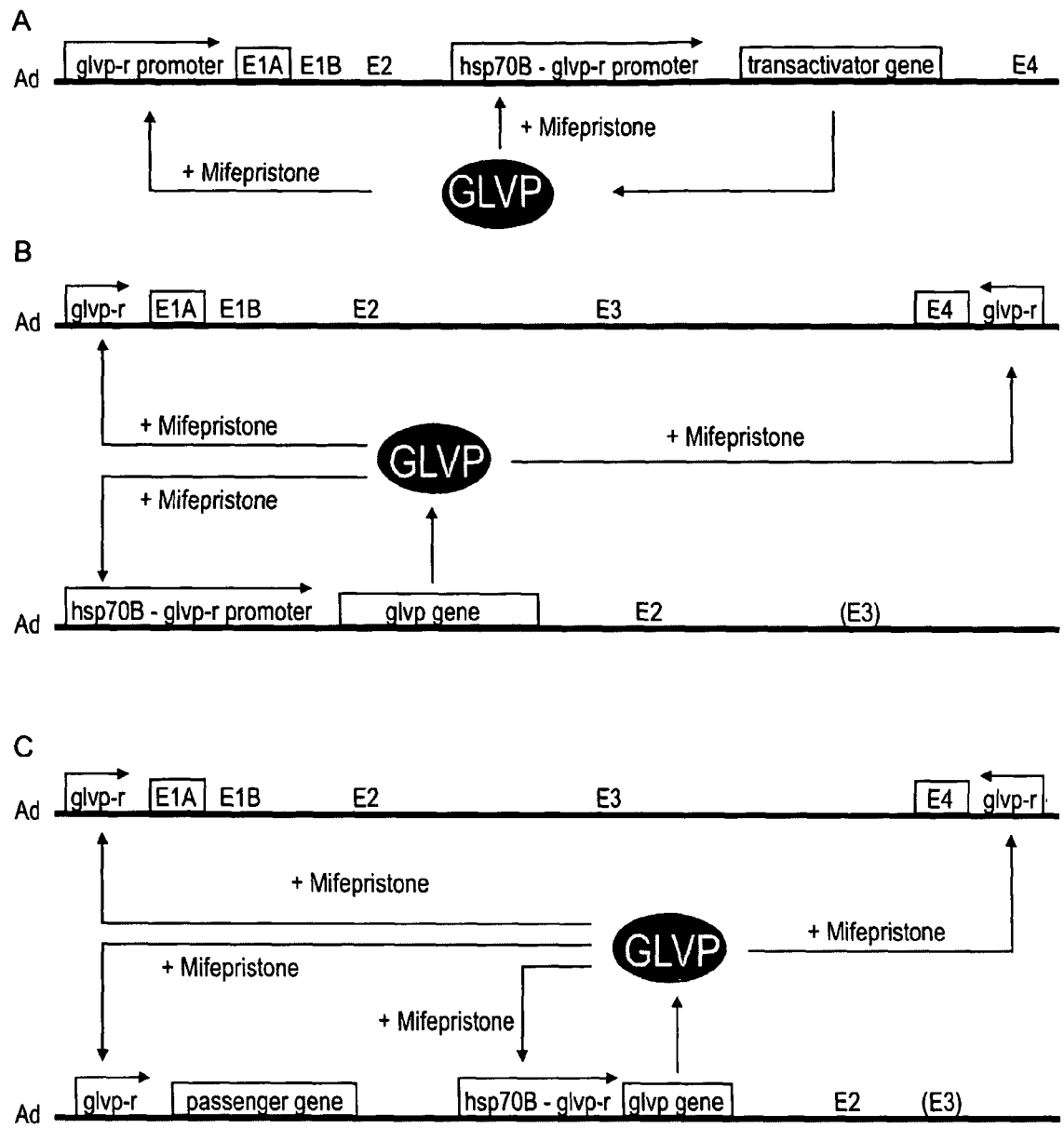
FIG. 5 outlines how an example switch of FIG. 4 B can be incorporated in the genome of a single adenovirus (part A) or the genomes of a pair of adenoviruses (parts B and C), respectively. Part C of the Figure further illustrates how a passenger gene can be introduced.

Most preferably, replication of viruses and virus pairs of the invention and, if desired, of passenger genes, is controlled by more complex switches of the kind described in U.S. Pat. No. 6,342,596 and in U.S. patent application Ser. No. 10/996, 420. Unlike the above-described switches, these switches additionally contain an auto-activating element that allows them to remain active long after an activating heat treatment or exposure to other proteotoxic stress. A generic outline of the components and operation of such switches is shown in FIG. 4 A. The switch comprises two types of components. The first component is a gene for a small-molecule-regulated transactivator, which gene is functionally linked to a nucleic acid sequence that acts as a heat shock promoter as well as a transactivator-responsive promoter. This nucleic acid sequence may contain a hybrid promoter comprising binding sites for both HSF1 and transactivator. Alternatively, it may consist of a tandem assembly of two separate promoters, one of them a heat shock promoter and the other a transactivator-responsive promoter, provided that each of the promoters can direct expression from the linked transactivator gene. The second component is a transactivator-responsive promoter to which a target gene is functionally linked. When a cell containing the two types of switch components is exposed to transient heat or other proteotoxic stress, (endogenous) HSF1 is activated and induces transcription from the transactivator gene. Depending on whether the particular transactivator used is activated or inhibited by a small-molecule regulator, newly made transactivator will activate the expression of the target gene as well as promote expression of additional transactivator protein in the presence or absence of the small-molecule regulator. As a consequence, transactivator level is maintained even after HSF1 has been inactivated subsequent to the transient stress, and target gene expression continues. Removal or addition, respectively, of small-molecule regulator will result in the inactivation of the gene switch. FIG. 4 B shows an example of a gene switch of this kind, in which gene switch the transactivator is mifepristone-activated transactivator GLVP and the target gene is the E1A gene of an adenovirus. In FIG. 5, the incorporation of the latter example switch in conditionally replicating adenoviruses of the invention is illustrated. FIG. 5 A illustrates how the glvp gene ("transactivator gene") and the linked hybrid or tandem promoter ("hsp70B-glvp-r") are introduced into the E3 region subsequent to deletion of sequences from this region. The E1A promoter is replaced by GAL4-binding site-containing promoter glvp-r that is responsive to GLVP. Whether such a recombinant can actually be made depends on the virus' packaging limit and on the lengths of the deleted and inserted sequences, respectively. In the example in FIG. 5 B, the same gene switch is distributed over a pair of viruses. The first virus (bottom) is a replication-deficient adenovirus that may lack E1, E3 and E4 sequences but contain the glvp gene and the linked hybrid or tandem promoter that is activated by heat and active GLVP. The second virus (top) may contain a complete adenoviral genome, except for replacement of E1A and E4 promoters with glvp-r promoters. As shown in the graph in FIG. 5 C, a passenger gene may also be included in the defective genome of the first virus. Expression of the passenger gene may be controlled by a transactivator-responsive promoter or another promoter.

Figure 6:
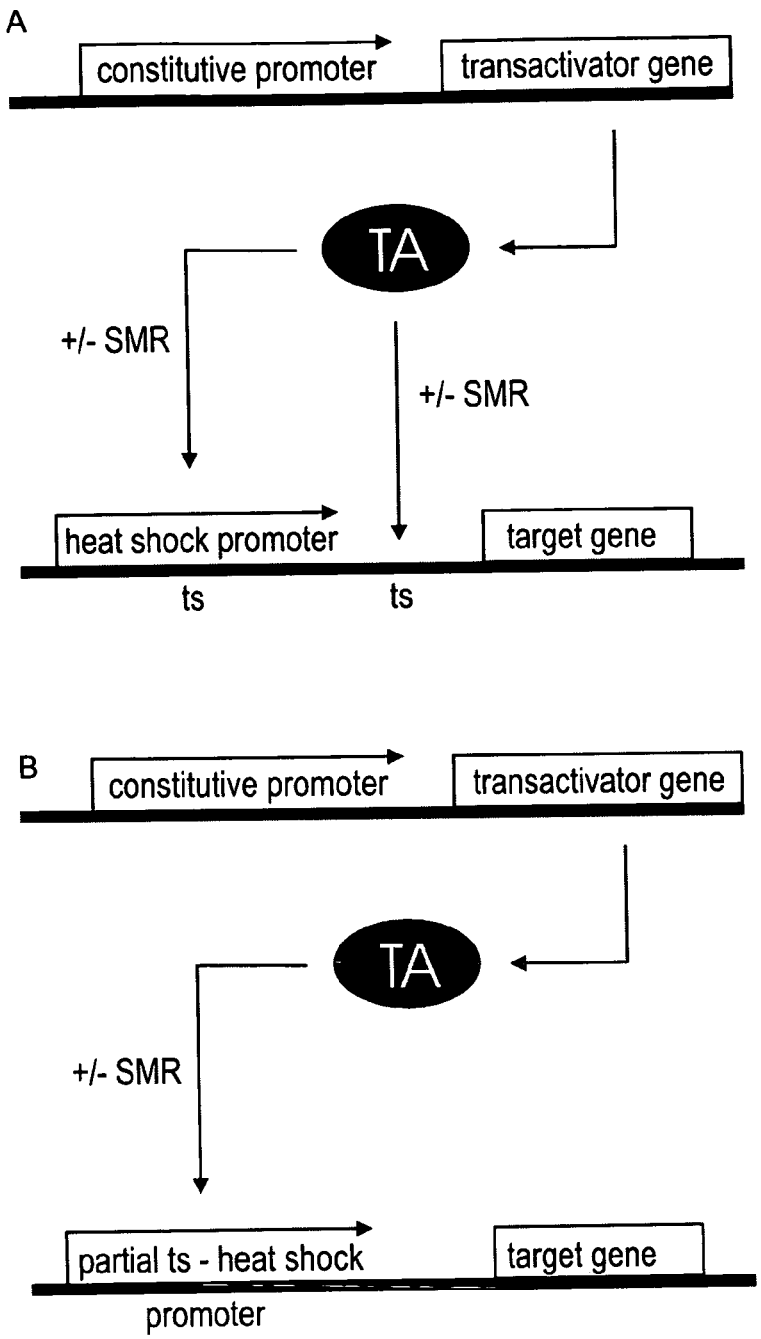
FIG. 6 outlines two types of alternative gene switches that can or may be used to regulate replication of viruses of the invention as well as passenger gene expression.

Alternatively, replication of a conditionally replicating virus of the invention and, if desired, expression of a passenger gene can be controlled by a type of gene switch (FIG. 6 A) that comprises (1) a continuously or constitutively expressed gene for a transactivator (that is not transactivation-competent), whose DNA-binding activity is regulated by binding of a small-molecule regulator and (2) a nucleic acid sequence that acts as a heat shock promoter and may also include 5' untranslated sequences, which nucleic acid sequence is modified to contain one or more transactivator binding sites. The latter promoter is functionally linked to a viral or passenger gene to be regulated. Transactivator binding sites are placed in the heat shock promoter (and/or RNA leader region) in such a way that binding of transactivator prevents heat-activated transcription of the linked gene. Binding of transactivator to sites inserted near HSF1 binding sites may prevent HSF1 binding to the promoter, and binding of transactivator to sites inserted in the 5' untranslated sequences may inhibit transcription elongation. The resulting gene switch is activated by transient heat in the presence or absence, respectively, of small molecule regulator.

An additional type of gene switch (FIG. 6 B) that may be used to control replication of conditionally replicating viruses and virus pairs of the invention and, if desired, expression of passenger genes comprises a constitutively expressed gene for a transactivator, whose DNA-binding activity (or, possibly, transcriptional competence) is activated or inhibited by binding of a small molecule regulator, and a modified heat shock promoter including one or more binding sites for the transactivator. These binding sites may be low-affinity binding sites for the transactivator, or, possibly, half sites, that are insufficient to allow activation of the promoter by the transactivator alone. The promoter is effectively co-activated by HSF1 induced by a transient heat or other proteotoxic stress and active transactivator. A modified heat shock promoter that requires co-activation may be obtained by deletion of all but one heat shock elements in a heat shock promoter, whose activation depends on the presence of multiple heat shock elements (e.g., the human hsp70B promoter), and addition of one or more transactivator binding sites. A promoter of this type may also be assembled by supplementation of a basal promoter with binding sequences for heat shock transcription factor and transactivator. Alternately, one or more binding sequences for the transactivator may be introduced in an existing heat shock promoter such as the human hsp70B promoter.

Viruses particularly suitable for use in the present invention are those that were previously used as replicating or oncolytic viral vectors such as adenoviruses, herpesviruses, and retroviruses, including foamy viruses.

The biology and genetics of adenoviruses are well understood (Russell. 2000. J. Gen. Virol. 81, 2573-2604; Hitt et al. 1997. Advances in Pharmacology 40, 137-206). Persons skilled in the art know how to prepare and administer replication-competent or replication-deficient adenovirus vectors. Strategies used to control replication of adenovirus were recently reviewed (Post et al. 2003. Hum. Gene Ther. 14, 933-946). Typically, conditional replication of adenovirus was achieved by replacing the E1A, E1B or E4 viral promoter with a regulated or tissue-selective promoter of choice. In some cases, two of the latter viral promoters were replaced. For example, Hernandez-Alcoceba et al. (Hum. Gene Ther. 11, 2009-2024 (2000)) prepared a conditionally replicating adenovirus by replacement of the E1A and E4 promoters by truncated pS2 promoters containing binding sites for estrogen receptor. The recombinant virus replicated and lysed efficiently estrogen receptor-positive but not estrogen-receptor-negative cells. Yu et al. (Cancer Res. 59, 1498-1504 (1999)) constructed conditionally replicating adenovirus 764 by substituting the E1A and E1B promoters with a PSE (prostate-specific enhancer) promoter and a promoter fragment from a kallikrein 2 gene, respectively. Virus 764 efficiently replicated in and killed cells from a prostate tumor cell line but not cells from several other cell lines.

Herpesviruses are enveloped, double-stranded DNA viruses with large genomes (152 kbp for HSV-1). This large genome size had hampered genetic analyses and experiments in the past. This problem has been solved by the use of bacterial artificial chromosomes (BACs) that allow integration of an entire herpesvirus genome, enabling the use of efficient mutagenesis and recombination protocols to manipulate the viral genome (Wagner et al. 2002. Trends in Microbiol. 10, 318-324). The products of at least two of the immediate early genes of herpesvirus, ICP4 and ICP27, are essential for viral replication (Burton et al. 2002. Curr. Opin. Biotechnol. 13, 424-428, and references cited therein). Manipulations that place one of these genes under the control of a regulated or tissue-selective promoter will produce a conditionally replicating herpesvirus. For example, Miyatake et al. (J. Virol. 71, 5124-5132 (1997)) made use of HSV-1 mutant d120 that lacked both copies of the a4 gene, the gene encoding ICP4, and inserted into this mutant an a4 gene copy that was functionally linked to a promoter containing an albumin enhancer and promoter element. The resulting recombinant herpesvirus replicated three log scales better in albumin-expressing cells than in other cells. Furthermore, the virus effectively inhibited growth of an albumin-expressing tumor xenograft. Herpesviruses can be made to preferentially replicate in mitotically active cells by deletion of genes for thymidine kinase, ICP6 or ICP34.5 (Harrington et al. 2002. Clinical Oncology 14, 3-16, and references cited therein).

Retroviruses are single-stranded, diploid RNA viruses that have been intensively investigated and used as replication-defective vectors to transfer therapeutic genes (Vile and Russell. 1995. Br. Med. Bull. 51, 12-30). Persons skilled in the art know how to manipulate retroviral genomes and how to manufacture retroviral vectors. Preparation of retroviral vectors and their uses are described in many publications including European patent application EP 0178220; U.S. Pat. No. 4,405,712; Gilboa. 1986. Biotechniques 4, 504-512; Mann et al. 1983. Cell 33, 153-159; Cone and Mulligan. 1984. Proc. Natl. Acad. Sci. USA 81, 6349-6353; Eglitis et al. 1988. Biotechniques 6, 608-614; Miller et al.1989. Biotechniques 7, 981-990; Miller. 1992. Curr. Top. Microbiol. Immunol. 158, 1-24; PCT application No. WO 92/07943 entitled "Retroviral Vectors Useful in Gene Therapy"; Hu and Pathak. 2000. Pharmacol. Rev. 52, 493-511. Promoters driving the expression of viral genes reside in the U5 and U3 regions of provirus. The actual viral genome lacks the U5 region. Hence, it only contains the promoter of the U3 region. Recently, Logg et al. (J. Virol. 76, 12783-12791 (2002)) demonstrated that replacement of the promiscuous transcriptional control elements within the U3 region in murine leukemia virus with sequences from the promoter of the androgen-regulated probasin gene that is active in the prostate, or from a variant promoter derived from the probasin promoter, resulted in recombinant virus that preferentially replicated in prostate-derived cells. Nestler et al. (Gene Ther. 4, 1270-1277 (1997) reported the construction of a replication-competent foamy virus that lacked a large segment of the U3 region and most of the bet gene. Genes encoding prodrug-activating enzymes, i.e., herpes thymidine kinase, cytosine deaminase and polynucleoside phosphorylase were fused to the truncated bet gene. The latter "suicide" proteins were expressed as fusion proteins, which were processed to yield unfused proteins due to the presence of a self-cleaving sequence at the fusion point.

More generally, viruses suitable for use in the invention include retroviruses, and single-stranded and double-stranded DNA viruses that utilize the host transcriptional machinery and whose replication depends on proteins expressed post infection. The latter DNA viruses include the Hepadnaviridae, Parvoviridae, Papovaviridae, Circoviridae, Adenoviridae and Herpesviridae families.

Papovaviridae include at least nine human papilloma viruses and polyomavirus BK and JC.

Retroviridae include the viruses of genera Lentivirus, Spornavirus and others such as HTLV-I, HTLV-II, HIV-I, HIV-II, bovine leukosis virus, feline sarcoma and leukemia viruses, avian reticuloendotheliosis, mouse mammary tumor virus, visna viruses, equine infectious anemia virus, FIV, bovine lentivirus, SUV, and foamy virus.

Hepadnaviridae include hepatitis B-like viruses, e.g. hepatitis B and other related viruses.

Parvoviridae include the genera parvovirus, dependovirus and densovirus. Adeno-associated viruses are also members of the family.

Adenoviridae include the viruses of genera Mastadenovirus and Aviadenovirus, such as human and animal mastadenovirus strains.

Herpesviridae include the viruses of genera Simplexvirus, Varicellavirus, Betaherpesvirinae, Cytomegalovirus, lymphocryptovirus, Marek's disease-like viruses and Rhadinovirus. Examples are herpes simplex virus, varicella-zoster virus, human cytomegalovirus, Marek's disease virus, EB virus and others.

Circoviridae include the genus Circovirus. Example circoviruses are chicken anemia virus, psittacine beak and feather disease virus, and porcine circovirus.

Extensive descriptions of the biology, biochemistry and genetics of the above virus families and their known members are found, e.g., in "Virology" (B. N. Fields, D. M. Knipe, and P. M. Howley, eds.), vol. 1 and 2, Lippincott-Raven Publishers, Philadelphia, Pa. (1996).

Passenger genes may include cell-affecting genes such as genes that encode apoptopic inducers, genes that affect cell death, aging, division and DNA synthesis, mitochrondial genes, peroxisomal genes, immune response-related genes, ATP-binding proteins, cytoskeletal genes, all rescue genes, genes involved in cell damage and repair. A listing of potential yeast and mammalian genes that may be included in the viral vectors of the invention is provided below.

Yeast Genes:

CELL RESCUE, DEFENSE, CELL DEATH AND AGING PRE3, PRE1, PUP2, RPN12, RPT1, MAG1, OGG1, SED1, ATH1, SPE2, GRE3, TPS2, TPS1, ATR1, ATX1, SK13, SK12, SK18, APN1, HPR5, ERG5, CCZ1, SRA1, SNF1, YCK1, YCK2, HRR25, CTA1, CTT1, WSC4, PAM1, TIR2, TIR1, HDF2, TFB4, RAD1, HAM1, LYS7, SOD1, KIN28, DIT2, ERG11, CYC7, CCP1, PHR1, DAK2, DAK1, ALR1, ALR2, HOR2, RAD17, DDC1, DDR2, ALK1, HEL1, SSL2, RAD5, SGS1, PIF1, RAD3, CDC9, REV7, NTG1, RAD18, RAD57, RAD55, XRS2, RAD30, MMS21, RAD51, RAD10, PS02, REV1, DIN7, RAD54, CDC2, PES4, POL2, REV3, RPB7, RPB4, SGE1, UBA1, UBC4, UBC5, RAD6, QR18, RNC1, NTG2, ERC1, RAD4, ETH1, FKB2, YHB1, FLR1, MEC3, ZWF1, GSH1, GRX1, TTR1, HYR1, GLR1, YCF1, FPS1, GPD1, RAS2, RAS1, CUP5, HSP26, HSP30, HSP12, HSP104, DDR48, HSC82, HSP82, MDJ1, MDJ2, HSP60, HSP78, ECM10, SSE1, SSA1, SSA3, SSA4, SSA2, SSE2, HSF1, HIG1, HDF1, HMS2, GRE1, DD11, RTA1, SIMI, LAG2, ZDS1, MET18, SNG1, NCA3, KTI12, UTH1, SUN4, SSU81, SSD1, TH14, KAR3, LIF1, SFA1, LAG1, LTV1, MDR1, SSK22, SSK2, HOL1, CIS3, HSP150, PIR3, MAC1, CUP1 A, CUP1 B, YDJ1, SSQ1, SSC1, IMP2, MPT5, ATX2, SN02, MLP1, NHX1, NCP1, NSR1, SNF4, RAD16, RAD7, RAD14, RAD23, ROD1, MGT1, OSM1, SIP18, SAT2, MNR2, MMS2, PNT1, CYP2, PAD1, PDR5, PDR3, PDR6, RTS1, PA13, HOR7, DUN1, IRE1, MKK2, MET22, PPZ2, PTC1, PTP2, MMS4, RAD52, PDR13 SLG1, GRR1 HIT1, RDH54 BRO1, PIR1 MSRA, RNR4 RNR3, HAL1, YGP1, CDC55, PPZ1, PKC1, HAL5, MKK1, HOG1, SLT2, BCKi, RAD53, SIR4, SIR3, SIR2, MGA1, FUN30, YR02, DNL4, RRD1, SAT4, RAD27, MSN2, ST11, PAU3, PAU2, PAU5, PAU1, PAU4, PAU6, (MLP1), RAD2, FZ_F1, SSU1,

SOD2, CRSS, BCK2, ASM4, TIP1, TFB1, CCL1, SSL1, TFB3, TFB2, TSAI, TRX1, TRX2, ROX3, PDR1, GTS1, MCM1, SKN7, CAD 1, MSN4, YAP1, SLN1, SSK1, PBS2, UB14, RSP5, SVS1, ZRC1.

CELL GROWTH, CELL DIVISION AND DNA SYNTHESIS GSC2, PLC1, PRE3, PRE2, PRE1, PUP2, RPN12, RPT6, RPT1, DIS3, RP SOA, AGA1, AGA2, ASG7, ACH1, ACT1, SAC6, ARP100, ABP1, PAN1, ARP 2, AREIARE2, SPE2, CYR1, SRV2, ADK2, GCS1, SOH1, TUB1, TUB3 SAG1, AKR1, YAR1, SK18, ARG82, ABF1, STE6, BAR1, 8011, TUB2, RBI-2, BIG1, BI M1, BAT1, BEM1, BEM4, SBE2, BN14, BUD6, 8012, BUD9, BUD4, BUDS, RC K2, CMK1, CNA1, CMP2, CNB1, CCH1, CMD1, SRA1, YCK1, YCK2, HRR25, CKA2, CKA1, YCK3, EST2, TFS1, SCM4, GIC2, GIC1, CAK1, BUB2, B UB3, ESR1, RAD24, DBF20, PDS1, HPC2, NUD1, CDC47, CDC10, $CDCl_3$, C DC37, CDC1, CDC40, CDC4, CDC20, CDC6, CDC46, CDC3, KAR1, BB P1, CDC50, FUS1, KRE9, EGT2, ARP1, CHS1, CHS2, CHS3, CHS5, MS11, CAC2, R LF2, CHL4, SMC1, SMC2, CIN1, SNF7, CLC1, COF1, PAM1, LAS17, HDF2, SEC3, SNF2, SW11, SNF5, SNF11, DOC1, APC2, APC5, TAP42, CDC53, KAR 9, CCE1, CLB6, CLB5, CLN3, PCL2, CLN1, PCL1, CLN2, CI-133, CI-131, CLB 4, CI-132, FAR1, CKS1, CDC28, PH085, KIN28, SSN3, CLG1, DIT2, SLA1, SLA2, SP020, DPP1, RAD17, DDC1, HEL1, DNA2, RAD5, SGS1, HCS1, PIF1, CDC9, MSH3, MSH6, MLH1, PMS1, MSH2, MSH1, POL4, REV 7, MRE11, RAD26, RAD9, RAD18, RAD57, RAD55, XRS2, MMS21, RAD51, RADIO, RAD 50, RFA3, RFA2, RFA1, RFC4, RFC5, RFC3, RFC2, RFC1, FOB1, TOP1, TO P2, TOP3, RAP1, RAD54, PR12, PR11, POL1, PO-12, CTF4, HUS2, CDC2, P ES4, POL2, DPB2, DPB3, MIP1, REV3, SSN8, GAL11, RGR1, SRB6, RP041, SEC59, DIP2, $CDCl_4$, MSG5, DYN1, UBC4, UBC9, CDC34, UBC5, UBC1, UBC6, RAD6, QR18, ELC1, RNC1, CTS1, KEX2, APG1, SSP1, SUP35, EXM2, S PR1, EXG1, EXG2, DHS1, CAP1, CAP2, BRN1, GPR1, GIF1, MEC3, TU B4, CIS2, LTE1, SDC25, SRM1, CDC25, ROM2, BUD5, ROM1, SPT16, CDC43, G IP1, SIN4, SNF6, KRE6, GFA1, NGR1, WH12, RSR1, CIN4, RAS2, RAS1, GP A1, STE4, STE18, CDC42, MDG1, SEC4, TEM1, RH03, RH04, RI-102, RHO 1, CDC24, BEM2, BUD2, BEM3, LRG1, GPA2, SIS1, HSP82, HSF1, ABF2, HDF1, HDR1, RPD3, HSL7, HO, SBA1, HPR1, IDS2, NFI1, CSE2, MDM 1, MI-1 131, MIDI, SIMI, HIR3, SIS2, MAKI 1, LAS1, SPA2, WH14, ECM33, SET1, CTF19, CIN2, MCM16, SLK19, CYK2, CNM67, SST2, DPB11, DOS2, D FG16, AFR1, ZDS1, SR07, PEA2, FAR3, SMP2, WH13, CDC5, MET30, SAS2, SCC2, CIS 1, STN1, UTH1, PAC2, SSD1, SRP1, KRE5, KIP1, CIN8, SMY1, KIP2, KAR3, KIP3, CBF1, CBF2, SKP1, CEP3, CTF13, DBR1, LAG1, MIH1, BFR1, DIG2, DIG1, MFA1, MFA2, MFAlpha1, MFAlpha2, MID2, SSF1, MATALPHA2, MATA LPHA1, ALPHAI, ALPHA2, A2, A1, SAN1, PGD1, SPO11, MSH5, DMC 1, ISC10, MSH4, SP013, NDT80, REC104, HOPI, RED1, SP07, MUM2, ME15, S AE2, NAM8, REC107, REC102, REC114, MER1, RIM01, NDJ1, CDC54, CP R7, SYGI, MCM2, CIS3, HSP150, ACE2, CDC48, ASE1, YTM1, HSM3, YD J1, ERV1, FUS3, JNM1, MCD1, MMC1, MSB1, MSB2, MPT5, ZDS2, MSN5, KEM1, MLC1, MY02, MY04, MY05, MY03, MY01, DEC1, PMD1, M DS3, ASH1, UME1, UME6, NHP6A, RFT1, TRF5, NNF1, NDC1, BIK1, KAR2, KAR5, NUM1, CDC39, MAK16, NAP1, RAD16, RAD23, NBP35, ORC1, ORC6, ORC5, ORC4, ORC3, RRR1, SIC1, BUD3, PWP2, STE3, STE2, OPY2, STE50, STE5, PEL1, TOR1, TOR2, PIK1, STT4, MSS4, SP014, POL32, IME4, SHP1, PDS5, FEN1, CSE1, FL08, PFY1, PHB2, PHB1, POI-30, AXL1, STE23, RAD28, CDC7, SMP3, MKK2, CDC15, ARD1, CHU, PPH3, PPH21, PPH22, PTC1, SE C9, PPS1, PTP3, YVH1, PTP2, PUS4, PCH2, PCH1, CBF5, SEF1, MMS4, SHR5, RAD59, RAD52, RHC18, RGP1, RVS167, RIM9, BNR11, BN11, SPT3, SOK2, KAR 4, DBF4, SDS22, MCM3, CTF18, SR04, SPH1, FUS2, MOB1, FL08, FIG1, FIG2, END3, DFG5, CTR9, TOM1, POP2, GRR1, SCP160, SUR1, MUM3, ZIP2 CDC45, RDH54, SHE3, SHE2, SHE4, GP11, MIF2, ESP1, HOP2, DNA43, SMC3, PAC11, PAC10, RD11, RGA1, RNR1, RNR2, RNR4, RNR3, PRPS1, RPL10, RPS1A, MTF1, SN12, $CDCl_2$, CDC11, SPR28, CDC55, GLC7, PKC1, G1 N4, SPS1, RCK1, BUB1, IME2, YAK1, YPK2, RIM11, CLA4, MKK1, MEK1, I PL1, SGV1, SLT2, KSS1, BCK1, STE11, STE20, DBF2, HSL1, NRK1, SIT4, T PD3, ELM1, MCK1, RAD53, STE7, SWE1, MPS1, SAS3, HST1, SIR4, SIR3, SIR1, SIR2, CTH1, DOM34, HST4, RVS161, DNL4, IQG1, FUN16, HYM1, RT S2, MNN10, PRK1, MCM6, SAP155, SAP4, SAP190, SAP185, MUD13, MAD 1, CIK1, NUF1, SPC97, SPC42, SPC98, CDC31, NUF2, MAD3, MAD2, DI T1, YSW1, SP012, SP016, MCD4, BDF1, SGA1, GSG1, SHC1, CDA1, CD A2, SMK1, SPS2, SPR6, SLZ1, SPS4, SPR3, SPS100, SPS18, RAD27, SNZ 1, SUR4, ST11, SBE22, CSE4, BMH 1, SVL3, SCH9, (MLP1), SSF2, RAD2, CDH1, CDC27, CDC26, CDC23, CDC16, APC1, APC 11, APC4, APC9, SAP30, RSC6, RSCS, STH1, SFH1, SAS5, JSN1, BMH2, SMT4, BCK2, HOC1, ZIP1, UFE1, EST1, TEL1, ANC1, CCL1, DST1, TRXI, TRX2, TRF4, PAT1, SPT4, SP T6, CDC36, SWI5, SWI4, PHD1, SWI6, GTS1, MCM1, IME1, SKN7, MBP1, SW13, SIN3, STE12, CIN5, SDS3, SP1, MOT2, RPG1, PRT1, CDC33, TPM1, TPM2, TWF1, TEC1, TTP1, STE13, PRP8, UB14, DSK2, RSP5, D OA4, UNG1, VPS45, VAN1, VRP1, DFG10, YHM2, GL'Q3, SFP 1, STE24, RME1, SAE3, ME14, NHP6B, MOB2, EST3, RIM1.

HEAT SHOCK PROTEINS CAT5, CPH1, CTT1, CYP2, DDR2, FPR2, HSC82, HSP104, HSP12, HSP150, HSP26, HSP30, HSP42, HSP60, HSP78, HSP82, KAR2, MDJ1, SIS1, S OD2, SSA1, SSA2, SSA3, SSA4, SSB1, SSB2, SSC1, SSE1, SSE2, ST11, TIP 1, TPS2, UB14, YDJ1.

MITOCHONDRIAL AAC1, AAC3, AAT1, ABC1, ABF2, ACO1, ACR1, ADH3, ADK2, AEP2, AFG3, ALD1, ALD2, ARG11, ARG2, ARG5,6, ARG7, ARG8, ARH1, AT M1, ATP1, ATP10, ATP11, ATP12, ATP14, ATP15, ATP16, ATP2, ATP3, ATP4, A TP5, ATP6, ATP7, ATPS, ATP9, BAT1, BCS1, CBP1, CBP2, CBP3, CBP4, CB P6, CBR1, CBS1, CBS2, CCA1, CCE1, CCP1, CEM1, CIT1, CIT3, COB, CO Q1, COQ2, COQ3, COQ6, COR1, COT1, COX1, COX10, COX11, COX12, COX3, COX14, COX15, COX17, COX2, COX3, COX4, COX5A, COX5B, COX6, COX7, COX8, COX9, CPR3, CTP1, CYB2, CYC1, CYC2, CYC3, CYC7, CYT1, CYT2, DB156, DLD1, DTP, ENS2, ERV1, FLX1, FUM1, GCV1, GCV3, G1-04, GPD2, GSD2, GUT2, HEM1, HEM15, HSP10, HSP60, HSP78, HTS1, IDH1, ID H2, IDP1, IFM1, ILV1, ILV2, ILV3, ILV5, ILV6, IMP1, IMP2, INH1, ISM1, KG D1, KGD2, LAT1, LEU4, LIP5, LPD1, LYS12, LYS4, MAE1, MAM33, MAS1, MAS2, MBA1, MCR1, MDH1, MDJ1, MDJ2, MDM10, MDM12, MEF1, MEF2, MET13, MGE1, MGM101, MIP1, MIR1, MIS1, MMM1, MMTi, M MT2, MOD5, MOL1, MRF1, MRP1, MRP13, MRP17, MRP2, MRP20, MRP21, MRP4, MRP49, MRP51, MRP8, MRPL10, MRPL 11, MRPL13, MRPL15, MRPL16, MRPL 17, MRPL 19, MRPL2, MRPL20, MRPL23, MRPL24, MRPL25, MRPL27, MRPL28, MRP L3, MRPL31, MRPL32, MRPL33, MRPL35, MRPL36, MRPL37, MRPL38, MR PI-39, MRPL4, MRPL40, MRPL44, MRPL49, MRPL6, MRPL7, MRPL8, M RPL9, MRPS28, MRPS5, MRPS9, MRS1, MRS11, MRS2, MRS3, MRS4, MRS5, MSD1, MSE1, MSF1, MSH1, MSK1,

MSM1, MSP1, MSR1, MS S1, MSS116, MSS18, MSS51, MST1, MSU1, MSW1, MSY1, MTF1, M T01, NAM1, NAM2, NAM9, ND11, NHX1, NUC1, OM45, ORFA04514, OSM1, OXA1, PDA1, PDB1, PDX1, PEL1, PET111, PET112, PET117, PET122, PET123, PET127, PET130, PET191, PET309, PET494, PET54, PET56, PET9, PETCR46, PI-1131, PHB2, PIF1, PIM1, POR1, POR2, PPA2, PSD1, PUT1, PUT2, QCR10, QCR2, QCR6, QCR7, QCR8, QCR9, RCAi, RF2, RIM 1, RIM2, RIP1, RML2, RNA12, RPM2, RP 041, SC01, SCO2, SDI-11, SDH2, SDI-13, SDI-14, SECY, SHM1, SHY1, SLS1, SMF2, SOD2, SOM1, SSC1, SS.COPYRGT.1, STF1, STF2, SUN4, SUV3, TIM17, TIM22, TIM23 TIM44, TIM54, TOM20, TOM22, TOM37, TOM40, TOM6, TOM7, TOM 70, TOM72, TRM1, TUF1, UNG1, VAR1, YAH1, YAL011W, YAT1, YBL013 W, YCR024C, YDR041W, YDR115W, YDR116C, YER073W, YFH1, YGLO68W, YGR257C, YHM1, YHR075C, YHR148W, YJL200C, YJR113C, YKLO55C, YKL120W, YKL134C, YKL192C, YLR168C, YMC1, YMC2, YML025C, YMR188C, YMR31, YNL081 C, YNL306W, YNR036C, YNR037C, YOR221C, YPL013C, ETF-BETA.

PEROXISOMAL CAT2, CIT2, CTA1, DAL7, EHD1, EHD2, FAA2, FAT2, FOX2, ICU, IDP 3, MDH3, MLS1, PEX11, PEX12, PEX13, PEX14, PEX17, PEX2, PEX3, PE X4, PEX6, PEX7, PEXB, POT1, PDX1, PXA1, PXA2, SPS19, YBR204C, YDR 449C, YHR180W DNA-ASSOCIATED A1, A2, ABF1, ABF2, ADA2, ADE12, ADR1, ALPHA1, ALPHA2, ANC1, APN1, ARGR1, ARGR2, ARGR3, ARR1, ASH1, AZF1, BAS 1, BDF1, BR F1, BURG, CAC2, CAD1, CAF17, CATB, CBF1, CBF2, CCE1, CCR4, CDCl3, CDC36, CDC39, CDC46, CDC47, CDC54, CDC6, CDC7, CDC73, CDC9, CEF1, CEP3, CHA4, CHD1, CHU, CHL4, CRZ1, CSE1, CSE2, CSE4, CTF13, CUP2, CUP9, DAL80, DAL81, DAL82, DAT1, DBF4, DMC1, DNA2, DNA43, DNL4, D OS2, DOT6, DP131 1, DPB2, DPB3, DST1, ECM22, ENS2, EST1, EZL1, FCP1, FHL1, FKH1, FKH2, FL08, FZF1, GAL11, GAL4, GAT1, GBP2, GCN4, GCNS, GCR1, GCR2, GLN3, GL03, GTS1, GZF3, HAC1, HAP1, HAP2, HAP3, HAP4, HCM1, HDA1, HDF1, HFM1, HHF1, HHF2, HH01, HHT1, HHT2, HM01, HMSI, HMS2, H0, HOP1, HPR1, HPRS, HSF1, HTA1, HTA2, HTA3, HTB1, HT 62, IFH1, IME1, IME4, IN02, IN04, IXR1, KAR4, LEU3, LYS14, LYS20, LYS21, M AC 1, MAGI, MAL13, MAL23, MAL33, MATALPHA1, MATALPHA2, MBP1, MCD1, MCM1, MCM2, MCM3, MCM6, MED6, MER2, MET18, MET28, MET30, MET31, MET32, MET4, MGA2, MGT1, MIF2, MIG1, MIG2, MIP1, MLH 1, MOL1, MOT1, MPT4, MRE11, MSH1, MSH2, MSH3, MSH4, MSHS, MS11, MSN1, MSN2, MSN4, MTF1, NBN1, NC132, NDJ1, NGG1, NHP2, NHP6 A, NHP6B, NOT3, NUC2, OAF1, OP11, ORC1, ORC2, ORC3, ORC4, ORCS, ORC6, PAF1, PCH1, PCH2, PDR1, PDR3, PGD1, PHD1, PH02, PH04, PHR1, PIF1, PIP2, PMS1, POB1, POL1, POL12, POL2, POL3, POL30, PO L4, POP2, PPR1, PRI1, PR12, PS02, PUT3, RAD1, RAD10, RAD14, RAD 16, RAD18, RAD2, RAD23, RAD26, RAD27, RAD3, RAD4, RADS, RAD50, RAD51, RAD52, RAD54 RAD55, RAD57, RAD6, RAD7, RAP1, RAT-1, RCS1, REB1, REC102, RE C104, REC114, RED1, REG1, RET1, REV3, RFA1, RFA2, RFA3, RFC1, RFC2, RFC3, RFC4, RFCS, RGM1, RGT1, RIF1, RIF2, RIM1, RIM101, RLF2, RLM1, R ME1, RMS1, ROX1, ROX3, RPA12, RPA135, RPA14, RPA190, RPA34, RPA43, RPA49, RP131 0, RPB 11, RPB2, RP133, RP134, RPBS, RPB6, RPB7, RPBB, RPB9, RPC10, RPC19, RPC25, RPC31, RPC34, RPC40, RPC53, RPC82, RPD3, RP021, RP031, RP041, RRN10, RRN11, RRN3, RRNS, RRN6, RRN7, RRN9, RSC4, RSC 6, RSC8, RTG1, RTG3, SASS, SEF1, SET1, SFH1, SFL1, SGS 1, SIG1, SIN 3, SIN4, SIP2, SIP4, SIR1, SIR2, SIR3, SIR4, SKN7, SK01, SMC 1, SMC 2, SMP1, SNF2, SNFS, SNF6, SOK2, SPKi, SPOL, SPS18, SPT10, SPT 15, SPT16, SPT2, SPT21, SPT23, SPT3, SPT4, SPT5, SPT6, SPTB, SR132, SRB4, SRBS, S RB6, SRB7, SR138, SR139, SSL2, SSN3, SSN6, SSNB, SSU72, STB4, STBS, S TE12, STH1, SUA7, SWI1, SW13, SW14, SW16, SWP73, TAF19, TAF25, THF1, TEAI, TEC1, TFAI, TFA2, TF131, TF132, TF133, TFB4, TFC1, TFC2, TF C3, TFC4, TFCS, TFG1, TFG2, TH12, TOA1, TOA2, TOP1, TOP2, TOP3, TRF4, TS P1, TUP 1, TYE7, UGA3, UME6, UNGI, USV1, XRS2, YAL019W, YAP1, YA P3, YAPS, YBL054W, YBRO26C, YBR150C, YBR239C, YCR106W, YDR026C, YDR060W, YDR213W, YER045C, YER184C, YFL052W, YIL036W, YIL 130W, YJL103C, YJL206C, YKL005C, YKL222C, YKR064W, YLL054C, YLRO 87C, YLR266C, YNL206C, YOL089C, YOR172W, YOR380W, YOX1, YPL133C, YPR008W, YPR196W, YRR1, ZAP1, ZIP1, ZU01.

IMMUNOSUPPRESSANT FEN1, SSH4, SHR3 CYCLINS CCU, CLB1, CLB2, CLB3, CL134, CLBS, CLB6, CLG1, CLN1, CLN2, CLN 3, CTK2, PCL1, PCL10, PCL2, PCLS, PCL6, PCL7, PCLB, PCL9, PH080, S SNB, YBR095C.

ATP-BINDING CASSETTE PROTEINS ADP1, ATM 1, CAF16, GCN20, MDL1, MDL2, PDR10, PDR11, PDR12, PDR15, PDRS, PXA1, PXA2, SNQ2, STE6, YBT1, YCF1, YDL223C, YD R091C, YEF3B, YER036C, YHL035C, YKR103W, YKR104W, YLL015W, YNR070W, YOR011W, YOR1, YPL226W.

CYTOSKELETAL ABP1, ACF2, ACT1, AFR1, AIP1, AIP2, ARP3, AUT2, AUT7, BEM1, BI M1, BN11, BN14, BUD3, BUD6, CAP1, CAP2, CDC10, CDC11, CDCl2, CDC 3, CIN1, CIN2, CIN4, CMD1, COF1, CRN1, END3, GIC1, GIC2, GIN4, J NM1, KAR9, KIP2, KIP3, LAS17, MDM1, MHP1, MY01, MY02, MY03, MY04, MY05, PFY1, RVS161, RVS167, SAC6, SACT, SEC 1, SHE3, SHM2, SLA1, SL A2, SMY1, SMY2, SPA2, SPH1, SPR28, SPR3, SRV2, TCP1, TPM1, TPM2, TUB1, TUB2, TUB3, VPS16, VRP1 APOPTOSIS ATP1, ATP14, ATP15, ATP16, ATP2, ATP3, ATP4, ATPS, ATP6, ATP7, ATP8, ATP9, CYC1, SH01, SSK2, SSK22, SW13, SXM1.

CELL RESCUE ACC1, ALD6, BCK1, BEM 1, BEM2, BIM1, BMH1, BMH2, CAN1, CBF1, CDC1, CDCl4, CDC15, CDC20, CDC25, CDC28, CDC33, CDC37, CDC 42, CDC43, CDC53, CDC6, CHC1, CIN8, CKA1, CKA2, CLA4, CLB1, CLB2, CLB3, CLB4, CLB5, CLN1, CLN2, CLN3, CMP2, CNA1, COF1, CTT1, DBF2, DBF20, DPM1, ERG25, GIC1, GIC2, GPA1, GRR1, HCA4, HIS4, HOC1, HSF1, KAR1, KES1, KRE6, KSS1, MBP1, NMT1, ORC2, ORC5, PDE2, PEP12, PEP7, PKC1, P LC1, PMR1, POL30, PRP18, RAM1, RAS1, RAS2, RBL2, RED1, RFC1, RH01, RH03, RH04, SAC1, SEC13, SEC14, SEC22, SEC4, SET1, SIS2, SKP1, SPC98, SRA1, SR04, SRP1, SSA1, SSA2, SSA4, SSN8, STE20, STN1, STT4, SUJ 3, SWE1, SW14, SW16, TEL1, TOR1, TUB1, TUB4, VMA1, YCK1, YCK2, YPT1.

CELL DAMAGE APN1, BUB1, CDC28, CDC45, CDC46, CDC47, CDC54, CDC1, CLB1, CLB2, CLB3, CLB5, DDC1, DDR2, DDR48, DIN7, DUN1, ECM32, HSM3, IMP2, MEC1, MEC3, MGT1, MOL1, MRE11, MUS81, NTG1, PDS1, PGD1, P HR1, POL2, POL3, POL30, POL4, PR11, PS02, RAD14, RAD16, RAD17, RAD18, RA D24, RAD30, RAD51, RAD52, RAD54, RAD55, RAD57, RAD7, RAD9, RDH54, REV3, RFA1, RFC5, RNR1, RNR2,

RNR3, RNR4, RPH1, SIC1, SML1, SP K1, STN1, STS1, TEL1, TFA1, TFA2, TUP1, UBC7, UB14, XBP1, YBR098W, YFH1.

OTHER RELEVANT MUTANTS AND GENES Y-1, 9520b, C658-K7, JPD 4, JPM 9, Cy32, E354, JC488, PSY 142, 01-2, Y217, JC787-9A, ML1-21, Y500, 86-9C, GL1, GT5-1A, HD565A, PZ1, 127-4D, Y229, JC302-26B, JC482, LB2211-2B, MH41-7B/P21, erg 81, SEY6211, GL4, K335, MK20, MK34, DE4-3A, DE4-3B, DE4-3C, MMY011, UH 1-GRGZ, 2150-2-3a, Y211, DP1/517,943,1117, C658, 1252, H79.20.3, LB1-3B, C658-K42, R29B, LB54-3A, XW520-9A, ade7, D225-5A, 309, SDH1, SDH2, SDH3, SDH4, TCM62, PDE1, PDE2.

Mammalian Genes:

11-beta hydroxysteroid dehydrogenase type II, 12-lipoxygenase, 17-beta hydroxysteroid dehydrogenase, 60S ribosomal protein L6,6-Omethylguanine-DNA methyltransferase, Activating transcription factor 2, Activating transcription factor 3, Activating transcription factor 4, Activin beta E, Activin receptor type 11, Acyl-CoA dehydrogenase, Acyl CoA Carrier Protein, Adenine nucleotide translocator 1, Alanine aminotransferase, Alcohol dehydrogenase 1, Alcohol dehydrogenase 2, Alcohol dehydrogenase 3, Alcohol dehydrogenase 4, Alcohol dehydrogenase 5, Aldehyde dehydrogenase 1, Aldehyde dehydrogenase 2, Aldehyde dehydrogenase 3, Alpha 1-antitrypsin, Alpha-1 acid glycoprotein, Alpha-1 antichymotrypsin, Alpha-catenin, Alphatubulin, Apolipoprotein A1, Apolipoprotein A11, Apolipoprotein Cl¡l, Apolipoprotein E, Aryl hydrocarbon receptor, Aspartate aminotransferase, mitochondrial, Ataxia telangeictasia, ATP-dependent helicase 11 (70 kDa), ATP-dependent helicase 11 (Ku80), BAG-1, BAK, Bax (alpha), Bcl-2, Bcl-xL, Beta-actin, Bilirubin UDP-glucuronosyl-transferase isozyme 1, Bilirubin UDP-glucuronosyl-transferase isozyme 2, Biliverdin reductase, Branched chain acylCoA oxidase, BRCA1, BR-cadherin, C4bbinding protein, c-abl, Calcineurin B, Calnexin, Calprotectin, Calreticulin, canalicular multispecific organic anion transporter, Carbonic Anhydrase 111, Carnitine palmitoyl-CoA transferase, Caspase 1, Caspase 2 (Nedd2), Caspase 3 (CPP32beta), Caspase 5 (ICE relIII), Caspase 6 (Mch2-alpha), Caspase 7 (Mch3alpha), Caspase 8 (FLICE), Catalase, CatecholOmethyltransferase, CCAAT/enhancer-binding protein alpha, CCAAT/enhancer-binding protein epsilon, Cell division cycle protein 2, Cell division cycle protein 20, Cell division cycle protein 25, Cellular retinoic acid binding protein 1, Cellular retinoic acid binding protein 2, cerb; c-fos, Checkpoint kinase-1, Cholesterol esterase, c-H-ras, cjun, Clusterin, c-myc, Complement component C3, Connexin 30, Connexin32, Connexin-40, Corticosteroid binding globulin, Corticotropin releasing factor, C-reactive protein, Creatine kinase b, Cyclin D1, Cyclin dependent kinase 1, Cyclin dependent kinase 4, Cyclin dependent kinase inhibitor 1A, Cyclin E, Cyclin G, Cyclin-dependent kinase 4 inhibitor (P116), Cyclindependent kinase 4 inhibitor B (P16), Cyclin-dependent kinase inhibitor P27Kip1, Cyclooxygenase 2, Cystic fibrosis transmembrane conductance regulator, Cytochrome P450 11A 1, Cytochrome P450 17A, Cytochrome P450 1A1, Cytochrome P450 1A2, Cytochrome P450 1 B1, Cytochrome P450 2A1, Cytochrome P450 2A3, Cytochrome P450 2A6, Cytochrome P450 2131, Cytochrome P450 21310, Cytochrome P450 2132, Cytochrome P450 2C11, Cytochrome P450 2C12, Cytochrome P450 2C19, Cytochrome P450 2C9, Cytochrome P450 2D6, Cytochrome P450 2E1, Cytochrome P450 2F2, Cytochrome P450 3A1, Cytochrome P450 3A4, Cytochrome P450 4A, Cytochrome P450 4A1, Damage specific DNA binding protein p48 subunit, Defender against cell death-1, Deleted in colorectal cancer, Deltalike protein, Dihydrofolate reductase, Disulfide isomerase related protein (ERp72), DNA binding protein inhibitor ID2, DNA dependent helicase, DNA dependent protein kinase, DNA ligase 1, DNA ligase IV, DNA mismatch repair protein (MLH1), DNA mismatch repair protein (PMS2), DNA mismatch repair/binding protein (MSH3), DNA polymerase alpha, DNA polymerase beta, DNA polymerase beta, DNA repair and recombination homologue (RAD 52), DNA repair helicase II ERCC-3, DNA repair protein (RAD 50), DNA repair protein (XRCC1), DNA repair protein XP-D, DNA replication factor C (36 kDa), DNA topoisomerase 1, DNA topoisomerase 11, Dopamine beta-hydroxylase, DRA, Dynein light chain 1, E2F, Early growth regulated protein 1, E-Cadherin, ECE-1 (endothelin converting enzyme), Endothelin-1, Enolase alpha, Enoyl CoA hydratase, Eotaxin, Epidermal growth factor, Epoxide hydrolase, ERA-B, ERCC 1 (excision repair protein), ERCC 3 (DNA repair helicase 11), ERCC 5 (excision repair protein), ERCC 6 (excision repair protein), ERK1, Erythropoietin, Erythropoietin receptor, ESelectin, Estrogen receptor, Farnesol receptor, Fas antigen, Fas associated death domain (FADD), Fas ligand, Fas/Apo1 receptor, Fatty acid synthase, Fatty acyl-CoA oxidase, Fatty acyl-CoA synthase, FEN-1 (endonuclease), Fibrinogen gamma chain, Fibronectin receptor, FIC1, Filagrin, Flavin containing monooxygenase 1, Flavin containing monooxygenase 3, FosB, Fra-1, Fucosyl transferase (alpha-1,2fucosyltransferase), Gadd153, Gadd45, Gamma-glutamyl hydrolase precursor, Gamma-glutamyl transpeptidase, GCLR, GCLS, Glucocorticoid receptor, Glucose-6-phosphate dehydrogenase, Glucose-regulated protein 170, Glucose-regulated protein 58, Glucose-regulated protein 78, Glucoseregulated protein 94, Glutamicoxaloacetic transaminase, Glutamine-pyruvic transaminase, Glutathione peroxidase, Glutathione reductase, Glutathione S-transferase alpha subunit, Glutathione S-transferase 4a, Glutathione synthetase, Glyceraldehyde 3-phosphate dehydrogenase, GOS24 (zinc finger transcriptional regulator), Granulocyte-macrophage colony-stimulating factor, Growth-arrested-specific protein 1, Growth-arrested-specific protein 3, GT mismatch binding protein, H-cadherin, Heat shock protein 12, Heat shock protein 47, Heat shock protein 70, Heat shock protein 70.1, Heat shock protein 90, Helicase-like transcription factor, Heme binding protein 23, Heme oxygenase-1, Hepatic lipase, Hepatocyte growth factor, Hepatocyte growth factor activator, Hepatocyte growth factor receptor, Hepatocyte nuclear factor 4, Histone 2A, Histone 28, HMG CoA reductase, Hydroxyacyl CoA dehydrogenase, Hydroxysteroid sulfotransferase a, Hypoxanthine-guanine phosphoribosyltransferase, ICE-rel 11 (Caspase 4), ICH-2 cysteine protease=CASPASE 4, IkB-a, Insulin-like growth factor binding protein 1, Insulin-like growth factor binding protein 2, Insulin-like growth factor binding protien 3, Insulin-like growth factor I, Insulin-like growth factor 11, Integrin alpha, Integrin alpha L, Integrin betas, Integrin beta2, Intercellular adhesion molecule-1, Intercellular adhesion molecule-2, Intercellular adhesion molecule-3, Interferon gamma, Interferon inducible protein 10, Interferon inducible protein 15, Interleukin-1 alpha, Interleukin-12, Interleukin-2, Interleukin-4, Interleukin-5, Interleukin-6, Involucrin, JNK1 stress activated protein kinase, K-cadherin, Ki67, Lactate Dehydrogenase 8, Lactoferrin, Lipopolysaccharide binding protein, Lipoprotein lipase precursor, Liver fatty acid binding protein, L-myc, Low density lipoprotein receptor, Luteinizing hormone, Lysyl oxidase, Macrophage inflammatory protein-1 alpha, Macrophage inflammatory protein-1 beta, Macrophage inflammatory protein-2 alpha, Macrophage inflammatory protein-2 beta, Macrophage inflammatory protein-3 alpha, Macrophage inflammatory protein-3 beta, Malic enzyme, MAP kinase kinase, Matrix metal loproteinasel, Matrix metal loproteinase-2, MDM-2, MET proto-oncogene, Metallothionein 1, Metallothionein 2, Metallothionein 3, Metallothionein IA, Metallothionein IG, Metalregulatory transcription factor-1, Mitogen activated protein kinase (P38), Mitogen inducible gene (mig-2), MOAT-B (MRP/organic anion transporter), Monoamine oxidase A, Monoamine oxidase B, Multidrug resistance-associated protein, Multidrug resistant protein-1, Multidrug resistant protein-2, Multidrug resistant protein-3=cMOAT2, MUTL homologue (MLH1), MutS Homologue (MSH2), Myeloid cell differentiation protein-1, Na/taurocholate cotransporting polypeptide, NADPH cytochrome P450-oxidoreductase, NADPH cytochrome P450 reductase, NADPH quinone oxidoreductase-1 (DTDiaphorase), Natural killer cell-enhancing factor B, N-cadherin, NF-kappaB (p65), Nitric oxide synthase-1, inducible, Nucleoside diphosphate kinase beta isoform, 0-6-alkylguanine-DNAalkyltransferase, OBcadherin 1, OB-cadherin 2, Octamer binding protein 1, Octamer binding protein 2, Octamer binding protein 3, Oncostatin M, Organic anion transporter 1, Organic anion transporter 3, Organic anion transporter K1, Organic anion transporting polypeptide 1, Organic cation transporter 1, Organic cation transporter 2, Organic cation transporter 3, Organic cation transporter N1, Organic cation transporter N2, Ornithine decarboxylase, Osteopontin, Oxygen regulated protein 150, p53, PAPS synthetase, P-cadherin, PEGS (progression elevated gene 3), Peroxisomal 3-ketoacyl-CoA thiolase 1, Peroxisomal 3-ketoacylCoA thiolase 2, Peroxisomal acyl-CoA oxidase, Peroxisomal fatty acyl-CoA oxidase, Peroxisome assembly factor 1, Peroxisome assembly factor 2, Peroxisome biogenesis disorder protein-1, Peroxisome biogenesis disorder protein-11, Peroxisome biogenesis disorder protein-4, Peroxisome hydratase, Peroxisome proliferator activated receptor alpha, Peroxisome proliferator activated receptor gamma, Phenol sulfotransferase, Phosphoenolpyruvate carboxykinase, Phosphoglyceride kinase, Phospholipase A2, Plasminogen activator inhibitor 2, Platelet derived growth factor B, Platelet/endothelial cell adhesion molecule-1, Poly (ADP ribose) polymerase, Proliferating cell nuclear antigen gene, Prostaglandin H synthase, Protein kinase C betal, Protein-tyrosine phosphatase, Putative protein tyrosine phosphatase, RAID, RAID 51 homologue, RANTES, Ref 1, Replication factor C, 40-kDa subunit (A1), Replication protein A (70 kDa subunit), Retinoblastoma, Retinoblastoma related protein (P 107), Retinoid X receptor alpha, Retinoid X receptor beta, Retinoid X receptor gamma, Ribonucleotide reductase M1 subunit, Ribosomal protein L13A, Ribosomal protein S9, RNA-dependent helicase, ROAT1 (renal organic anion transporter), Serum amyloid A1, Serum amyloid A2alpha, Sister of p-glycoprotein, Sodium/bile acid cotransporter, Sonic hedgehog gene, SQM1, Superoxide Dismutase Cu/Zn, Superoxide dismutase Mn, T-cell cyclophilin, Tenascin, Thiopurine methyltransferase, Thioredoxin, Thrombospondin 2, Thymidine kinase, Thymidylate synthase, Thymosin beta-10, Tissue inhibitor of metalloproteinases-1, Tissue transglutaminase, Transcription factor IID, Transferrin, Transforming growth factor-beta 3, Tumor necrosis factor associated factor 2 (TRAF2), Tumor necrosis factor receptor 1, Tumor necrosis factor receptor 2, Tumor necrosis factor receptor-1 associated protein (TRADD), Tumor necrosis factor-alpha, Tumor necrosis factor beta, Type 1 interstitial collagenase, Tyrosine aminotransferase, Tyrosine protein kinase receptor (UFO), Ubiquitin, Ubiquitin conjugating enzyme (Rad 6 homologue), Ubiquitin-homology domain protein PIC1, UDPglucuronosyltransferase 1, UDP-glucuronosyltransferase 1A6, UDPglucuronosyltransferase 2, UDP-glucuronosyltransferase 28, Uncoupling protein 1, Uncoupling protein 2, Uncoupling protein 3, Urate oxidase, UV excision repair protein RAD 23 (XP-C), Vascular cell adhesion molecule 1 (VCAM-1), Vascular endothelial growth factor, Vascular endothelial growth factor D, Very long-chain acyl-CoA dehydrogenase, Vimentin, Vitellogenin, Wafl, XRCC1 (DNA repair protein).

Passenger genes also include genes encoding prodrug-activating enzymes such as viral thymidine kinase, viral thymidine phosphorylase, cytosine deaminase, bacterial carboxypeptidase G2, cytochrome P450 proteins, carboxylesterase, deoxycytidine kinase, nitroreductase, purine nucleoside phosphorylase, horseradish peroxidase, and xantine guanine phosphoribosyl transferase. Also included are genes encoding "proteotoxins" such as diphtheria toxin and cytolethal distending toxin.

The present invention, thus generally described, may be understood more readily by reference to the following examples, which are provided by way of illustration and are not intended to be limiting of the present invention.

EXAMPLES

Example 1

Construction of a Conditionally Replicating Adenovirus Pair of the Invention Using a Heat-Activated, Mifepristone-Dependent Gene Switch Adenovirus is abbreviated Ad below. Generally known molecular biology and biochemistry methods are used. Molecular biology methods are described, e.g., in "Current protocols in molecular biology, Ausubel et al., eds., volumes 1-4, John Wiley and Sons, Inc. ISBN 0-471-50338-X.
Recombinant Adenovirus 1 (rAd1)

Recombinant adenovirus 1 lacks nucleotides 28,130-30,820 encompassing E3. Nucleotide numbers relating to the adenovirus type 5 genome are as defined in G1: 33694637. Davison et al. 2003. J. Gen. Virol. 84, 2895-2908. Further, E1A promoter and E4 promoter sequences are replaced with a GAL4 site-containing minimal promoter. According to the convention followed elsewhere in this specification, rAd1 corresponds to a second virus of a conditionally replicating virus pair of the invention.

The simplified system for generating recombinant adenovirus developed by He et al. (Proc. Natl. Acad. Sci. USA 95, 2509-2514 (1998)) was employed to construct rAd1 (rAd2). This system was made available commercially by Stratagene Corp. of La Jolla, Calif. A manual entitled "AdEasy™ Adenoviral Vector System" (revision no. 060002) is distributed by the Company to its customers and is also available at the Company's website.

Mutagenesis was carried out in transfer vector pShuttle (He et al. 1998. Proc. Natl. Acad. Sci. USA 95, 2509-2514) distributed by Statagene Corporation. FIG. 7 presents the complete nucleotide sequence of this plasmid. According to Stratagene's manual entitled "AdEasy™ Adenoviral Vector System" (revision no. 060002), pShuttle contains the following adenovirus sequence elements: left inverted terminal repeat, encapsidation signal (Ad 1-331), "right arm homology region" (3, 534-5790), "left arm homology region" (34, 931-35,935) and right inverted terminal repeat. A site-directed mutagenesis procedure, the so-called QuikChange$^R$ procedure of Stratagene Corp. that makes use of the polymerase chain reaction (PCR) was employed to delete E4 promoter sequences present in the left arm homology region of pShuttle (Ad 35,586-35,808) and replace them by an NheI restriction site. The QuikChange protocol is described, for example, in instruction manual "QuikChange XL site-directed mutagenesis kit" (revision no. 063003) published by Stratagene Corp. at their website and distributed to customers by mail. A related procedure is described briefly in Guettouche, T. (2002). Ph.D. Thesis, University of Miami, Miami, Fla. The resulting construct was labeled "pShuttle-Nhe".

A GAL4-binding site-containing minimal promoter was inserted into the NheI site of pShuttle-Nhe. To achieve this, a DNA fragment encompassing nucleotides 7677 to 323 of plasmid pGene/V5-His (Invitrogen Corporation of Carlsbad, Calif.) not including a complete PacI site was PCR-amplified using appropriate primers also containing an NheI restriction site. After digestion of the PCR fragment with NheI, it was ligated to NheI-digested pShuttle-Nhe DNA. Recombinants were identified by restriction digestion and nucleotide sequencing. Based on restriction analysis and nucleotide sequencing results, a clone was selected in which the inserted promoter sequence was correctly oriented relative to the E4 sequences in the left arm homology region of pShuttle-Nhe. This plasmid was named pShuttle-Nhe-GAL. The nucleotide sequence of pGene/V5-His is provided in FIG. 8. The plasmid is also described in instruction manual "GeneSwitch TM System, Version B, 000829/25-0313" of Invitrogen Corp. that is distributed by the Company to its customers and is also available at the Company's website.

Next, the right arm homology region of pShuttle-Nhe-GAL was replaced with Ad sequences also containing the beginning of the E1 region in addition to the homology region. First, pShuttle-Nhe-GAL was digested with BglII and PmeI, filled in with DNA polymerase Klenow fragment and religated to produce pShuttle-Nhe-GAL-delE1. The latter plasmid lacked the right arm homology region. Next, a fragment containing Ad 496-5780 was obtained by PCR amplification from plasmid pXC 1 (Microbix Corporation, Toronto, Oreg.). The nucleotide sequence of this plasmid is presented as FIG. 9. The latter PCR amplification was carried out using a forward primer (reading into the E1 gene) containing AscII and NotI restriction sites and a reverse primer containing a NotI restriction site. After digestion with NotI, the PCR fragment was ligated to NotI-digested pShuttle-Nhe-GAL-delE1 DNA to produce plasmid pShuttle-Nhe-GAL-E1. A clone was chosen in which the orientation of the inserted E1 sequence was the same as that of the substituted truncated E1 sequence. In a subsequent subcloning step, a DNA fragment encompassing nucleotides 7677 to 323 of plasmid pGene/V5-His was PCR-amplified using appropriate primers also containing an AscII restriction site. After digestion of the PCR fragment with AscII, it was ligated to AscII-digested pShuttle-Nhe-GAL-E1 DNA. Recombinants were identified by restriction digestion and by nucleotide sequencing. Based on restriction analysis and nucleotide sequencing information, a clone was selected that contained the inserted pGene/V5-His promoter sequence in the correct orientation relative to the E1 sequences. This clone was named pShuttle-Nhe-GAL-E1-GAL. Finally, the NotI site next to the inserted GAL4 site-containing promoter (inserted pGene/V5-His promoter sequence) was deleted by QuikChange mutagenesis. As a consequence, the resulting construct pShuttle-Nhe-GAL-E1-GAL-delNot contained a unique NotI site situated immediately downstream from the E1 sequences. To prepare recombinant Ad, pShuttle-Nhe-GAL-E1-GAL-delNot DNA was linearized by NotI digestion and was co-electroporated with pAdEasy-1 DNA (He et al. 1998. Proc. Natl. Acad. Sci. USA 95, 2509-2514) into *E. coli* BJ5183 cells. BJ5183 cells (Stratagene catalog no. 200154) have the cellular components necessary to carry out homologous recombination between introduced viral sequences. Detailed methods for the generation of recombinant Ad plasmids and the subsequent production of recombinant Ad viruses are discussed in He et al. (Proc. Natl. Acad. Sci. USA 95, 2509-2514 (1998)) and in Stratagene manual "AdEasy™ Adenoviral Vector System" (revision no. 060002). Briefly, recombinant Ad plasmids were characterized by restriction digestion. After preparation of a sufficient amount of DNA of a correct recombinant, the DNA was digested with PacI to separate plasmid sequences and inserted sequences comprising the Ad sequences. To produce recombinant Ad, the digested DNA was transfected into 293E4pIX cells. 293E4pIX cells are 293 cells containing an MMTV promoter-driven E4 transcription unit. In the presence of dexamethasone, these cells provide both E1 and E4 functions that were needed to amplify the desired recombinant virus that has conditionally active E1A and E4 genes. Using standard technology (briefly described in He et al.; see also Graham and Prevec. 1991. Manipulation of adenovirus vectors. In: Methods in Molecular Biology, Gene Transfer and Expression Protocols, vol. 7, ed. Murray, The Humana Press Inc., Clifton, N.J., pp. 109-127), virus plaques were isolated, and rAd1 stocks were prepared. Viral stocks can be purified by CsCl gradient centrifugation or chromatographic procedures.

Note that pAdEasy-1 contains all Ad sequences except for nucleotides 1-3,533 and 28,130-30,820. Hence, rAd1 (and rAd2, described below) contains a deletion of a nonessential E3 region. By using an Ad plasmid that contains all E3 sequences in the recombination step, a recombinant Ad1 version that has a complete E3 region could be obtained.

Recombinant Adenovirus 2 (rAd2)

Recombinant adenovirus 2 is an E1/E3/E4-deleted Ad (lacking Ad 1-3,533, 28,130-30,820 and 35,586-35,808) that contains a transactivator that is closely related to transactivator GLVP described before. The transactivator employed in this example is a GAL4 DNA-binding domain-modified human progesterone receptor ligand-binding domain-human p65 activation domain chimera (GLP65) that was retrieved from plasmid pSwitch (Invitrogen Corp.). The complete sequence of pSwitch is shown in FIG. 10. The transactivator is activated by estrogen antagonist mifepristone. In rAd2, the transactivator gene is functionally linked to an hsp70B-GAL4 tandem promoter. Optionally, rAd2 may also contain a passenger gene that is regulated by the hsp70B-GAL4 tandem promoter or another promoter. According to the convention followed elsewhere in this specification, rAd2 corresponds to a first virus of a conditionally replicating virus pair of the invention. Construction of an hsp70-GAL4 tandem promoter. Plasmid hsp70-fLuc was obtained by subcloning promoter and RNA leader sequences of the human Hsp70B gene from OR173 into a plasmid containing a firefly luciferase gene. Voellmy et al. 1985. Proc. Natl. Acad. Sci. USA 82, 4949-4953. Hsp70-fLuc contains more than 2 kbp of hsp70B gene nontranscribed sequence. A short fragment of about 460 by can be removed from the latter sequence using restriction enzymes BamHI and HindIII that will contain the essential promoter sequence (about 350 bp) that includes the three functionally important heat shock element sequences, the Hsp70B transcription start site and an about 110 bp-long transcribed sequence (RNA leader region). Voellmy et al. 1985. Proc. Natl. Acad. Sci. USA 82, 4949-4953. Schiller et al. 1988. J. Mol. Biol. 203, 97-105.

To prepare hsp70-GAL4-fLuc, an SgfI site was inserted in the hsp70B 5' untranslated region present in hsp70-fLuc by the QuikChange procedure (Stratagene) using primer 5'-CAGCCTCCGTGGCCTCGCGATCGCAG-CATCCGACAAGAAGC (SEQ ID NO: 5) and its complement (hsp70-GAL4-fLuc/Sgf). A short intron sequence (about 245 bp) was PCR-amplified from construct RL-CMV (Promega) using primers 5% TATGCGATCGCTTCTGA-CACAACAGTCTCG (SEQ ID NO: 6) and 5% TATGC-GATCGCCTTAAGAGCTGTAATTGAAC (SEQ ID NO: 7), digested with SgfI and ligated to SgfI-digested hsp70-GAL4-fLuc/Sgf. Resulting construct hsp70-GAL4-fLuc/Sgf/Int served as template in a QuikChange reaction designed to introduce an AscI restriction site into the intron sequence (hsp70-GAL4-fLuc/Sgf/Int/Asc). Primers employed were 5'-TATGGCGCGCCACCTGACGTCGACGG (SEQ ID NO: 8) and 5'-ATAGGCGCGCCGGTAAGCTTAAGT-TAAACGCTAGC (SEQ ID NO: 9). Finally, a sequence (about 450 bp) containing a minimal GAL4 promoter was PCR-amplified from construct GeneV5-HisA (Invitrogen) using primers 5'-TATGGCGCGCCTCGACGGATCGG-GAGATC (SEQ ID NO: 10) and 5% TATGGCGCGCCTGT-TAATTAACACGGGG (SEQ ID NO: 11), digested with AscI and ligated to AscI-cut hsp70-GAL4-fLuc/Sgf/Int/Asc DNA, yielding hsp70-GAL4-fLuc.

For the construction of hsp70-GAL4-GLP65, a QuikChange reaction using primer 5'-CGAGTCTA-GAGATATCGAATCAGGCGCGCCTTGTC-GACTCGAAGATCTG (SEQ ID NO: 12) and its complement was performed to insert an AscI site downstream of the multicloning site of construct Shuttle (Stratagene). The resulting construct was named A1. A glp65 gene fragment was PCR-amplified from construct Switch (Invitrogen) using primers 5'-TATTCTAGAACCAAGCTACCGGTCCACC (SEQ ID NO: 13) and 5'-ATAGGCGCGCCTCAGAAGC-CATAGAGCCC (SEQ ID NO: 14), digested with AscI and XbaI, and ligated to AscI/XbaI-cut A1 DNA to produce construct IA. Finally, an hsp70-GAL4 promoter cassette was excised from hsp70-GAL-fLuc using BamHI and HindIII. The filled promoter cassette fragment was ligated to XbaI-digested and filled construct 1A DNA. To construct GAL4-fLuc, a HindIII(filled)-XhoI fragment from 17×4 TATA CAT including a GAL4-responsive promoter was inserted in between the SmaI and XhoI sites of GL2B (Promega Corp.). For a description of construct 17×4 TATA CAT see Wang et al. 1997. Nat. Biotechnol. 15, 239-243; Wang et al. 1997. Gene Therapy 4, 432-441.

The gene switch consisting of hsp70-GAL4-GLP65 and the GLP65-responsive GAL4 promoter of construct GAL4-fLuc was tested extensively in transient transfection experiments, stable cell lines containing the gene switch as well as animal experiments in which hsp70-GAL4-GLP65 and GAL4-fLuc were introduced in gastrocnemius muscles of mice by injection and in vivo electroporation. Collectively, these experiments demonstrated that the activity of target gene fLuc was stringently regulated by the gene switch in vitro and in vivo. fLuc expression was strongly induced in cells that were heat-treated and exposed to mifepristone. Essentially no activity was measured in cells that were left untreated, were heat-treated only, or were only exposed to mifepristone in the absence of a heat treatment. Induced activity remained high for at least one weak after a single, transient activating heat treatment in the continued presence of mifepristone. Mifepristone removal resulted in deactivation of the gene switch.

Several derivatives of hsp70-GAL4-GLP65 constructs were also prepared and used for construction of different versions of rAd2. A preferred construct that displays a particularly low background level of transactivation ability in the absence of heat activation and mifepristone is Hsp70/GAL4-GLP65-RKC. In this construct, the Kozak consensus sequence of the glp65 gene was mutated to reduce translation initiation efficiency, and nontranslated sequences 3' of the GLP65-coding sequence were removed. Intermediary construct hsp70-GAL4-GLP65-34C was prepared by QuikChange mutagenesis of Hsp70-GAL4-GLP65, using oligonucleotide 5'-ACCAAGCTACCGGTCCTCCATG-TACTCCCAGCAGCCAGATCTGAAGC-3' (SEQ ID NO: 15) and its complement as primers. For obtaining hsp70-GAL4-GLP65-RKC, the hsp70-GAL4-GLP65-34C gene was PCR-amplified using primers 5'-ATACCTAGGCG-GATCCGACCTCCCACAGC (SEQ ID NO: 16) and 5'-AT-AGCGGCCGCCCGGAGGATCCTTAGGAGC (SEQ ID NO: 17), digested with AvrII and NotI, and ligated to NotI/XbaI-digested vector Shuttle. All subcloning and mutagenesis steps were monitored by restriction analysis and nucleotide sequencing.

To prepare the actual shuttle constructs used in the construction of different versions of rAd2, the hsp70B-GAL4-GLP65 gene cassette and derivative genes including hsp70-GAL4-GLP65-RKC were PCR-amplified and inserted into the multicloning site of pShuttle-Nhe (described under rAd1). The counterclockwise orientation of the genes in the resulting constructs was verified by restriction analysis and nucleotide sequencing. Constructs were named SNPB3DE4xGAL-3 (hsp70B-GAL4-GLP65), or SNKC6DE4xGAL-7 (hsp70-GAL4-GLP65-RKC). The same designations are also used to identify particular rAd2s.

It is noted that the above shuttle constructs may also include a passenger gene such as, for example, an it 12 gene. IL12-coding sequences and 3' untranslated sequences could be PCR-amplified from an appropriate construct. This PCR fragment and a fragment containing the hsp70B-GAL4 tandem promoter could be inserted in the multicloning site next to the transactivator cassette. Nucleotide sequence analysis could be used to verify that the hsp70-GAL4 promoter is properly situated to control transcription from the il12 gene. Alternatively, a single tandem promoter may be used to control glp65 and il12 gene activity. In this case the sequence of elements inserted in pShuttle-Nhe could be as follows: hsp70B-GAL4 tandem promoter—il12 gene—internal ribosome binding site—glp65 gene—3' untranslated sequences. Attention should be paid to the positioning of a passenger gene that is regulated by a constitutively active promoter. In such a case, a passenger gene cassette should be inserted downstream from the glp65 gene or in an orientation that results in an opposite transcriptional direction from that of the glp65 gene. It is noted further that any passenger gene and associated 3' untranslated sequences to be incorporated in an rAd2 need to be screened for the presence of PmeI and PacI sites. If such sites are present, they need to be deleted. Deletion can typically be achieved conveniently by using the QuikChange mutagenesis procedure.

To prepare rAd2 (virus), constructs SNPB3DE4xGAL-3 and SNKC6DE4xGAL-7 were linearized with PmeI and co-introduced with AdEasy-1 sequences in an appropriate *E. coli* strain to achieve homologous recombination of viral sequences. Isolation of correct recombinant plasmids, preparation of sufficient amounts of plasmids, digestion with PacI, transfection into 293 cells expressing E4, and isolation of rAd2 viruses were as described before for rAd1.

Example 2

Demonstration of Conditional Replication of a rAd1/rAd2 Virus Pair of the Invention Parallel, subconfluent, adherent cultures of human HeLa cells grown under standard conditions were infected with a rAd1/rAd2 (SNPB3DE4xGAL-3) combination at a total multiplicity of infection of about 0.1. rAd1/rAd2 ratio in this particular experiment was 5:1. Medium was changed one day after infection, and cultures were either heat-treated at 42° C. for 2 h or not treated and then cultured for 8 days in the presence or absence of 10 nM mifepristone. Cells were diluted (split) once about halfway through the incubation period. At the end of the 8-day incubation, cells were fixed and stained using anti-hexon protein antibody. Results revealed readily detectable spreading of virus through cultures that had been heat-treated and postincubated in the presence of mifepristone but not through cultures that had not been heat-treated or had not received mifepristone.

Example 3

Demonstration of Oncolytic Action of a rAd1/rAd2 Virus Pair of the Invention Parallel, subconfluent, adherent cultures of human HeLa cells grown under standard conditions were infected with a rAd1/rAd2 (SNPB3DE4xGAL-3) combination at a total multiplicity of infection of about 25. rAd1/rAd2 ratio in this particular experiment was 1:1. Cultures were either heat-treated at 43° C. for 2 h or not treated and then cultured for 4 days in the presence or absence of 10 nM mifepristone. At the end of this period, cells were stained with crystal violet, and cell numbers were estimated. Quantitative killing of cells was observed only in cultures that had been heat-treated and exposed to mifepristone.

All references cited in this application, including publications, patents and patent applications, shall be considered as having been incorporated in their entirety.

---

The invention claimed is:

1. A modified, conditionally replicating virus whose genome includes a gene switch that controls the expression of a viral gene required for efficient replication of the modified virus, wherein the gene switch comprises (1) a gene for a small-molecule-activated transactivator that is functionally linked to a nucleic acid sequence that acts as a heat shock promoter and (2) a promoter that is responsive to the transactivator and is functionally linked to the viral gene required for efficient replication and the gene switch is activated in a cell infected by the modified virus upon exposure of the cell to heat sufficient to activate the heat shock promoter and to the small-molecule activator.

2. The modified virus of claim 1, wherein the viral genome further includes a passenger gene.

3. The modified virus of claim 1, wherein the virus is a member of a family selected from the group consisting of Adenoviridae, Herpesviridae, and Retroviridae.

4. The modified virus of claim 1, wherein the virus is an adenovirus.

5. The modified virus of claim 1, wherein the gene switch controls the expression of a viral gene encoding a viral protein selected from the group consisting of E1A, E1B and E4.

6. The modified virus of claim of claim 1, wherein the gene for the small-molecule-activated transactivator is functionally linked to a nucleic acid sequence that acts as a heat shock promoter as well as a transactivator-responsive promoter.

7. The modified virus of claim 6, wherein the viral genome further includes a passenger gene.

8. The modified virus of claim 6, wherein the virus is a member of a family selected from the group consisting of Adenoviridae, Herpesviridae, and Retroviridae.

9. The modified virus of claim 6, wherein the virus is an adenovirus.

10. The modified virus of claim 6, wherein the gene switch controls the expression of a viral gene encoding a viral protein selected from the group consisting of E1A, E1B and E4.

* * * * *

SEQUENCE LISTING

```
<160> NUMBER OF SEQ ID NOS: 17

<210> SEQ ID NO 1
<211> LENGTH: 6621
<212> TYPE: DNA
<213> ORGANISM: Artificial Sequence
<220> FEATURE:
<223> OTHER INFORMATION: Plasmid pShuttle, Stratagene Corp. La Jolla,
      CA

<400> SEQUENCE: 1
catcatcaat aatatacctt attttggatt gaagccaata tgataatgag ggggtggagt      60
ttgtgacgtg gcgcggggcg tgggaacggg gcgggtgacg tagtagtgtg gcggaagtgt     120
gatgttgcaa gtgtggcgga acacatgtaa gcgacggatg tggcaaaagt gacgtttttg     180
gtgtgcgccg gtgtacacag gaagtgacaa ttttcgcgcg gttttaggcg gatgttgtag     240
taaatttggg cgtaaccgag taagatttgg ccattttcgc gggaaaactg aataagagga     300
agtgaaatct gaataatttt gtgttactca tagcgcgtaa tactggtacc gcggccgcct     360
cgagtctaga gatatcgaat tcaagcttgt cgactcgaag atctgggcgt ggttaagggt     420
gggaaagaat atataaggtg ggggtcttat gtagttttgt atctgttttg cagcagccgc     480
cgccgccatg agcaccaact cgtttgatgg aagcattgtg agctcatatt tgacaacgcg     540
catgccccca tgggccgggg tgcgtcagaa tgtgatgggc tccagcattg atggtcgccc     600
cgtcctgccc gcaaactcta ctaccttgac ctacgagacc gtgtctggaa cgccgttgga     660
gactgcagcc tccgccgccg cttcagccgc tgcagccacc gcccgcggga ttgtgactga     720
ctttgctttc ctgagcccgc ttgcaagcag tgcagcttcc cgttcatccg cccgcgatga     780
caagttgacg gctcttttgg cacaattgga ttctttgacc cgggaactta atgtcgtttc     840
tcagcagctg ttggatctgc gccagcaggt ttctgccctg aaggcttcct ccctcccaa     900 tgcggtttaa acataaaata aaaaccaga ctctgtttgg atttggatca agcaagtgtc     960
ttgctgtctt tatttagggg ttttgcgcgc gcggtaggcc cggaccagc ggtctcggtc    1020 gttgagggtc ctgtgtattt tttccaggac gtggtaaagg tgactctgga tgttcagata    1080
catgggcata agcccgtctc tggggtggag gtagcaccac tgcagagctt catgctgcgg    1140
```

```
ggtggtgttg tagatgatcc agtcgtagca ggagcgctgg gcgtggtgcc taaaaatgtc     1200
tttcagtagc aagctgattg ccaggggcag gcccttggtg taagtgttta caaagcggtt     1260
aagctgggat gggtgcatac gtggggatat gagatgcatc ttggactgta tttttaggtt     1320
ggctatgttc ccagccatat ccctccgggg attcatgttg tgcagaacca ccagcacagt     1380
gtatccggtg cacttgggaa atttgtcatg tagcttagaa ggaaatgcgt ggaagaactt     1440
ggagacgccc ttgtgacctc caagattttc catgcattcg tccataatga tggcaatggg     1500
cccacgggcg gcggcctggg cgaagatatt tctgggatca ctaacgtcat agttgtgttc     1560
caggatgaga tcgtcatagg ccattttttac aaagcgcggg cggagggtgc cagactgcgg     1620
tataatggtt ccatccggcc caggggcgta gttaccctca cagatttgca tttcccacgc     1680
tttgagttca gatgggggga tcatgtctac ctgcggggcg atgaagaaaa cggtttccgg     1740
ggtaggggag atcagctggg aagaaagcag gttcctgagc agctgcgact taccgcagcc     1800
ggtgggcccg taaatcacac ctattaccgg gtgcaactgg tagttaagag agctgcagct     1860
gccgtcatcc ctgagcaggg gggccacttc gttaagcatg tccctgactc gcatgttttc     1920
cctgaccaaa tccgccagaa ggcgctcgcc gcccagcgat agcagttctt gcaaggaagc     1980 aaagttttt aacggtttga ccgtccgc cgtaggcatg cttttgagcg tttgaccaag       2040
cagttccagg cggtcccaca gctcggtcac ctgctctacg gcatctcgat ccagcatatc    2100
tcctcgtttc gcgggttggg gcggctttcg ctgtacggca gtagtcggtg ctcgtccaga    2160
cgggccaggg tcatgtcttt ccacgggcgc agggtcctcg tcagcgtagt ctgggtcacg    2220
gtgaaggggt gcgctccggg ctgcgcgctg gccagggtgc gcttgaggct ggtcctgctg    2280
gtgctgaagc gctgccggtc ttcgccctgc gcgtcggcca ggtagcattt gaccatggtg    2340
tcatagtcca gcccctccgc ggcgtggccc ttggcgcgca gcttgccctt ggaggaggcg    2400
ccgcacgagg ggcagtgcag acttttgagg gcgtagagct tgggcgcgag aaataccgat    2460
tccggggagt aggcatccgc gccgcaggcc ccgcagacgg tctcgcattc cacgagccag    2520
gtgagctctg gccgttcggg gtcaaaaacc aggtttcccc catgcttttt gatgcgtttc    2580
ttacctctgg tttccatgag ccggtgtcca cgctcggtga cgaaaaggct gtccgtgtcc    2640
ccgtatacag acttgagagg gagttttaaac gaattcaata gcttgttgca tgggcggcga    2700
tataaaatgc aaggtgctgc tcaaaaaatc aggcaaagcc tcgcgcaaaa aagaaagcac    2760
atcgtagtca tgctcatgca gataaaggca ggtaagctcc ggaaccacca cagaaaaaga    2820
caccattttt ctctcaaaca tgtctgcggg tttctgcata aacacaaaat aaaataacaa    2880
aaaaacattt aaacattaga agcctgtctt acaacaggaa aaacacccct tataagcata    2940
agacggacta cggccatgcc ggcgtgaccg taaaaaaact ggtcaccgtg attaaaaagc    3000
accaccgaca gctcctcggt catgtccgga gtcataatgt aagactcggt aaacacatca    3060
ggttgattca tcggtcagtg ctaaaaagcg accgaaatag cccgggggaa tacatacccg    3120
caggcgtaga gacaacatta cagcccccat aggaggtata acaaaattaa taggagagaa    3180
aaacacataa acacctgaaa aaccctcctg cctaggcaaa atagcaccct cccgctccag    3240
aacaacatac agcgcttcac agcggcagcc taacagtcag ccttaccagt aaaaagaaa     3300 acctattaaa aaaacaccac tcgacacggc accagctcaa tcagtcacag tgtaaaaaag    3360
ggccaagtgc agagcgagta tatataggac taaaaaatga cgtaacggtt aaagtccaca    3420
aaaaacaccc agaaaccgcc acgcgaacct acgcccagaa acgaaagcca aaaaacccac    3480
aacttcctca aatcgtcact tccgtttttcc cacgttacgt aacttcccat tttaagaaaa    3540
```

```
ctacaattcc caacacatac aagttactcc gccctaaaac ctacgtcacc cgccccgttc    3600
ccacgccccg cgccacgtca caaactccac cccctcatta tcatattggc ttcaatccaa    3660
aataaggtat attattgatg atgttaatta acatgcatgg atccatatgc ggtgtgaaat    3720
accgcacaga tgcgtaagga gaaaataccg catcaggcgc tcttccgctt cctcgctcac    3780
tgactcgctg cgctcggtcg ttcggctgcg gcgagcggta tcagctcact caaaggcggt    3840
aatacggtta tccacagaat caggggataa cgcaggaaag aacatgtgag caaaaggcca    3900
gcaaaaggcc aggaaccgta aaaaggccgc gttgctggcg ttttttccata ggctccgccc    3960 ccctgacgag catcacaaaa atcgacgctc aagtcagagg tggcgaaacc cgacaggact    4020
ataaagatac caggcgtttc ccctggaag ctccctcgtg cgctctcctg ttccgaccct    4080
gccgcttacc ggatacctgt ccgcctttct cccttcggga agcgtggcgc tttctcatag    4140
ctcacgctgt aggtatctca gttcggtgta ggtcgttcgc tccaagctgg gctgtgtgca    4200 cgaaccccc gttcagcccg accgctgcgc cttatccggt aactatcgtc ttgagtccaa    4260
cccggtaaga cacgacttat cgccactggc agcagccact ggtaacagga ttagcagagc    4320
gaggtatgta ggcggtgcta cagagttctt gaagtggtgg cctaactacg gctacactag    4380
aaggacagta tttggtatct gcgctctgct gaagccagtt accttcggaa aaagagttgg    4440
tagctcttga tccggcaaac aaaccaccgc tggtagcggt ggtttttttg tttgcaagca    4500
gcagattacg cgcagaaaaa aaggatctca agaagatcct ttgatctttt ctacggggtc    4560
tgacgctcag tggaacgaaa actcacgtta agggattttg gtcatgagat tatcaaaaag    4620
gatcttcacc tagatccttt taaattaaaa atgaagtttt aaatcaatct aaagtatata    4680
tgagtaaact tggtctgaca gttaccaatg cttaatcagt gaggcaccta tctcagcgat    4740
ctgtctattt cgttcatcca tagttgcctg actccccgtc gtgtagataa ctacgatacg    4800
ggagggctta ccatctggcc ccagtgctgc aatgataccg cgagacccac gctcaccggc    4860
tccagattta tcagcaataa accagccagc cggaagggcc gagcgcagaa gtggtcctgc    4920
aactttatcc gcctccatcc agtctattaa ttgttgccgg gaagctagag taagtagttc    4980
gccagttaat agtttgcgca acgttgttgc cattgctgca gccatgagat tatcaaaaag    5040
gatcttcacc tagatccttt tcacgtagaa agccagtccg cagaaacggt gctgaccccg    5100
gatgaatgtc agctactggg ctatctggac aagggaaaac gcaagcgcaa agagaaagca    5160
ggtagcttgc agtgggctta catggcgata gctagactgg gcggttttat ggacagcaag    5220
cgaaccggaa ttgccagctg gggcgccctc tggtaaggtt gggaagccct gcaaagtaaa    5280
ctggatggct ttcttgccgc caaggatctg atggcgcagg ggatcaagct ctgatcaaga    5340
gacaggatga ggatcgtttc gcatgattga acaagatgga ttgcacgcag gttctccggc    5400
cgcttgggtg gagaggctat tcggctatga ctgggcacaa cagacaatcg gctgctctga    5460
tgccgccgtg ttccggctgt cagcgcaggg gcgcccggtt ctttttgtca agaccgacct    5520
gtccggtgcc ctgaatgaac tgcaagacga ggcagcgcgg ctatcgtggc tggccacgac    5580
gggcgttcct tgcgcagctg tgctcgacgt tgtcactgaa gcgggaaggg actggctgct    5640
attgggcgaa gtgccggggc aggatctcct gtcatctcac cttgctcctg ccgagaaagt    5700
atccatcatg gctgatgcaa tgcggcggct gcatacgctt gatccggcta cctgcccatt    5760
cgaccaccaa gcgaaacatc gcatcgagcg agcacgtact cggatggaag ccggtcttgt    5820
cgatcaggat gatctggacg aagagcatca ggggctcgcg ccagccgaac tgttcgccag    5880
gctcaaggcg agcatgcccg acggcgagga tctcgtcgtg acccatggcg atgcctgctt    5940
```

| | | |
|---|---|---|
| gccgaatatc atggtggaaa atggccgctt ttctggattc atcgactgtg gccggctggg | 6000 | |
| tgtggcggac cgctatcagg acatagcgtt ggctacccgt gatattgctg aagagcttgg | 6060 | |
| cggcgaatgg gctgaccgct tcctcgtgct ttacggtatc gccgctcccg attcgcagcg | 6120 | |
| catcgccttc tatcgccttc ttgacgagtt cttctgaatt ttgttaaaat ttttgttaaa | 6180 | |
| tcagctcatt ttttaaccaa taggccgaaa tcggcaacat cccttataaa tcaaaagaat | 6240 | |
| agaccgcgat agggttgagt gttgttccag tttggaacaa gagtccacta ttaaagaacg | 6300 | |
| tggactccaa cgtcaaaggg cgaaaaaccg tctatcaggg cgatggccca ctacgtgaac | 6360 | |
| catcacccaa atcaagtttt tgcggtcga ggtgccgtaa agctctaaat cggaaccta | 6420 | |
| aagggagccc ccgatttaga gcttgacggg gaaagccggc gaacgtggcg agaaaggaag | 6480 | |
| ggaagaaagc gaaaggagcg ggcgctaggg cgctggcaag tgtagcggtc acgctgcgcg | 6540 | |
| taaccaccac acccgcgcgc ttaatgcgcc gctacagggc gcgtccattc gccattcagg | 6600 | |
| atcgaattaa ttcttaatta a | 6621 | |

<210> SEQ ID NO 2
<211> LENGTH: 7697
<212> TYPE: DNA
<213> ORGANISM: Artificial Sequence
<220> FEATURE:
<223> OTHER INFORMATION: Plasmid pGene/V5-His, Invitrogen Corp.,
      Carlsbad, CA

<400> SEQUENCE: 2

| | | |
|---|---|---|
| ccgagctctt acgcgggtcg aagcggagta ctgtcctccg agtggagtac tgtcctccga | 60 | |
| gcggagtact gtcctccgag tcgagggtcg aagcggagta ctgtcctccg agtggagtac | 120 | |
| tgtcctccga gcggagtact gtcctccgag tcgactctag agggtatata atggatctcg | 180 | |
| agatatcgga gctcgtttag tgaaccgtca gatcgcctgg agacgccatc cacgctgttt | 240 | |
| tgacctccat agaagacacc gggaccgatc cagcctccgc ggccgggaac ggtgcattgg | 300 | |
| aacgcgcatt cccccgtgtta attaacaggt aagtgtcttc ctcctgtttc cttcccctgc | 360 | |
| tattctgctc aaccttccta tcagaaactg cagtatctgt atttttgcta gcagtaatac | 420 | |
| taacggttct ttttttctct tcacaggcca ccaagcttgg taccgagctc ggatccacta | 480 | |
| gtccagtgtg gtggaattct gcagatcgaa acgatgatag atcccgtcgt tttacaacgt | 540 | |
| cgtgactggg aaaaccctgg cgttacccaa cttaatcgcc ttgcagcaca tcccccttc | 600 | |
| gccagctggc gtaatagcga agaggcccgc accgatcgcc cttcccaaca gttgcgcagc | 660 | |
| ctgaatggcg aatggcgctt tgcctggttt ccggcaccag aagcggtgcc ggaaagctgg | 720 | |
| ctggagtgcg atcttcctga ggccgatact gtcgtcgtcc cctcaaactg gcagatgcac | 780 | |
| ggttacgatg cgcccatcta caccaacgta acctatccca ttacggtcaa tccgccgttt | 840 | |
| gttcccacgg agaatccgac gggttgttac tcgctcacat ttaatgttga tgaaagctgg | 900 | |
| ctacaggaag gccagacgcg aattattttt gatggcgtta actcggcgtt tcatctgtgg | 960 | |
| tgcaacgggc gctgggtcgg ttacggccag gacagtcgtt tgccgtctga atttgacctg | 1020 | |
| agcgcatttt tacgcgccgg agaaaaccgc ctcgcggtga tggtgctgcg ttggagtgac | 1080 | |
| ggcagttatc tggaagatca ggatatgtgg cggatgagcg gcattttccg tgacgtctcg | 1140 | |
| ttgctgcata aaccgactac acaaatcagc gatttccatg ttgccactcg ctttaatgat | 1200 | |
| gatttcagcc gcgctgtact ggaggctgaa gttcagatgt gcggcgagtt gcgtgactac | 1260 | |
| ctacgggtaa cagtttcttt atggcagggt gaaacgcagg tcgccagcgg caccgcgcct | 1320 | |

```
ttcggcggtg aaattatcga tgagcgtggt ggttatgccg atcgcgtcac actacgtctg    1380
aacgtcgaaa acccgaaact gtggagcgcc gaaatcccga atctctatcg tgcggtggtt    1440
gaactgcaca ccgccgacgg cacgctgatt gaagcagaag cctgcgatgt cggtttccgc    1500
gaggtgcgga ttgaaaatgg tctgctgctg ctgaacggca agccgttgct gattcgaggc    1560
gttaaccgtc acgagcatca tcctctgcat ggtcaggtca tggatgagca gacgatggtg    1620
caggatatcc tgctgatgaa gcagaacaac tttaacgccg tgcgctgttc gcattatccg    1680
aaccatccgc tgtggtacac gctgtgcgac cgctacggcc tgtatgtggt ggatgaagcc    1740
aatattgaaa cccacggcat ggtgccaatg aatcgtctga ccgatgatcc gcgctggcta    1800
ccggcgatga gcgaacgcgt aacgcgaatg gtgcagcgcg atcgtaatca cccgagtgtg    1860
atcatctggt cgctggggaa tgaatcaggc cacggcgcta atcacgacgc gctgtatcgc    1920
tggatcaaat ctgtcgatcc ttcccgcccg gtgcagtatg aaggcggcgg agccgacacc    1980
acggccaccg atattatttg cccgatgtac gcgcgcgtgg atgaagacca gcccttcccg    2040
gctgtgccga atggtccat caaaaaatgg ctttcgctac ctggagagac gcgcccgctg    2100
atcctttgcg aatacgccca cgcgatgggt aacagtcttg gcggtttcgc taaatactgg    2160
caggcgtttc gtcagtatcc ccgtttacag ggcggcttcg tctgggactg ggtggatcag    2220
tcgctgatta aatatgatga aaacggcaac ccgtggtcgg cttacggcgg tgattttggc    2280
gatacgccga acgatcgcca gttctgtatg aacggtctgg tctttgccga ccgcacgccg    2340
catccagcgc tgacggaagc aaaacaccag cagcagtttt tccagttccg tttatccggg    2400
caaaccatcg aagtgaccag cgaataccctg ttccgtcata gcgataacga gctcctgcac    2460
tggatggtgg cgctggatgg taagccgctg gcaagcggtg aagtgcctct ggatgtcgct    2520
ccacaaggta acagttgat tgaactgcct gaactaccgc agccggagag cgccgggcaa    2580
ctctggctca cagtacgcgt agtgcaaccg aacgcgaccg catggtcaga gccgggcac    2640 atcagcgcct ggcagcagtg gcgtctggcg gaaaaacctca gtgtgacgct ccccgccgcg    2700
tcccacgcca tcccgcatct gaccaccagc gaaatggatt tttgcatcga gctgggtaat    2760
aagcgttggc aattaaccg ccagtcaggc tttctttcac agatgtggat tggcgataaa    2820
aaacaactgc tgacgccgct gcgcgatcag ttcacccgtg caccgctgga taacgacatt    2880
ggcgtaagtg aagcgacccg cattgaccct aacgcctggg tcgaacgctg gaaggcggcg    2940
ggccattacc aggccgaagc agcgttgttg cagtgcacgg cagatacact tgctgatgcg    3000
gtgctgatta cgaccgctca cgcgtggcag catcagggga aaaccttatt tatcagccgg    3060
aaaacctacc ggattgatgg tagtggtcaa atggcgatta ccgttgatgt tgaagtggcg    3120
agcgatacac cgcatccggc gcggattggc ctgaactgcc agctggcgca ggtagcagag    3180
cgggtaaact ggctcggatt agggccgcaa gaaaaactatc ccgaccgcct tactgccgcc    3240
tgttttgacc gctgggatct gccattgtca gacatgtata ccccgtacgt cttcccgagc    3300
gaaaacggtc tgcgctgcgg gacgcgcgaa ttgaattatg gcccacacca gtggcgcggc    3360
gacttccagt tcaacatcag ccgctacagt caacagcaac tgatggaaac cagccatcgc    3420
catctgctgc acgcggaaga aggcacatgg ctgaatatcg acggtttcca tatggggatt    3480
ggtggcgacg actcctggag cccgtcagta tcggcggaat tccagctgag cgccggtcgc    3540
taccattacc agttggtctg gtgtcaaaaa gcggccgctc gaggtcaccc attcgaaggt    3600
aagcctatcc ctaaccctct cctcggtctc gattctacgc gtaccggtca tcatcaccat    3660
caccattgag tttaaacccg ctgatcagcc tcgactgtgc cttctagttg ccagccatct    3720
```

```
gttgtttgcc cctccccgt gccttccttg accctggaag gtgccactcc cactgtcctt    3780
tcctaataaa atgaggaaat tgcatcgcat tgtctgagta ggtgtcattc tattctgggg    3840
ggtggggtgg ggcaggacag caaggggag gattgggaag acaatagcag gcatgctggg    3900
gatgcggtgg gctctatggc ttctgaggcg gaaagaacca gctggggctc taggggtat    3960
ccccacgcgc cctgtagcgg cgcattaagc gcggcgggtg tggtggttac gcgcagcgtg    4020
accgctacac ttgccagcgc cctagcgccc gctccttccg ctttcttccc ttcctttctc    4080
gccacgttcg ccggctttcc ccgtcaagct ctaaatcggg gctcccttt agggttccga    4140
tttagtgctt tacggcacct cgaccccaaa aaacttgatt agggtgatgg ttcacgtagt    4200
gggccatcgc cctgatagac ggttttcgc cctttgacgt tggagtccac gttctttaat    4260
agtggactct tgttccaaac tggaacaaca ctcaacccta tctcggtcta ttcttttgat    4320
ttataaggga ttttgccgat ttcggcctat tggttaaaaa atgagctgat taacaaaaa    4380
tttaacgcga attaattctg tggaatgtgt gtcagttagg gtgtggaaag tccccaggct    4440
ccccagcagg cagaagtatg caaagcatgc atctcaatta gtcagcaacc aggtgtggaa    4500
agtccccagg ctccccagca ggcagaagta tgcaaagcat gcatctcaat tagtcagcaa    4560
ccatagtccc gcccctaact ccgcccatcc cgcccctaac tccgcccagt tccgcccatt    4620
ctccgcccca tggctgacta attttttta tttatgcaga ggccgaggcc gcctctgcct    4680
ctgagctatt ccagaagtag tgaggaggct ttttggagg cctaggcttt tgcaaaaagc    4740
tcccgggagc ttgtatatcc attttcggat ctgatcagca cgtgttgaca attaatcatc    4800
ggcatagtat atcggcatag tataatacga caaggtgagg aactaaacca tggccaagtt    4860
gaccagtgcc gttccggtgc tcaccgcgcg cgacgtcgcc ggagcggtcg agttctggac    4920
cgaccggctc gggttctccc gggacttcgt ggaggacgac ttcgccggtg tggtccggga    4980
cgacgtgacc ctgttcatca gcgcggtcca ggaccaggtg gtgccggaca cacccctggc    5040
ctgggtgtgg gtgcgcggcc tggacgagct gtacgccgag tggtcggagg tcgtgtccac    5100
gaacttccgg gacgcctccg ggccggccat gaccgagatc ggcgagcagc cgtggggcg    5160
ggagttcgcc ctgcgcgacc cggccggcaa ctgcgtgcac ttcgtggccg aggagcagga    5220
ctgacacgtg ctacgagatt tcgattccac cgccgccttc tatgaaaggt tgggcttcgg    5280
aatcgttttc cgggacgccg gctggatgat cctccagcgc ggggatctca tgctggagtt    5340
cttcgcccac cccaacttgt ttattgcagc ttataatggt tacaaataaa gcaatagcat    5400
cacaaatttc acaaataaag catttttttc actgcattct agttgtggtt tgtccaaact    5460
catcaatgta tcttatcatg tctgtatacc gtcgacatct agctagagct tggcgtaatc    5520
atggtcatag ctgtttcctg tgtgaaattg ttatccgctc acaattccac acaacatacg    5580
agccggaagc ataaagtgta aagcctgggg tgcctaatga gtgagctaac tcacattaat    5640
tgcgttgcgc tcactgcccg ctttccagtc gggaaacctg tcgtgccagc tgcattaatg    5700
aatcggccaa cgcgcgggga gaggcggttt gcgtattggg cgctcttccg cttcctcgct    5760
cactgactcg ctgcgctcgg tcgttcggct gcggcgagcg gtatcagctc actcaaaggc    5820
ggtaatacgg ttatccacag aatcagggga taacgcagga aagaacatgt gagcaaaagg    5880
ccagcaaaag gccaggaacc gtaaaaaggc cgcgttgctg gcgttttttcc ataggctccg    5940
cccccctgac gagcatcaca aaaatcgacg ctcaagtcag aggtggcgaa acccgacagg    6000
actataaaga taccaggcgt ttccccctgg aagctccctc gtgcgctctc ctgttccgac    6060
cctgccgctt accggatacc tgtccgcctt tctcccttcg ggaagcgtgg cgctttctca    6120
```

-continued

```
tagctcacgc tgtaggtatc tcagttcggt gtaggtcgtt cgctccaagc tgggctgtgt     6180
gcacgaaccc cccgttcagc ccgaccgctg cgccttatcc ggtaactatc gtcttgagtc     6240
caacccggta agacacgact tatcgccact ggcagcagcc actggtaaca ggattagcag     6300
agcgaggtat gtaggcggtg ctacagagtt cttgaagtgg tggcctaact acggctacac     6360
tagaagaaca gtatttggta tctgcgctct gctgaagcca gttaccttcg gaaaaagagt     6420
tggtagctct tgatccggca aacaaaccac cgctggtagc ggttttttg tttgcaagca     6480 gcagattacg cgcagaaaaa aaggatctca agaagatcct ttgatctttt ctacggggtc     6540
tgacgctcag tggaacgaaa actcacgtta agggattttg gtcatgagat tatcaaaaag     6600
gatcttcacc tagatccttt taaattaaaa atgaagtttt aaatcaatct aaagtatata     6660
tgagtaaact tggtctgaca gttaccaatg cttaatcagt gaggcaccta tctcagcgat     6720
ctgtctattt cgttcatcca tagttgcctg actccccgtc gcgtagataa ctacgatacg     6780
ggagggctta ccatctggcc ccagtgctgc aatgataccg cgagacccac gctcaccggc     6840
tccagattta tcagcaataa accagccagc cggaagggcc gagcgcagaa gtggtcctgc     6900
aactttatcc gcctccatcc agtctattaa ttgttgccgg gaagctagag taagtagttc     6960
gccagttaat agtttgcgca acgttgttgc cattgctaca ggcatcgtgg tgtcacgctc     7020
gtcgtttggt atggcttcat tcagctccgg ttcccaacga tcaaggcgag ttacatgatc     7080
ccccatgttg tgcaaaaaag cggttagctc cttcggtcct ccgatcgttg tcagaagtaa     7140
gttggccgca gtgttatcac tcatggttat ggcagcactg cataattctc ttactgtcat     7200
gccatccgta agatgctttt ctgtgactgg tgagtactca accaagtcat tctgagaata     7260
gtgtatgcgg cgaccgagtt gctcttgccc ggcgtcaata cgggataata ccgcgccaca     7320
tagcagaact ttaaaagtgc tcatcattgg aaaacgttct tcggggcgaa aactctcaag     7380
gatcttaccg ctgttgagat ccagttcgat gtaaccccact cgtgcaccca actgatcttc     7440
agcatctttt actttcacca gcgtttctgg gtgagcaaaa acaggaaggc aaaatgccgc     7500
aaaaaaggga ataagggcga cacggaaatg ttgaatactc atactcttcc ttttcaata     7560 ttattgaagc atttatcagg gttattgtct catgagcgga tacatatttg aatgtattta     7620
gaaaaataaa caaatagggg ttccgcgcac atttccccga aaagtgccac ctgacgtcga     7680
cggatcggga gatcgta                                                   7697
```

<210> SEQ ID NO 3
<211> LENGTH: 9905
<212> TYPE: DNA
<213> ORGANISM: Artificial Sequence
<220> FEATURE:
<223> OTHER INFORMATION: Plasmid pXC1, Microbix Corp., Toronto, ON, Canada

<400> SEQUENCE: 3

```
cccttccagc tctctgcccc ttttggattg aagccaatat gataatgagg gggtggagtt       60
tgtgacgtgg cgcggggcgt gggaacgggg cgggtgacgt agtagtgtgg cggaagtgtg      120
atgttgcaag tgtggcggaa cacatgtaag cgacggatgt ggcaaaagtg acgttttttgg     180 tgtgcgccgg tgtacacagg aagtgacaat tttcgcgcgg ttttaggcgg atgttgtagt      240
aaatttgggc gtaaccgagt aagatttggc cattttcgcg gaaaactga ataagaggaa       300 gtgaaatctg aataatttttg tgttactcat agcgcgtaat atttgtctag ggccgcgggg     360
actttgaccg tttacgtgga gactcgccca ggtgtttttc tcaggtgttt tccgcgttcc      420
gggtcaaagt tggcgtttta ttattatagt cagctgacgt gtagtgtatt tatacccggt      480
```

```
gagttcctca agaggccact cttgagtgcc agcgagtaga gttttctcct ccgagccgct    540
ccgacaccgg gactgaaaat gagacatatt atctgccacg gaggtgttat taccgaagaa    600
atggccgcca gtcttttgga ccagctgatc gaagaggtac tggctgataa tcttccacct    660
cctagccatt ttgaaccacc taccottcac gaactgtatg atttagacgt gacggccccc    720
gaagatccca acgaggaggc ggtttcgcag attttcccg actctgtaat gttggcggtg    780
caggaaggga ttgacttact cacttttccg ccggcgcccg gttctccgga gccgcctcac    840 cttccggc agcccgagca gccggagcag agagccttgg gtccggtttc tatgccaaac    900
cttgtaccgg aggtgatcga tcttacctgc cacgaggctg gctttccacc cagtgacgac    960
gaggatgaag agggtgagga gtttgtgtta gattatgtgg agcacccgg gcacggttgc   1020 aggtcttgtc attatcaccg gaggaatacg ggggacccag atattatgtg ttcgctttgc   1080
tatatgagga cctgtggcat gttttgtctac agtaagtgaa aattatgggc agtgggtgat   1140
agagtggtgg gtttggtgtg gtaatttttt ttttaattttt tacagttttg tggtttaaag   1200
aattttgtat tgtgattttt ttaaaaggtc ctgtgtctga acctgagcct gagcccgagc   1260
cagaaccgga gcctgcaaga cctacccgcc gtcctaaaat ggcgcctgct atcctgagac   1320
gcccgacatc acctgtgtct agagaatgca atagtagtac ggatagctgt gactccggtc   1380
cttctaacac acctcctgag atacacccgg tggtcccgct gtgccccatt aaaccagttg   1440
ccgtgagagt tggtgggcgt cgccaggctg tggaatgtat cgaggacttg cttaacgagc   1500
ctgggcaacc tttggacttg agctgtaaac gccccaggcc ataaggtgta aacctgtgat   1560
tgcgtgtgtg gttaacgcct ttgtttgctg aatgagttga tgtaagttta ataaagggtg   1620
agataatgtt taacttgcat ggcgtgttaa atggggcggg gcttaaaggg tatataatgc   1680
gccgtgggct aatcttggtt acatctgacc tcatggaggc ttgggagtgt ttggaagatt   1740
tttctgctgt gcgtaacttg ctggaacaga gctctaacag tacctcttgg ttttggaggt   1800
ttctgtgggg ctcatcccag gcaaagttag tctgcagaat taaggaggat tacaagtggg   1860
aatttgaaga gcttttgaaa tcctgtggtg agctgtttga ttctttgaat ctgggtcacc   1920
aggcgctttt ccaagagaag gtcatcaaga ctttggattt ttccacaccg gggcgcgctg   1980
cggctgctgt tgcttttttg agttttataa aggataaatg gagcgaagaa acccatctga   2040 gcgggggta cctgctggat tttctggcca tgcatctgtg gagagcggtt gtgagacaca   2100
agaatcgcct gctactgttg tcttccgtcc gcccggcgat aataccgacg gaggagcagc   2160
agcagcagca ggaggaagcc aggcggcggc ggcaggagca gagcccatgg aacccgagag   2220
ccggcctgga ccctcgggaa tgaatgttgt acaggtggct gaactgtatc cagaactgag   2280
acgcattttg acaattacag aggatgggca ggggctaaag ggggtaaaga gggagcgggg   2340
ggcttgtgag gctacagagg aggctaggaa tctagctttt agcttaatga ccagacaccg   2400
tcctgagtgt attactttttc aacagatcaa ggataattgc gctaatgagc ttgatctgct   2460
ggcgcagaag tattccatag agcagctgac cacttactgg ctgcagccag gggatgattt   2520
tgaggaggct attagggtat atgcaaaggt ggcacttagg ccagattgca agtacaagat   2580
cagcaaactt gtaaatatca ggaattgttg ctacatttct gggaacgggg ccgaggtgga   2640
gatagatacg gaggataggg tggccttag atgtagcatg ataaatatgt ggccgggggt   2700
gcttggcatg gacggggtgg ttattatgaa tgtaaggttt actggcccca atttttagcgg   2760 tacgttttc ctgccaata ccaaccttat cctacgggt gtaagcttct atgggtttaa   2820
caatacctgt gtggaagcct ggaccgatgt aaggggttcgg ggctgtgcct tttactgctg   2880
```

```
ctggaagggg gtggtgtgtc gccccaaaag cagggcttca attaagaaat gcctctttga    2940
aaggtgtacc ttgggtatcc tgtctgaggg taactccagg gtgcgccaca atgtggcctc    3000
cgactgtggt tgcttcatgc tagtgaaaag cgtggctgtg attaagcata acatggtatg    3060
tggcaactgc gaggacaggg cctctcagat gctgacctgc tcggacggca actgtcacct    3120
gctgaagacc attcacgtag ccagccactc tcgcaaggcc tggccagtgt ttgagcataa    3180
catactgacc cgctgttcct tgcatttggg taacaggagg ggggtgttcc taccttacca    3240
atgcaatttg agtcacacta agatattgct tgagcccgag agcatgtcca aggtgaacct    3300
gaacggggtg tttgacatga ccatgaagat ctggaaggtg ctgaggtacg atgagacccg    3360
caccaggtgc agaccctgcg agtgtggcgg taaacatatt aggaaccagc ctgtgatgct    3420
ggatgtgacc gaggagctga ggcccgatca cttggtgctg gcctgcaccc gcgctgagtt    3480
tggctctagc gatgaagata cagattgagg tactgaaatg tgtgggcgtg gcttaagggt    3540
gggaaagaat atataaggtg ggggtcttat gtagttttgt atctgttttg cagcagccgc    3600
cgccgccatg agcaccaact cgtttgatgg aagcattgtg agctcatatt tgacaacgcg    3660
catgccccca tgggccgggg tgcgtcagaa tgtgatgggc tccagcattg atggtcgccc    3720
cgtcctgccc gcaaactcta ctaccttgac ctacgagacc gtgtctggaa cgccgttgga    3780
gactgcagcc tccgccgccg cttcagccgc tgcagccacc gcccgcggga ttgtgactga    3840
ctttgctttc ctgagcccgc ttgcaagcag tgcagcttcc cgttcatccg cccgcgatga    3900
caagttgacg gctcttttgg cacaattgga ttctttgacc cgggaactta atgtcgtttc    3960
tcagcagctg ttggatctgc gccagcaggt ttctgccctg aaggcttcct cccctcccaa    4020
tgcggtttaa aacataaata aaaaaccaga ctctgtttgg atttggatca agcaagtgtc    4080
ttgctgtctt tatttagggg ttttgcgcgc gcggtaggcc cgggaccagc ggtctcggtc    4140
gttgagggtc ctgtgtattt tttccaggac gtggtaaagg tgactctgga tgttcagata    4200
catgggcata agcccgtctc tggggtggag gtagcaccac tgcagagctt catgctgcgg    4260
ggtggtgttg tagatgatcc agtcgtagca ggagcgctgg gcgtggtgcc taaaaatgtc    4320
tttcagtagc aagctgattg ccaggggcag gcccttggtg taagtgttta caaagcggtt    4380
aagctgggat gggtgcatac gtggggatat gagatgcatc ttggactgta ttttaggtt    4440 ggctatgttc ccagccatat ccctccgggg attcatgttg tgcagaacca ccagcacagt    4500
gtatccggtg cacttgggaa atttgtcatg tagcttagaa ggaaatgcgt ggaagaactt    4560
ggagacgccc ttgtgacctc caagattttc catgcattcg tccataatga tggcaatggg    4620
cccacgggcg gcggcctggg cgaagatatt tctgggatca ctaacgtcat agttgtgttc    4680
caggatgaga tcgtcatagg ccattttac aaagcgcggg cggagggtgc cagactgcgg    4740
tataatggtt ccatccggcc caggggcgta gttaccctca cagatttgca tttcccacgc    4800
tttgagttca gatgggggga tcatgtctac ctgcggggcg atgaagaaaa cggtttccgg    4860
ggtaggggag atcagctggg aagaaagcag gttcctgagc agctgcgact taccgcagcc    4920
ggtgggcccg taaatcacac ctattaccgg gtgcaactgg tagttaagag agctgcagct    4980
gccgtcatcc ctgagcaggg gggccacttg gttaagcatg tccctgactc gcatgttttc    5040
cctgaccaaa tccgccagaa ggcgctcgcc gcccagcgat agcagttctt gcaaggaagc    5100
aaagtttttc aacggtttga daccgtccgc cgtaggcatg cttttgagcg tttgaccaag    5160
cagttccagg cggtcccaca gctcggtcac ctgctctacg gcatctcgat ccagcatatc    5220
tcctcgtttc gcgggttggg gcggctttcg ctgtacggca gtagtcggtg ctcgtccaga    5280
```

```
cgggccaggg tcatgtcttt ccacgggcgc agggtcctcg tcagcgtagt ctgggtcacg    5340
gtgaagggt  gcgctccggg ctgcgcgctg gccagggtgc gcttgaggct ggtcctgctg    5400
gtgctgaagc gctgccggtc ttcgccctgc gcgtcggcca ggtagcattt gaccatggtg    5460
tcatagtcca gccctccgc  ggcgtggccc ttggcgcgca gcttgccctt ggaggaggcg    5520
ccgcacgagg ggcagtgcag acttttgagg gcgtagagct tgggcgcgag aaataccgat    5580
tccggggagt aggcatccgc gccgcaggcc ccgcagacgg tctcgcattc cacgagccag    5640
gtgagctctg gccgttcggg gtcaaaaacc aggtttcccc catgcttttt gatgcgtttc    5700
ttacctctgg tttccatgag ccggtgtcca cgctcggtga cgaaaaggct gtccgtgtcc    5760
ccgtatacag acttgagagg cctgtcctcg gcctgtcctc gaccgatgcc cttgagagcc    5820
ttcaacccag tcagctcctt ccggtgggcg cggggcatga ctatcgtcgc cgcacttatg    5880
actgtcttct ttatcatgca actcgtagga caggtgccgg cagcgctctg ggtcatttc     5940
ggcgaggacc gctttcgctg gagcgcgacg atgatcggcc tgtcgcttgc ggtattcgga    6000
atcttgcacg ccctcgctca agccttcgtc actggtcccg ccaccaaacg tttcggcgag    6060
aagcaggcca ttatcgccgg catggcggcc gacgcgctgg gctacgtctt gctggcgttc    6120
gcgacgcgag gctggatggc cttccccatt atgattcttc tcgcttccgg cggcatcggg    6180
atgcccgcgt gcaggccat  gctgtccagg caggtagatg acgaccatca gggacagctt    6240
caaggatcgc tcgcggctct taccagccta acttcgatca ctggaccgct gatcgtcacg    6300
gcgatttatg ccgcctcggc gagcacatgg aacgggttgg catggattgt aggcgccgcc    6360
ctataccttg tctgcctccc cgcgttgcgt cgcggtgcat ggagccgggc cacctcgacc    6420
tgaatggaag ccggcggcac ctcgctaacg gattcaccac tccaagaatt ggagccaatc    6480
aattcttgcg gagaactgtg aatgcgcaaa ccaacccttg gcagaacata tccatcgcgt    6540
ccgccatctc cagcagccgc acgcggcgca tctcgggcag cgttgggtcc tggccacggg    6600
tgcgcatgat cgtgctcctg tcgttgagga cccggctagg ctggcggggt tgccttactg    6660
gttagcagaa tgaatcaccg atacgcgagc gaacgtgaag cgactgctgc tgcaaaacgt    6720
ctgcgacctg agcaacaaca tgaatggtct tcggtttccg tgtttcgtaa agtctggaaa    6780
cgcggaagtc agcgccctgc accattatgt tccggatctg catcgcagga tgctgctggc    6840
taccctgtgg aacacctaca tctgtattaa cgaagcgctg gcattgaccc tgagtgattt    6900
ttctctggtc ccgccgcatc cataccgcca gttgtttacc ctcacaacgt tccagtaacc    6960
gggcatgttc atcatcagta acccgtatcg tgagcatcct ctctcgtttc atcggtatca    7020
ttaccccat  gaacagaaat ccccttaca  cggaggcatc agtgaccaaa caggaaaaaa    7080
ccgcccttaa catggcccgc tttatcagaa gccagacatt aacgcttctg gagaaactca    7140
acgagctgga cgcggatgaa caggcagaca tctgtgaatc gcttcacgac cacgctgatg    7200
agctttaccg cagctgcctc gcgcgtttcg gtgatgacgg tgaaaacctc tgacacatgc    7260
agctcccgga gacggtcaca gcttgtctgt aagcggatgc cgggagcaga caagcccgtc    7320
agggcgcgtc agcgggtgtt ggcgggtgtc ggggcgcagc catgacccag tcacgtagcg    7380
atagcggagt gtatactggc ttaactatgc ggcatcagag cagattgtac tgagagtgca    7440
ccatatgcgg tgtgaaatac cgcacagatg cgtaaggaga aaataccgca tcaggcgctc    7500
ttccgcttcc tcgctcactg actcgctgcg ctcggtcgtt cggctgcggc gagcggtatc    7560
agctcactca aaggcggtaa tacggttatc cacagaatca ggggataacg caggaaagaa    7620
catgtgagca aaaggccagc aaaaggccag gaaccgtaaa aaggccgcgt tgctggcgtt    7680
```

```
tttccatagg ctccgccccc ctgacgagca tcacaaaaat cgacgctcaa gtcagaggtg    7740
gcgaaacccg acaggactat aaagatacca ggcgtttccc cctggaagct ccctcgtgcg    7800
ctctcctgtt ccgaccctgc cgcttaccgg atacctgtcc gcctttctcc cttcgggaag    7860
cgtggcgctt tctcatagct cacgctgtag gtatctcagt tcggtgtagg tcgttcgctc    7920
caagctgggc tgtgtgcacg aaccccccgt tcagcccgac cgctgcgcct tatccggtaa    7980
ctatcgtctt gagtccaacc cggtaagaca cgacttatcg ccactggcag cagccactgg    8040
taacaggatt agcagagcga ggtatgtagg cggtgctaca gagttcttga agtggtggcc    8100
taactacggc tacactagaa ggacagtatt tggtatctgc gctctgctga agccagttac    8160
cttcggaaaa agagttggta gctcttgatc cggcaaacaa accaccgctg gtagcggtgg    8220
ttttttttgtt tgcaagcagc agattacgcg cagaaaaaaa ggatctcaag aagatccttt    8280
gatcttttct acgggtctg acgctcagtg gaacgaaaac tcacgttaag ggattttggt     8340
catgagatta tcaaaaagga tcttcaccta gatccttta aattaaaaat gaagttttaa     8400
atcaatctaa agtatatatg agtaaacttg gtctgacagt taccaatgct taatcagtga    8460
ggcacctatc tcagcgatct gtctatttcg ttcatccata gttgcctgac tccccgtcgt    8520
gtagataact acgatacggg agggcttacc atctggcccc agtgctgcaa tgataccgcg    8580
agacccacgc tcaccggctc cagatttatc agcaataaac cagccagccg aagggccga    8640
gcgcagaagt ggtcctgcaa ctttatccgc ctccatccag tctattaatt gttgccggga    8700
agctagagta agtagttcgc cagttaatag tttgcgcaac gttgttgcca ttgctgcagg    8760
catcgtggtg tcacgctcgt cgtttggtat ggcttcattc agctccggtt cccaacgatc    8820
aaggcgagtt acatgatccc ccatgttgtg caaaaaagcg gttagctcct tcggtcctcc    8880
gatcgttgtc agaagtaagt tggccgcagt gttatcactc atggttatgg cagcactgca    8940
taattctctt actgtcatgc catccgtaag atgcttttct gtgactggtg agtactcaac    9000
caagtcattc tgagaatagt gtatgcggcg accgagttgc tcttgcccgg cgtcaacacg    9060
ggataatacc gcgccacata gcagaacttt aaaagtgctc atcattggaa aacgttcttc    9120
ggggcgaaaa ctctcaagga tcttaccgct gttgagatcc agttcgatgt aacccactcg    9180
tgcacccaac tgatcttcag catctttta ctttcaccagc gtttctgggt gagcaaaaac    9240
aggaaggcaa aatgccgcaa aaaagggaat aagggcgaca cggaaatgtt gaatactcat    9300
actcttcctt tttcaatatt attgaagcat ttatcagggt tattgtctca tgagcggata    9360
catatttgaa tgtatttaga aaaataaaca aataggggtt ccgcgcacat ttccccgaaa    9420
agtgccacct gacgtctaag aaaccattat tatcatgaca ttaacctata aaaataggcg    9480
tatcacgagg ccctttcgtc ttcaagaatt ctcatgtttg acagcttatc atcgataagc    9540
tttaatgcgg tagtttatca cagttaaatt gctaacgcag tcaggcaccg tgtatgaaat    9600
ctaacaatgc gctcatcgtc atcctcggca ccgtcaccct ggatgctgta ggcataggct    9660
tggttatgcc ggtactgccg ggcctcttgc gggatatcgt ccattccgac agcatcgcca    9720
gtcactatgg cgtgctgcta gcgctatatg cgttgatgca atttctatgc gcacccgttc    9780
tcggagcact gtccgaccgc tttggccgcc gcccagtcct gctcgcttcg ctacttggag    9840
ccactatcga ctacgcgatc atggcgacca cacccgtcct gtggatccgg gccccatttt   9900
ccct                                                                 9905
```

<210> SEQ ID NO 4
<211> LENGTH: 7323

```
<212> TYPE: DNA
<213> ORGANISM: Artificial Sequence
<220> FEATURE:
<223> OTHER INFORMATION: Plasmid pSwitch, Invitrogen Corp., Carlsbad,
      CA

<400> SEQUENCE: 4
gacggatcgg gagatcattc gagcttgcat gcctgcaggt cgaagcggag tactgtcctc      60
cgagtttaaa agcggagtac tgtcctccga ggatatcagc ggagtactgt cctccgagtc     120
gcgaagcgga gtactgtcct ccgagatcga tgtcgacccc gcccagcgtc ttgtcattgg     180
cgaattcgaa cacgcagatg cagtcggggc ggcgcggtcc gaggtccact tcgcatatta     240
aggtgacgcg tgtggcctcg aatcgcctgg agacgccatc cacgctgttt tgacctccat     300
agaagacacc gggaccgatc cagcctccgc ggccgggaac ggtgcattgg aacgcggatt     360
ccccgtgtta attaacaggt aagtgtcttc ctcctgtttc cttcccctgc tattctgctc     420
aaccttccta tcagaaactg cagtatctgt attttttgcta gcagtaatac taacggttct     480
ttttttctct tcacaggcca ccaagctacc ggtccaccat ggactccag cagccagatc      540
tgaagctact gtcttctatc gaacaagcat gcgatatttg ccgacttaaa aagctcaagt     600
gctccaaaga aaaccgaagt gcgccaagt gtctgaagaa caactgggag tgtcgctact      660
ctcccaaaac caaaaggtct ccgctgacta gggcacatct gacagaagtg gaatcaaggc     720
tagaaagact ggaacagcta tttctactga ttttcctcg agaagacctt gacatgattt      780
tgaaaatgga ttcttacag gatataaaag cattgttaga attcccgggt gtcgaccaga     840
aaagttcaa taaagtcaga gttgtgagag cactggatgc tgttgctctc ccacagccag     900
tgggcgttcc aaatgaaagc caagccctaa gccagagatt cacttttca ccaggtcaag     960
acatacagtt gattccacca ctgatcaacc tgttaatgag cattgaacca gatgtgatct    1020
atgcaggaca tgacaacaca aaacctgaca cctccagttc tttgctgaca agtcttaatc    1080
aactaggcga gaggcaactt cttttcagtag tcaagtggtc taaatcattg ccaggttttc    1140
gaaacttaca tattgatgac cagataactc tcattcagta ttcttggatg agcttaatgg    1200
tgtttggtct aggatggaga tcctacaaac acgtcagtgg gcagatgctg tattttgcac    1260
ctgatctaat actaaatgaa cagcggatga agaatcatc attctattca ttatgcctta    1320
ccatgtggca gatcccacag gagtttgtca agcttcaagt tagccaagaa gagttcctct    1380
gtatgaaagt attgttactt cttaatacaa ttccttgga agggctacga agtcaaaccc    1440
agtttgagga gatgaggtca agctacatta gagagctcat caaggcaatt ggtttgaggc    1500
aaaaaggagt tgtgtcgagc tcacagcgtt tctatcaact tacaaaactt cttgataact    1560
tgcatgatct tgtcaaacaa cttcatctgt actgcttgaa tacatttatc cagtcccggg    1620
cactgagtgt tgaatttcca gaaatgatgt ctgaagttat tgctgggtcg acgcccatgg    1680
aattccagta cctgccagat acagacgatc gtcaccggga tgaggagaaa cgtaaaagga    1740
catatgagac cttcaagagc atcatgaaga gagtcctttt cagcggaccc accgaccccc    1800
ggcctccacc tcgacgcatt gctgtgcctt ccgcagctc agcttctgtc cccaagccag    1860
caccccagcc ctatcccttt acgtcatccc tgagcaccat caactatgat gagtttccca    1920
ccatggtgtt tccttctggg cagatcagcc aggcctcggc cttggcccg gcccctcccc    1980
aagtcctgcc ccaggctcca gccctgcccc tgctccagc catggtatca gctctggccc    2040
aggcccagc cctgtccca gtcctagccc caggccctcc tcaggctgtg gccccacctg    2100
cccccaagcc cacccaggct ggggaaggaa cgctgtcaga ggccctgctg cagctgcagt    2160
```

```
ttgatgatga agacctgggg gccttgcttg gcaacagcac agacccagct gtgttcacag    2220
acctggcatc cgtcgacaac tccgagtttc agcagctgct gaaccagggc atacctgtgg    2280 cccccacac aactgagccc atgctgatgg agtaccctga ggctataact cgcctagtga     2340
caggggccca gaggccccccc gacccagctc ctgctccact gggggccccg ggctcccca    2400 atggcctcct ttcaggagat gaagacttct cctccattgc ggacatggac ttctcagccc    2460
tgctgagtca gatcagctcc taaggatcct ccggactaga aaagccgaat tctgcaggaa    2520
ttgggtggca tccctgtgac ccctccccag tgcctctcct ggccctggaa gttgccactc    2580
cagtgcccac cagccttgtc ctaataaaat taagttgcat cattttgtct gactaggtgt    2640
ccttctataa tattatgggg tggagggggg tggtatggag caaggggcaa gttgggaaga    2700
caacctgtag ggctcgaggg ggggcccgaa acccgctgat cagcctcgac tgtgccttct    2760
agttgccagc catctgttgt ttgcccctcc cccgtgcctt ccttgaccct ggaaggtgcc    2820
actcccactg tccttttccta ataaaatgag gaaattgcat cgcattgtct gagtaggtgt    2880
cattctattc tgggggggtgg ggtggggcag gacagcaagg gggaggattg ggaagacaat    2940
agcaaggcat gctggggatg cggtgggctc tatggcttct gaggcggaaa gaaccagctg    3000
gggctctagg gggtatcccc acgcgccctg tagcggcgca ttaagcgcgg cgggtgtggt    3060
ggttacgcgc agcgtgaccg ctacacttgc cagcgcccta gcgcccgctc ctttcgcttt    3120
cttcccttcc tttctcgcca cgttcgccgg ctttccccgt caagctctaa atcggggggct    3180 ccctttaggg ttccgattta gtgctttacg gcacctcgac cccaaaaaac ttgattaggg    3240
tgatggttca cgtagtgggc catcgccctg atagacggtt tttcgccctt tgacgttgga    3300
gtccacgttc tttaatagtg gactcttgtt ccaaactgga acaacactca accctatctc    3360
ggtctattct tttgatttat aagggatttt gccgatttcg gcctattggt taaaaaatga    3420
gctgatttaa caaaaattta acgcgaatta attctgtgga atgtgtgtca gttagggtgt    3480
ggaaagtccc caggctcccc agcaggcaga agtatgcaaa gcatgcatct caattagtca    3540
gcaaccaggt gtggaaagtc cccaggctcc ccagcaggca gaagtatgca aagcatgcat    3600
ctcaattagt cagcaaccat agtcccgccc ctaactccgc ccatcccgcc ctaactccg    3660 cccagttccg cccattctcc gccccatggc tgactaattt ttttttattta tgcagaggcc    3720 gaggccgcct ctgcctctga gctattccag aagtagtgag gaggcttttt tggaggccta    3780
ggcttttgca aaaagctccc gggagcttgt atatccattt tcggatctga tcagcacgtg    3840 atgaaaagc ctgaactcac cgcgacgtct gtcgagaagt ttctgatcga aaagttcgac    3900
agcgtctccg acctgatgca gctctcggag gcgaagaat ctcgtgcttt cagcttcgat    3960
gtaggagggc gtggatatgt cctgcgggta aatagctgcg ccgatggttt ctacaaagat    4020
cgttatgttt atcggcactt tgcatcggcc gcgctcccga ttccggaagt gcttgacatt    4080
ggggaattca gcgagagcct gacctattgc atctcccgcc gtgcacaggg tgtcacgttg    4140
caagacctgc ctgaaaccga actgcccgct gttctgcagc cggtcgcgga ggccatggat    4200
gcgatcgctg cggccgatct tagccagacg agcgggttcg gcccattcgg accgcaagga    4260
atcggtcaat acactacatg gcgtgatttc atatgcgcga ttgctgatcc ccatgtgtat    4320
cactggcaaa ctgtgatgga cgacaccgtc agtgcgtccg tcgcgcaggc tctcgatgag    4380
ctgatgcttt gggccgagga ctgccccgaa gtccggcacc tcgtgcacgc ggatttcggc    4440
tccaacaatg tcctgacgga caatggccgc ataacagcgg tcattgactg agcgaggcg    4500 atgttcgggg attcccaata cgaggtcgcc aacatcttct tctggaggcc gtggttggct    4560
```

```
tgtatggagc agcagacgcg ctacttcgag cggaggcatc cggagcttgc aggatcgccg   4620
cggctccggg cgtatatgct ccgcattggt cttgaccaac tctatcagag cttggttgac   4680
ggcaatttcg atgatgcagc ttgggcgcag ggtcgatgcg acgcaatcgt ccgatccgga   4740
gccgggactg tcgggcgtac acaaatcgcc cgcagaagcg cggccgtctg gaccgatggc   4800
tgtgtagaag tactcgccga tagtggaaac cgacgcccca gcactcgtcc gagggcaaag   4860
gaatagcacg tgctacgaga tttcgattcc accgccgcct tctatgaaag gttgggcttc   4920
ggaatcgttt tccgggacgc cggctggatg atcctccagc gcgggatct catgctggag    4980 ttcttcgccc accccaactt gtttattgca gcttataatg gttacaaata aagcaatagc   5040
atcacaaatt tcacaaataa agcatttttt tcactgcatt ctagttgtgg tttgtccaaa   5100
ctcatcaatg tatcttatca tgtctgtata ccgtcgacct ctagctagag cttggcgtaa   5160
tcatggtcat agctgtttcc tgtgtgaaat tgttatccgc tcacaattcc acacaacata   5220
cgagccggaa gcataaagtg taaagcctgg ggtgcctaat gagtgagcta actcacatta   5280
attgcgttgc gctcactgcc cgctttccag tcgggaaacc tgtcgtgcca gctgcattaa   5340
tgaatcggcc aacgcgcggg gagaggcggt ttgcgtattg ggcgctcttc cgcttcctcg   5400
ctcactgact cgctgcgctc ggtcgttcgg ctgcggcgag cggtatcagc tcactcaaag   5460
gcggtaatac ggttatccac agaatcaggg gataacgcag gaaagaacat gtgagcaaaa   5520
ggccagcaaa aggccaggaa ccgtaaaaag gccgcgttgc tggcgttttt ccataggctc   5580
cgcccccctg acgagcatca caaaaatcga cgctcaagtc agaggtggcg aaacccgaca   5640
ggactataaa gataccaggc gtttccccct ggaagctccc tcgtgcgctc tcctgttccg   5700
accctgccgc ttaccggata cctgtccgcc tttctccctt cgggaagcgt ggcgctttct   5760
catagctcac gctgtaggta tctcagttcg gtgtaggtcg ttcgctccaa gctgggctgt   5820
gtgcacgaac ccccgttca gcccgaccgc tgcgccttat ccggtaacta tcgtcttgag   5880
tccaacccgg taagacacga cttatcgcca ctggcagcag ccactggtaa caggattagc   5940
agagcgaggt atgtaggcgg tgctacagag ttcttgaagt ggtggcctaa ctacggctac   6000
actagaagaa cagtatttgg tatctgcgct ctgctgaagc cagttacctt cggaaaaaga   6060
gttggtagct cttgatccgg caaacaaacc accgctggta gcggtggttt ttttgtttgc   6120
aagcagcaga ttacgcgcag aaaaaaagga tctcaagaag atcctttgat cttttctacg   6180
gggtctgacg ctcagtggaa cgaaaactca cgttaaggga ttttggtcat gagattatca   6240
aaaagaatct tcacctagat ccttttaaat taaaaatgaa gttttaatcc aatctaaagt   6300
atatatgagt aaacttggtc tgacagttac caatgcttaa tcagtgaggc acctatctca   6360
gcgatctgtc tatttcgttc atccatagtt gcctgactcc ccgtcgtgta gataactacg   6420
atacgggagg gcttaccatc tggccccagt gctgcaatga taccgcgaga cccacgctca   6480
ccggctccag atttatcagc aataaaccag ccagccggaa gggccgagcg cagaagtggt   6540
cctgcaactt tatccgcctc catccagtct attaattgtt gccgggaagc tagagtaagt   6600
agttcgccag ttaatagttt gcgcaacgtt gttgccattg ctacaggcat cgtggtgtca   6660
cgctcgtcgt ttggtatggc ttcattcagc tccggttccc aacgatcaag gcgagttaca   6720
tgatccccca tgttgtgcaa aaaagcggtt agctccttcg gtcctccgat cgttgtcaga   6780
agtaagttgg ccgcagtgtt atcactcatg gttatggcag cactgcataa ttctcttact   6840
gtcatgccat ccgtaagatg cttttctgtg actggtgagt actcaaccaa gtcattctga   6900
gaatagtgta tgcggcgacc gagttgctct tgcccggcgt caatacggga taataccgcg   6960
```

```
ccacatagca gaactttaaa agtgctcatc attggaaaac gttcttcggg gcgaaaactc    7020
tcaaggatct taccgctgtt gagatccagt tcgatgtaac ccactcgtgc acccaactga    7080
tcttcagcat cttttacttt caccagcgtt tctgggtgag caaaacagg  aaggcaaaat    7140 gccgcaaaaa agggaataag ggcgacacgg aaatgttgaa tactcatact cttccttttt    7200
caatattatt gaagcattta tcaggttat  tgtctcatga gcggatacat atttgaatgt    7260
atttagaaaa ataaacaaat aggggttccg cgcacatttc cccgaaaagt gccacctgac    7320
gtc                                                                 7323
```

```
<210> SEQ ID NO 5
<211> LENGTH: 41
<212> TYPE: DNA
<213> ORGANISM: Artificial Sequence
<220> FEATURE:
<223> OTHER INFORMATION: Single-stranded DNA, mutagenesis primer

<400> SEQUENCE: 5
cagcctccgt ggcctcgcga tcgcagcatc cgacaagaag c                        41

<210> SEQ ID NO 6
<211> LENGTH: 30
<212> TYPE: DNA
<213> ORGANISM: Artificial Sequence
<220> FEATURE:
<223> OTHER INFORMATION: Single-stranded DNA, PCR primer

<400> SEQUENCE: 6
tatgcgatcg cttctgacac aacagtctcg                                     30

<210> SEQ ID NO 7
<211> LENGTH: 31
<212> TYPE: DNA
<213> ORGANISM: Artificial Sequence
<220> FEATURE:
<223> OTHER INFORMATION: Single-stranded DNA, PCR primer

<400> SEQUENCE: 7
tatgcgatcg ccttaagagc tgtaattgaa c                                   31

<210> SEQ ID NO 8
<211> LENGTH: 26
<212> TYPE: DNA
<213> ORGANISM: Artificial Sequence
<220> FEATURE:
<223> OTHER INFORMATION: Single-stranded DNA, mutagenesis primer

<400> SEQUENCE: 8
tatggcgcgc cacctgacgt cgacgg                                         26

<210> SEQ ID NO 9
<211> LENGTH: 36
<212> TYPE: DNA
<213> ORGANISM: Artificial Sequence
<220> FEATURE:
<223> OTHER INFORMATION: Single-stranded DNA, mutagenesis primer

<400> SEQUENCE: 9
ataggcgcgc cggtaagctt aagtttaaac gctagc                              36

<210> SEQ ID NO 10
<211> LENGTH: 29
<212> TYPE: DNA
<213> ORGANISM: Artificial Sequence
<220> FEATURE:
```

```
<223> OTHER INFORMATION: Single-stranded DNA, PCR primer

<400> SEQUENCE: 10
tatggcgcgc ctcgacggat cgggagatc                                    29

<210> SEQ ID NO 11
<211> LENGTH: 28
<212> TYPE: DNA
<213> ORGANISM: Artificial Sequence
<220> FEATURE:
<223> OTHER INFORMATION: Single-stranded DNA, PCR primer

<400> SEQUENCE: 11
tatggcgcgc ctgttaatta acacgggg                                     28

<210> SEQ ID NO 12
<211> LENGTH: 50
<212> TYPE: DNA
<213> ORGANISM: Artificial Sequence
<220> FEATURE:
<223> OTHER INFORMATION: Single-stranded DNA, mutagenesis primer

<400> SEQUENCE: 12
cgagtctaga gatatcgaat tcaggcgcgc cttgtcgact cgaagatctg             50

<210> SEQ ID NO 13
<211> LENGTH: 28
<212> TYPE: DNA
<213> ORGANISM: Artificial Sequence
<220> FEATURE:
<223> OTHER INFORMATION: Single-stranded DNA, PCR primer

<400> SEQUENCE: 13
tattctagaa ccaagctacc ggtccacc                                     28

<210> SEQ ID NO 14
<211> LENGTH: 29
<212> TYPE: DNA
<213> ORGANISM: Artificial Sequence
<220> FEATURE:
<223> OTHER INFORMATION: Single-stranded DNA, PCR primer

<400> SEQUENCE: 14
ataggcgcgc ctcagaagcc atagagccc                                    29

<210> SEQ ID NO 15
<211> LENGTH: 47
<212> TYPE: DNA
<213> ORGANISM: Artificial Sequence
<220> FEATURE:
<223> OTHER INFORMATION: Single-stranded DNA, mutagenesis primer

<400> SEQUENCE: 15
accaagctac cggtcctcca tgtactccca gcagccagat ctgaagc                47

<210> SEQ ID NO 16
<211> LENGTH: 29
<212> TYPE: DNA
<213> ORGANISM: Artificial Sequence
<220> FEATURE:
<223> OTHER INFORMATION: Single-stranded DNA, PCR primer

<400> SEQUENCE: 16
atacctaggc ggatccgacc tcccacagc                                    29

<210> SEQ ID NO 17
```

```
<211> LENGTH: 30
<212> TYPE: DNA
<213> ORGANISM: Artificial Sequence
<220> FEATURE:
<223> OTHER INFORMATION: Single-stranded DNA, PCR primer

<400> SEQUENCE: 17
atagcggccg cccggaggat ccttaggagc                                          30
```